(12) United States Patent
Lanier et al.

(10) Patent No.: US 7,879,862 B2
(45) Date of Patent: Feb. 1, 2011

(54) PYRAZOLO[1,5-ALPHA]PYRIMIDINYL DERIVATIVES USEFUL AS CORTICOTROPIN-RELEASING FACTOR (CRF) RECEPTOR ANTAGONISTS

(75) Inventors: Marion Lanier, San Diego, CA (US); John Edward Tellew, San Diego, CA (US); John P. Williams, San Diego, CA (US)

(73) Assignee: SmithKline Beecham (Cork) Limited, Currabinny, Carrigaline, County Cork (IE)

( * ) Notice: Subject to any disclaimer, the term of this patent is extended or adjusted under 35 U.S.C. 154(b) by 403 days.

(21) Appl. No.: 11/576,957

(22) PCT Filed: Oct. 19, 2005

(86) PCT No.: PCT/US2005/037576
§ 371 (c)(1),
(2), (4) Date: Apr. 10, 2007

(87) PCT Pub. No.: WO2006/044958
PCT Pub. Date: Apr. 27, 2006

(65) Prior Publication Data
US 2008/0194589 A1    Aug. 14, 2008

Related U.S. Application Data

(60) Provisional application No. 60/620,060, filed on Oct. 19, 2004.

(30) Foreign Application Priority Data
Sep. 30, 2005    (GB) .................... 0519957.5

(51) Int. Cl.
  *A01N 43/90* (2006.01)
  *A61K 31/519* (2006.01)
  *C07D 487/00* (2006.01)
(52) U.S. Cl. .................... 514/259.3; 544/281
(58) Field of Classification Search .................... None
  See application file for complete search history.

(56) References Cited

U.S. PATENT DOCUMENTS

| | | | |
|---|---|---|---|
| 6,060,478 A | 5/2000 | Gilligan et al. ............ 514/258 |
| 6,589,947 B1 | 7/2003 | Hamanaka et al. | |
| 7,253,284 B2 | 8/2007 | DiFabio et al. | |
| 7,279,474 B2 | 10/2007 | Capelli et al. | |
| 7,462,622 B2 | 12/2008 | DiFabio et al. | |
| 2003/0139426 A1 | 7/2003 | Wilde et al. ............ 514/259.3 |
| 2005/0187224 A1 | 8/2005 | Gebauer et al. | |
| 2007/0004708 A1 | 1/2007 | Andriotti et al. | |
| 2007/0021429 A1 | 1/2007 | St. Denis | |
| 2007/0066640 A1 | 3/2007 | Castigtioni et al. | |
| 2007/0219232 A1 | 9/2007 | DiFabio et al. | |
| 2007/0287705 A1 | 12/2007 | Luo et al. | |
| 2007/0293511 A1 | 12/2007 | Luo et al. | |
| 2008/0064719 A1 | 3/2008 | Lanier et al. | |
| 2008/0306092 A1* | 12/2008 | Hossner ................ 514/259.3 |

FOREIGN PATENT DOCUMENTS

| | | |
|---|---|---|
| GB | 2378702 | 2/2003 |
| WO | WO97/29109 | 8/1997 |
| WO | WO98/03510 | 1/1998 |
| WO | WO98/08847 | 3/1998 |
| WO | WO01/23388 | 4/2001 |
| WO | WO2004/087707 | 10/2004 |
| WO | WO2005/063755 | 7/2005 |
| WO | WO2005/063756 | 7/2005 |

OTHER PUBLICATIONS

Robins, et. al., Journal of Heterocyclic Chemistry (1985), 22(3), 601-34.*

* cited by examiner

Primary Examiner—James O Wilson
Assistant Examiner—Jeffrey H Murray
(74) Attorney, Agent, or Firm—Barbara J. Carter

(57) ABSTRACT

CRF receptor antagonists are disclosed which may have utility in the treatment of a variety of disorders, including the treatment of disorders manifesting hypersecretion of CRF in mammals. The CRF receptor antagonists of this invention have the following structure: (I);

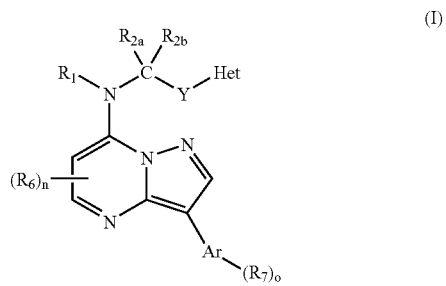

and pharmaceutically acceptable salts, esters, solvates, stereoisomers and prodrugs thereof, wherein $R_1$, $R_{2a}$, $R_{2b}$, Y, Het, n, o, $R_6$, Ar and $R_7$ are as defined herein. Compositions containing a CRF receptor antagonist in combination with a pharmaceutically acceptable carrier are also disclosed, as well as methods for use of the same.

20 Claims, 6 Drawing Sheets

PYRAZOLO[1,5-ALPHA]PYRIMIDINYL DERIVATIVES USEFUL AS CORTICOTROPIN-RELEASING FACTOR (CRF) RECEPTOR ANTAGONISTS

CROSS REFERENCE TO RELATED APPLICATION

This application is a 371 of International Application No. PCT/US2005/037576, filed 19 Oct. 2005, which claims priority of GB Application No. GB 0519957.5, filed 30 Sep. 2005 and U.S. Provisional Application No. 60/620,060, filed 19 Oct. 2004.

TECHNICAL FIELD

This invention relates generally to CRF receptor antagonists, and to methods of treating disorders by administration of such antagonists to a warm-blooded mammal in need thereof.

BACKGROUND OF THE INVENTION

The first corticotropin-releasing factor (CRF) was isolated from ovine hypothalami and identified as a 41-amino acid peptide (Vale et al., Science 213:1394-1397, 1981). Subsequently, sequences of human and rat CRF were isolated and determined to be identical but different from ovine-CRF in 7 of the 41 amino acid residues (Rivier et al., Proc. Natl. Acad. Sci. USA 80:4851, 1983; Shibahara et al., EMBO J. 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., Science 213:1394-1397, 1981). Briefly, CRF is believed to initiate its biological effects by binding to a plasma membrane receptor which has been found to be distributed throughout the brain (DeSouza et al., Science 224: 1449-1451, 1984), pituitary (DeSouza et al., Methods Enzymol. 124:560, 1986; Wynn et al., Biochem. Biophys. Res. Comm. 110:602-608, 1983), adrenals (Udelsman et al., Nature 319:147-150, 1986) and spleen (Webster, E. L., and E. B. DeSouza, Endocrinology 122:609-617, 1988). The CRF receptor is coupled to a GTP-binding protein (Perrin et al., Endocrinology 118:1171-1179, 1986) which mediates CRF-stimulated increase in intracellular production of cAMP (Bilezikjian, L. M., and W. W. Vale, Endocrinology 113:657-662, 1983). The receptor for CRF has now been cloned from rat (Perrin et al., Endo 133(6):3058-3061, 1993), and human brain (Chen et al., PNAS 90(19):8967-8971, 1993; Vita et al., FEBS 335(1):1-5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., J. Clin. Invest. 90:2555-2564, 1992; Sapolsky et al., Science 238:522-524, 1987; Tilders et al., Regul. Peptides 5:77-84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for a mammal exposed to a stressful environment. For example, intracerebroventricular injection of CRF results in behavioral activation (Sutton et al., Nature 297:331, 1982), persistent activation of the electroencephalogram (Ehlers et al., Brain Res. 278:332, 1983), stimulation of the sympathoadrenomedullary pathway (Brown et al., Endocrinology 110:928, 1982), an increase of heart rate and blood pressure (Fisher et al., Endocrinology 110:2222, 1982), an increase in oxygen consumption (Brown et al., Life Sciences 30:207, 1982), alteration of gastrointestinal activity (Williams et al., Am. J. Physiol. 253:G582, 1987), suppression of food consumption (Levine et al., Neuropharmacology 22:337, 1983), modification of sexual behavior (Sirinathsinghji et al., Nature 305:232, 1983), and immune function compromise (Irwin et al., Am. J. Physiol. 255:R744, 1988). Furthermore, clinical data suggests that CRF may be hypersecreted in the brain in depression, anxiety-related disorders, and anorexia nervosa. (DeSouza, Ann. Reports in Med. Chem. 25:215-223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., Science 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity.

CRF antagonists comprising compounds having a pyrazolo-[1,5a]-pyrimidine core are disclosed in the following patents and published applications: WO9729109, U.S. Pat. No. 6,313,124, WO9803510, WO9938868, WO9808847, JP2000038350, EP1097709 and U.S. Pat. No. 6,664,261. Further, this core is disclosed in application WO9535298 for analgesics, in application JP10101672 for adenosine reinforcement agents, in application JP10101671 for nitrogen monoxide synthase inhibitors, in application WO2001023387 for neuropeptide Y1 antagonists, in application WO2000044754 for fat accumulation inhibitors, and in application WO2003101993 for hepatitis C virus replication inhibitors.

Due to the physiological significance of CRF, the development of biologically-active small molecules having significant CRF receptor binding activity and which are capable of antagonizing the CRF receptor remains a desirable goal. Such CRF receptor antagonists may be useful in the treatment of endocrine, psychiatric and neurological conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

This invention is generally directed to CRF receptor antagonists, and more specifically to CRF receptor antagonists having the following general structure (I):

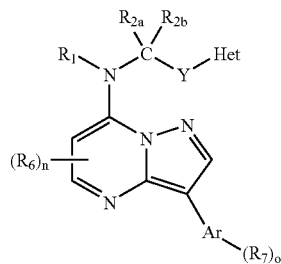

and pharmaceutically acceptable salts, esters, solvates, stereoisomers and prodrugs thereof, wherein:

$R_1$ is hydrogen, alkyl, substituted alkyl, haloalkyl, substituted haloalkyl, alkoxyalkyl, substituted alkoxyalkyl, arylalkyl, substituted arylalkyl, heterocyclealkyl, or substituted heterocyclealkyl;

$R_{2a}$ and $R_{2b}$ are independently hydrogen, $C_1$-$C_6$ alkyl, substituted $C_1$-$C_6$ alkyl, $C_1$-$C_6$ haloalkyl, substituted $C_1$-$C_6$ haloalkyl, arylalkyl, substituted arylalkyl, $C_1$-$C_6$ alkoxyalkyl, substituted $C_1$-$C_6$ alkoxyalkyl, alkylsulfonylalkyl, aminoalkyl, monoalkylaminoalkyl or dialkylaminoalkyl;

or $R_1$ together with the nitrogen to which it is attached and either $R_{2a}$ or $R_{2b}$ together with the carbon to which $R_{2a}$ and $R_{2b}$ are attached form a 4-7 membered heterocyclic ring;

or $R_{2a}$ and $R_{2b}$ together with the carbon atom to which they are attached form a ring of 3-7 members optionally containing within the ring —O—, —S— or —N($R_3$)—;

$R_3$ is alkyl, substituted alkyl, arylalkyl, substituted arylalkyl, acyl, —C(O)O$R_8$, —C(O)N$R_9R_{10}$, or S(O)$_2R_{11}$;

Y at each occurrence is independently a direct bond or —C($R_{4a}R_{4b}$)$_m$—;

m is 1 or 2;

$R_{4a}$ and $R_{4b}$ are independently hydrogen, $C_1$-$C_6$ alkyl, substituted $C_1$-$C_6$ alkyl, arylalkyl, substituted arylalkyl, $C_1$-$C_6$ alkoxyalkyl, substituted $C_1$-$C_6$ alkoxyalkyl, alkylsulfonylalkyl, aminoalkyl, monoalkylaminoalkyl or dialkylaminoalkyl;

or $R_{4a}$ and $R_{4b}$ together with the carbon atom to which they are attached form a ring of 3-7 members optionally containing within the ring —O—, —S— or —N($R_3$)—;

Het is

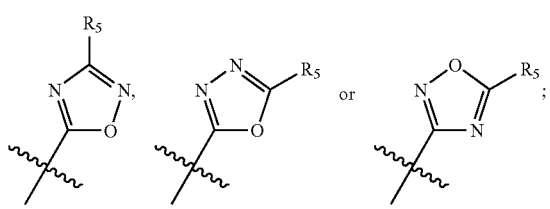

$R_5$ is hydrogen, halogen, $C_1$-$C_6$ alkyl, substituted $C_1$-$C_6$ alkyl, $C_1$-$C_6$ alkoxy, substituted $C_1$-$C_6$ alkoxy, amino, alkylamino or dialkylamino;

$R_6$ at each occurrence is independently halogen, $C_1$-$C_6$ alkyl or substituted $C_1$-$C_6$ alkyl;

n is an integer from 0-3 inclusive;

Ar is phenyl or pyridyl;

$R_7$ at each occurrence is independently halogen, alkyl, substituted alkyl, $C_1$-$C_6$ alkoxy, substituted $C_1$-$C_6$ alkoxy, —N$R_9R_{10}$, alkylsulfonyl or substituted alkylsulfonyl;

o is an integer from 0-3 inclusive; and each of $R_8$, $R_9$, $R_{10}$ and $R_{11}$ is hydrogen, $C_1$-$C_6$ alkyl, substituted $C_1$-$C_6$ alkyl, arylalkyl, substituted arylalkyl, $C_1$-$C_6$ alkoxyalkyl, substituted $C_1$-$C_6$ alkoxyalkyl, alkylsulfonylalkyl, aminoalkyl, monoalkylaminoalkyl or dialkylaminoalkyl.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

Figure 1:
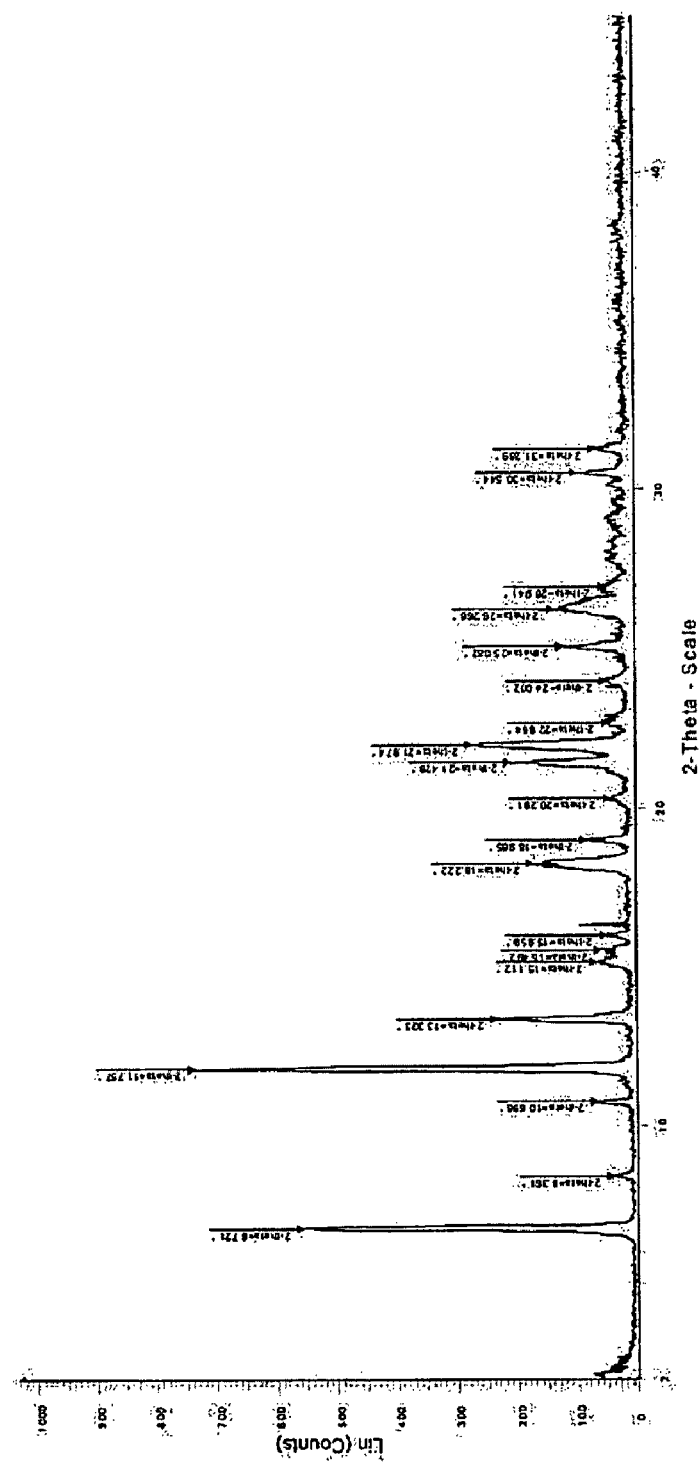
FIG. 1 shows X-Ray powder diffraction data obtained for polymorph Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine as described before. Form 1 is characterised by having an XRPD pattern with signals substantially as listed in Table 1.

The present invention is directed generally to compounds useful as corticotropin-releasing factor (CRF) receptor antagonists. In a first embodiment, the CRF receptor antagonists of this invention have the following structure (I):

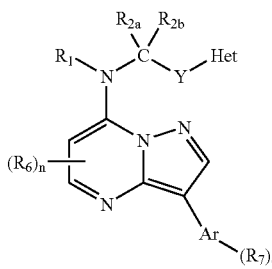

and pharmaceutically acceptable salts, esters, solvates, stereoisomers and prodrugs thereof, wherein:

$R_1$ is hydrogen, alkyl, substituted alkyl, haloalkyl, substituted haloalkyl, alkoxyalkyl, substituted alkoxyalkyl, arylalkyl, substituted arylalkyl, heterocyclealkyl, or substituted heterocyclealkyl;

$R_{2a}$ and $R_{2b}$ are independently hydrogen, $C_1$-$C_6$ alkyl, substituted $C_1$-$C_6$ alkyl, $C_1$-$C_6$ haloalkyl, substituted $C_1$-$C_6$ haloalkyl, arylalkyl, substituted arylalkyl, $C_1$-$C_6$ alkoxyalkyl, substituted $C_1$-$C_6$ alkoxyalkyl, alkylsulfonylalkyl, aminoalkyl, monoalkylaminoalkyl or dialkylaminoalkyl;

or $R_1$ together with the nitrogen to which it is attached and either $R_{2a}$ or $R_{2b}$ together with the carbon to which $R_{2a}$ and $R_{2b}$ are attached form a 4-7 membered heterocyclic ring;

or $R_{2a}$ and $R_{2b}$ together with the carbon atom to which they are attached form a ring of 3-7 members optionally containing within the ring —O—, —S— or —N($R_3$)—;

$R_3$ is alkyl, substituted alkyl, arylalkyl, substituted arylalkyl, acyl, —C(O)O$R_8$, —C(O)N$R_9R_{10}$, or S(O)$_2R_{11}$;

Y at each occurrence is independently a direct bond or —C($R_{4a}R_{4b}$)$_m$—;

m is 1 or 2;

$R_{4a}$ and $R_{4b}$ are independently hydrogen, $C_1$-$C_6$ alkyl, substituted $C_1$-$C_6$ alkyl, arylalkyl, substituted arylalkyl, $C_1$-$C_6$ alkoxyalkyl, substituted $C_1$-$C_6$ alkoxyalkyl, alkylsulfonylalkyl, aminoalkyl, monoalkylaminoalkyl or dialkylaminoalkyl;

or $R_{4a}$ and $R_{4b}$ together with the carbon atom to which they are attached form a ring of 3-7 members optionally containing within the ring —O—, —S— or —N($R_3$)—;

Het is

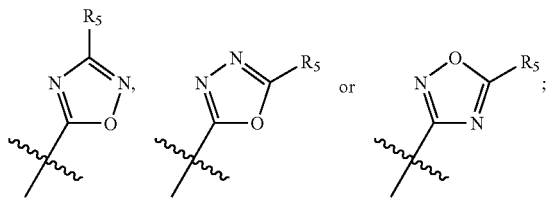

$R_5$ is hydrogen, halogen, $C_1$-$C_6$ alkyl, substituted $C_1$-$C_6$ alkyl, $C_1$-$C_6$ alkoxy, substituted $C_1$-$C_6$ alkoxy, amino, alkylamino or dialkylamino;

$R_6$ at each occurrence is independently halogen, $C_1$-$C_6$ alkyl or substituted $C_1$-$C_6$ alkyl;

n is an integer from 0-3 inclusive;

Ar is phenyl or pyridyl;

$R_7$ at each occurrence is independently halogen, alkyl, substituted alkyl, $C_1$-$C_6$ alkoxy, substituted $C_1$-$C_6$ alkoxy, —N$R_9R_{10}$, alkylsulfonyl or substituted alkylsulfonyl;

o is an integer from 0-3 inclusive; and each of $R_8$, $R_9$, $R_{10}$ and $R_{11}$ is hydrogen, $C_1$-$C_6$ alkyl, substituted $C_1$-$C_6$ alkyl, arylalkyl, substituted arylalkyl, $C_1$-$C_6$ alkoxyalkyl, substituted $C_1$-$C_6$ alkoxyalkyl, alkylsulfonylalkyl, aminoalkyl, monoalkylaminoalkyl or dialkylaminoalkyl.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to a mammal in need thereof. Accordingly, in another embodiment, pharmaceutical compositions are disclosed containing one or more CRF receptor antagonists of this invention in combination with a pharmaceutically acceptable carrier and/or diluent.

As used herein, the above terms have the following meaning:

"Alkyl" means a straight chain or branched, noncyclic or cyclic, unsaturated or saturated aliphatic hydrocarbon containing from 1 to 10 carbon atoms, while the terms "lower alkyl" and "$C_1$-$C_6$ alkyl" have the same meaning as alkyl but contain 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$-cyclopropyl, —CH$_2$-cyclobutyl, —CH$_2$-cyclopentyl, —CH$_2$-cyclohexyl, and the like; while unsaturated cyclic alkyls include cyclopentenyl and cyclohexenyl, and the like. Cyclic alkyls, also referred to as "homocyclic rings," include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atom replaced with an aryl moiety, such as benzyl (i.e., —CH$_2$-phenyl), —CH$_2$-(1- or 2-naphthyl), —(CH$_2$)$_2$-phenyl, —(CH$_2$)$_3$-phenyl, —CH(phenyl)$_2$, and the like.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl and oxadiazolyl.

"Heteroarylalkyl" means an alkyl having at least one alkyl hydrogen atom replaced with a heteroaryl moiety, such as —CH$_2$-pyridinyl, —CH$_2$-pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocycle rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, piperizinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —$CH_2$-morpholinyl, and the like.

"Haloalkyl" means an alkyl group having at least one alkyl hydrogen atom replaced with a halogen, such as $CH_2Cl$, $CHCl_2$, $CCl_3$, $CH_2F$, $CF_3$, and the like. "$C_1$-$C_6$ haloalkyl" has the same definition as "haloalkyl" but contains 1 to 6 carbon atoms.

The term "substituted" as used herein means that at least one hydrogen atom on any of the groups described herein (e.g., alkyl, alkoxy, alkoxyalkyl, aryl, arylalkyl, heteroaryl, heteroarylalkyl, heterocycle or heterocyclealkyl) is replaced with a substituent. In the case of an oxo substituent ("(=O)") two hydrogen atoms are replaced. "Substituents" within the context of this invention include halogen, hydroxy, cyano, nitro, amino, alkylamino, dialkylamino, alkyl, substituted alkyl, alkoxy, thioalkyl, haloalkyl, hydroxyalkyl, alkoxyalkyl, haloalkoxy, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —$NR_aR_b$, —$NR_aC(=O)R_b$, —$NR_aC(=O)NR_aR_b$, —$NR_aC(=O)OR_b$—$NR_aSO_2R_b$, —$OR_a$, —$C(=O)R_a$ —$C(=O)OR_a$, —$C(=O)NR_aR_b$, —$OC(=O)NR_aR_b$, —SH, —$SR_a$, —$S(=O)R_a$, —$S(=O)_2R_a$, —$OS(=O)_2R_a$, —$S(=O)_2OR_a$, wherein $R_a$ and $R_b$ are the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

"Halogen" means fluoro, chloro, bromo or iodo.

"Alkoxy" means an alkyl moiety attached through an oxygen bridge (i.e., —O-alkyl) such as —O-methyl, —O-ethyl, and the like. "$C_1$-$C_6$ alkoxy" has the same definition as alkoxy but contains 1 to 6 carbon atoms.

"Haloalkoxy" means an alkoxy having at least one hydrogen atom replaced with halogen, such as trifluoromethoxy and the like.

"Alkoxyalkyl" means an alkyl having at least one hydrogen atom replaced with alkoxy, such as methoxymethyl and the like. "$C_1$-$C_6$ alkoxyalkyl" has the same definition as "alkoxyalkyl" where the alkoxy group has 1 to 6 carbon atoms.

"Thioalkyl" means an alkyl moiety attached through a sulfur bridge (i.e., —S-alkyl) such as —S-methyl, —S-ethyl, and the like.

"Alkylamino" and "dialkylamino" mean one or two alkyl moieties attached through a nitrogen bridge (i.e., —NHalkyl or —N(alkyl)(alkyl)) such as methylamino, ethylamino, dimethylamino, diethylamino, and the like.

"Hydroxyalkyl" means an alkyl substituted with at least one hydroxyl group.

"Mono- or di(cycloalkyl)methyl" represents a methyl group substituted with one or two cycloalkyl groups, such as cyclopropylmethyl, dicyclopropylmethyl, and the like.

"Alkylcarbonylalkyl" represents an alkyl substituted with a —C(=O)alkyl group.

"Alkylcarbonyloxyalkyl" represents an alkyl substituted with a —C(=O)Oalkyl group or a —OC(=O)alkyl group.

"Alkylthioalkyl" represents a alkyl substituted with a —S-alkyl group.

"Mono- or di(alkyl)aminoalkyl" represents an alkyl substituted with a mono- or di(alkyl)amino.

"Acyl" represents alkyl-C(=O)—.

Embodiments of the invention presented herein are for purposes of example and not for purposes of limitation. In one embodiment of this invention, $R_1$ may represent hydrogen, alkyl, substituted alkyl, haloalkyl, substituted haloalkyl, alkoxyalkyl, substituted alkoxyalkyl, arylalkyl, substituted arylalkyl, heterocyclealkyl, or substituted heterocyclealkyl. Thus, representative compounds of this invention include, for example, the following structure (IIa) where $R_1$ is hydrogen, structure (IIb) where $R_1$ is methyl, structure (IIc) where $R_1$ is methoxymethyl, structure (IId) where $R_1$ is benzyl, and structure (IIe) where $R_1$ is pyrid-2-yl-methyl:

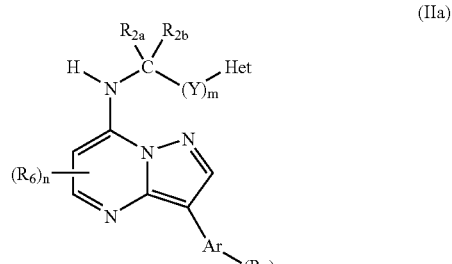

(IIa)

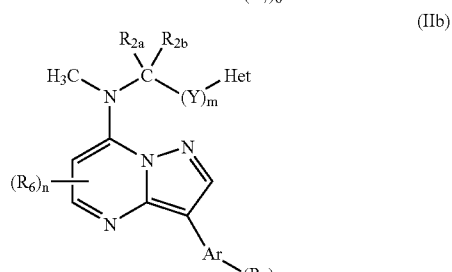

(IIb)

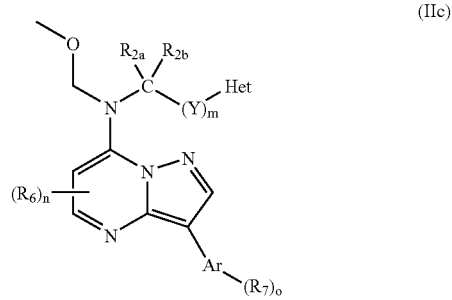

(IIc)

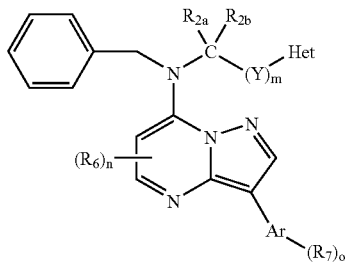

(IId)

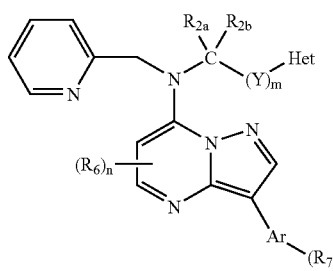

(IIe)

In further embodiments of the invention, $R_{2a}$ and $R_{2b}$ are independently hydrogen, $C_1$-$C_6$ alkyl, substituted $C_1$-$C_6$ alkyl, $C_1$-$C_6$ haloalkyl, substituted $C_1$-$C_6$ haloalkyl, arylalkyl, substituted arylalkyl, $C_1$-$C_6$ alkoxyalkyl, substituted $C_1$-$C_6$ alkoxyalkyl, alkylsulfonylalkyl, aminoalkyl, monoalkylaminoalkyl or dialkylaminoalkyl. Thus, representative compounds of this invention include the following structure (IIIa) where $R_{2a}$ and $R_{2b}$ are hydrogen. Further representative compounds wherein $R_{2b}$ is hydrogen include structure (IIIb) where $R_{2a}$ is alkyl exemplified by methyl, structure (IIIc) where $R_{2a}$ is arylalkyl exemplified by benzyl, structure (IIId) where $R_{2a}$ is alkoxyalkyl exemplified by methoxymethyl, structure (IIIe) where $R_{2a}$ is alkylsulfonylalkyl exemplified by methylsulfonylmethyl, and structure (IIIf) where $R_{2a}$ is aminoalkyl exemplified by aminomethyl.

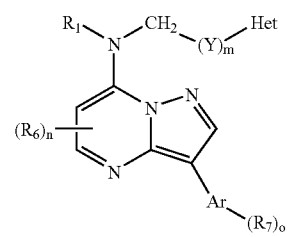

(IIIa)

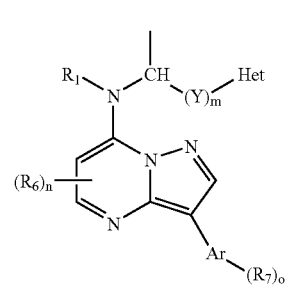

(IIIb)

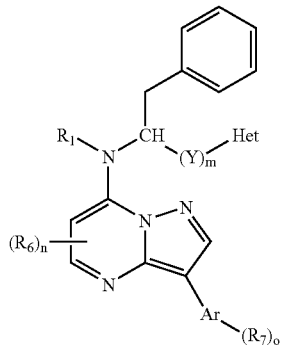

(IIIc)

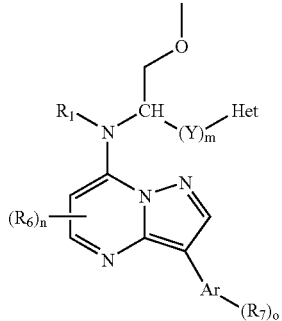

(IIId)

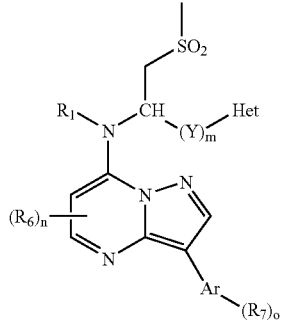

(IIIe)

(IIIf)

In further embodiments of the invention, $R_1$ together with the nitrogen to which it is attached and either $R_{2a}$ or $R_{2b}$ together with the carbon to which $R_{2a}$ and $R_{2b}$ are attached form a 4-7 membered heterocyclic ring exemplified in structure (IVa) as the 7-pyrrolidin-1-yl-pyrazolo[1,5-a]pyrimidine and in structure (IVb) as the 7-piperidin-1-yl-pyrazolo[1,5-a]pyrimidine.

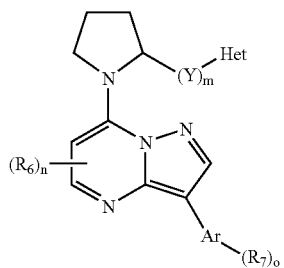

(IVa)

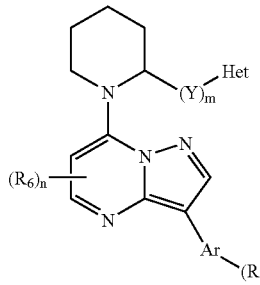

(IVb)

In further embodiments of the invention, $R_{2a}$ and $R_{2b}$ together with the carbon atom to which they are attached form a ring of 3-7 members exemplied by cyclopropyl in the following structure (Va) and by ring "A" in the following structure (Vb) wherein ring "A" optionally contains —O—, —S— or —N($R_3$)— and $R_3$ is alkyl, substituted alkyl, aryalkyl, substituted arylalkyl, acyl, —C(O)O$R_8$, —C(O)N$R_9R_{10}$, or S(O)$_2R_{11}$.

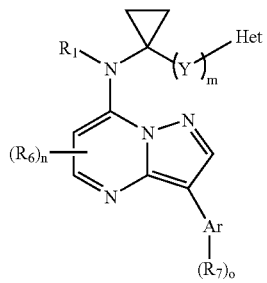

(Va)

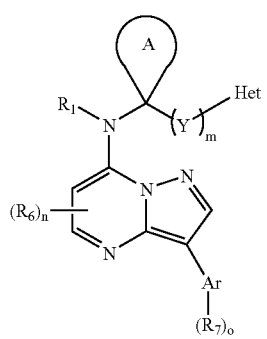

(Vb)

In further embodiments of the invention, Y at each occurrence is independently a direct bond or —C($R_{4a}R_{4b}$)$_m$—, where m is 1-2 inclusive and $R_{4a}$ and $R_{4b}$ are independently hydrogen, $C_1$-$C_6$ alkyl, substituted $C_1$-$C_6$ alkyl, arylalkyl, substituted arylalkyl, $C_1$-$C_6$ alkoxyalkyl, substituted $C_1$-$C_6$ alkoxyalkyl, alkylsulfonylalkyl, aminoalkyl, monoalkylaminoalkyl or dialkylaminoalkyl. Thus, representative compounds of this invention include for example the following structure (VIa) when Y is a direct bond and structure (VIb) when Y is —C($R_{4a}R_{4b}$)$_m$— and m is 1.

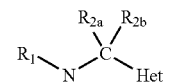

(VIa)

(VIb)

In another embodiment of the invention, $R_{4a}$ and $R_{4b}$ together with the carbon atom to which they are attached form a ring of 3-7 members optionally containing within the ring —O—, —S— or —N($R_3$)—. Thus, representative compounds of this invention include for example the following structure (VIIa) when $R_{4a}$ and $R_{4b}$ together with the carbon atom to which they are attached form a cyclopropyl ring, and structure (VIIb) when $R_{4a}$ and $R_{4b}$ together with the carbon atom to which they are attached form ring "B" wherein ring "B" optionally contains —O—, —S— or —N($R_3$)—.

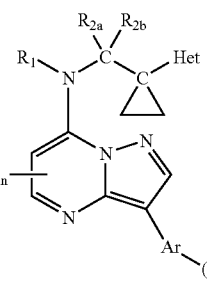

(VIIa)

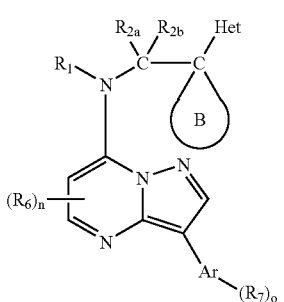

(VIIb)

In another embodiment of the invention, Het is one of three oxadiazoles exemplified in the following structures (VIIIa)-(VIIIc) wherein R5 is hydrogen, halogen, $C_1$-$C_6$ alkyl, substituted $C_1$-$C_6$ alkyl, $C_1$-$C_6$ alkoxy, substituted $C_1$-$C_6$ alkoxy, amino, alkylamino or dialkylamino.

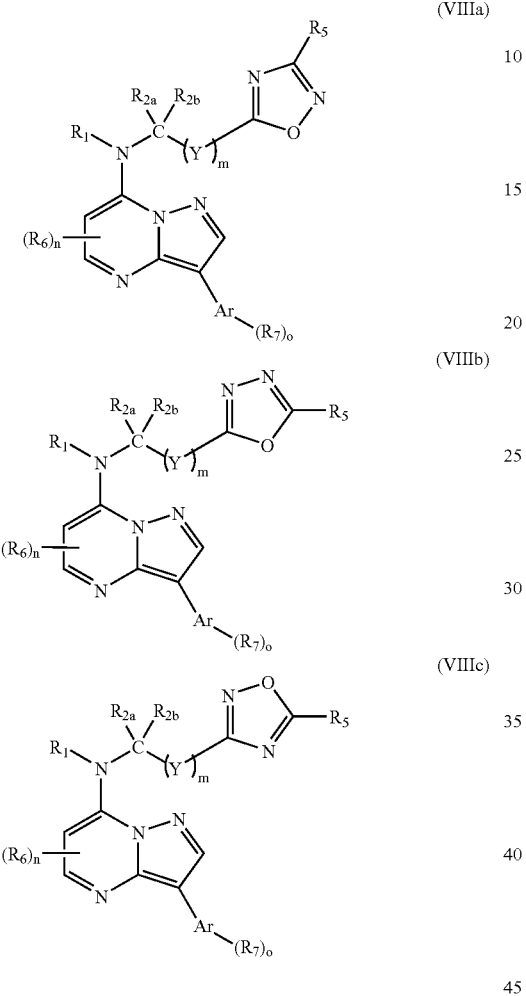

In another embodiment of the invention, $R_6$ at each occurrence is independently independently halogen, $C_1$-$C_6$ alkyl or substituted $C_1$-$C_6$ alkyl, and n is 0-3 inclusive. Thus, representative compounds of this invention include for example the following structures (IXa-IXh) wherein $R_6$ independently occupies all possible combinations of positions 2, 5 and 6 of the pyrazolo-[1,5a]-pyrimidines core:

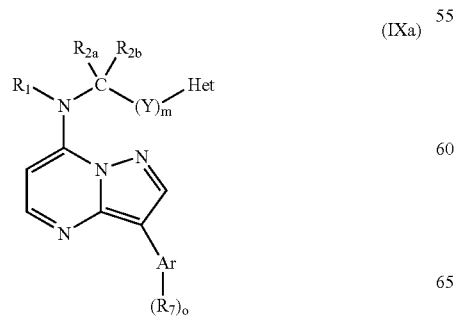

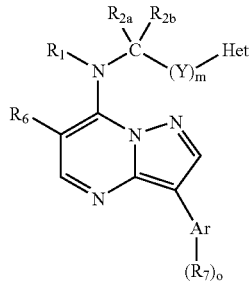

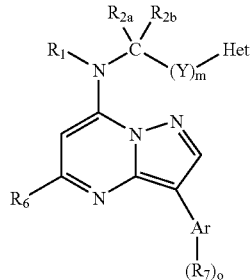

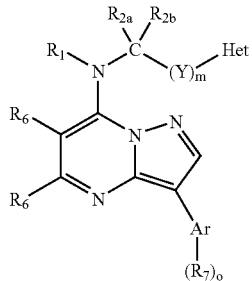

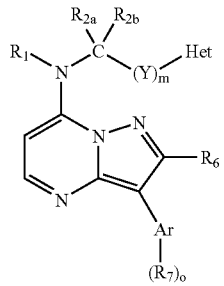

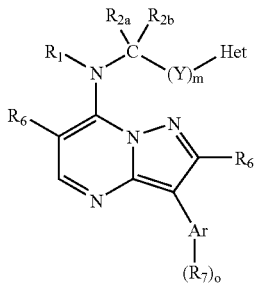

-continued

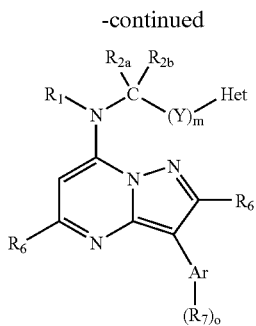
(IXg)

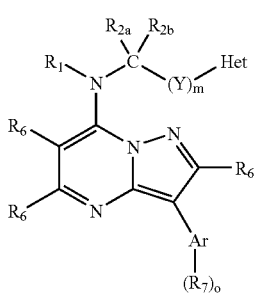
(IXh)

In another embodiment of the invention, Ar is phenyl or pyridyl, $R_7$ at each occurrence is independently halogen, $C_1$-$C_{10}$ alkyl, substituted $C_1$-$C_{10}$ alkyl, $C_1$-$C_6$ alkoxy, substituted $C_1$-$C_6$ alkoxy, —$NR_9R_{10}$, alkylsulfonyl or substituted alkylsulfonyl, and o is 0-3 inclusive. Thus, representative compounds of the invention include for example the following structure (Xa) when Ar is phenyl and structure (Xb) when Ar is pyridyl.

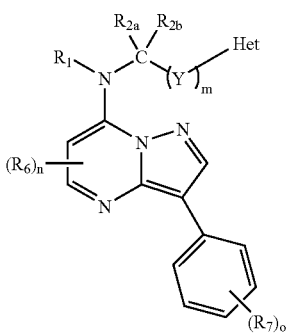
(Xa)

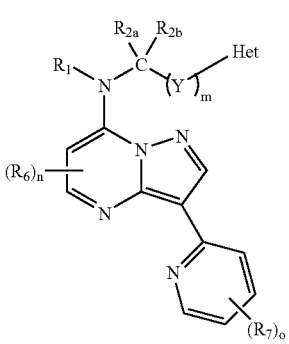
(Xb)

Compounds of the present invention include:
[1-(3-Cyclopropyl-[1,2,4]oxadiazol-5-yl)-propyl]-[3-(4-methoxy-2-methyl-phenyl)-2,5-dimethyl-pyrazolo[1,5-a]pyrimidin-7-yl]-amine (Ex. 11-1);
[1-(3-Isopropyl-[1,2,4]oxadiazol-5-yl)-propyl]-[3-(4-methoxy-2-methyl-phenyl)-2,5-dimethyl-pyrazolo[1,5-a]pyrimidin-7-yl]-amine (Ex. 11-2);
[3-(4-Methoxy-2-methyl-phenyl)-2,5-dimethyl-pyrazolo[1,5-a]pyrimidin-7-yl]-[1-(3-methyl-[1,2,4]oxadiazol-5-yl)-2-phenyl-ethyl]-amine (Ex. 11-3);
[1-(3-Isopropyl-[1,2,4]oxadiazol-5-yl)-propyl]-[3-(4-methoxy-2-methyl-phenyl)-2,5-dimethyl-pyrazolo[1,5-a]pyrimidin-7-yl]-amine (Ex. 11-4);
[3-(4-Methoxy-2-methyl-phenyl)-2,5-dimethyl-pyrazolo[1,5-a]pyrimidin-7-yl]-[1-(3-methyl-[1,2,4]oxadiazol-5-yl)-butyl]-amine (Ex. 11-5);
[3-(4-Methoxy-2-methyl-phenyl)-2,5-dimethyl-pyrazolo[1,5-a]pyrimidin-7-yl]-(3-methyl-[1,2,4]oxadiazol-5-ylmethyl)-amine (Ex. 11-6);
(3-Cyclopropyl-[1,2,4]oxadiazol-5-ylmethyl)-[3-(4-methoxy-2-methyl-phenyl)-2,5-dimethyl-pyrazolo[1,5-a]pyrimidin-7-yl]-amine (Ex. 11-7);
(3-Isopropyl-[1,2,4]oxadiazol-5-ylmethyl)-[3-(4-methoxy-2-methyl-phenyl)-2,5-dimethyl-pyrazolo[1,5-a]pyrimidin-7-yl]-amine (Ex. 11-8);
[2-(3-Cyclopropyl-[1,2,4]oxadiazol-5-yl)-(R)-1-methyl-ethyl]-[3-(4-methoxy-2-methyl-phenyl)-2,5-dimethyl-pyrazolo[1,5-a]pyrimidin-7-yl]-amine (Ex. 11-9);
[3-(4-Methoxy-2-methyl-phenyl)-2,5-dimethyl-pyrazolo[1,5-a]pyrimidin-7-yl]-[(R)-1-methyl-2-(3-methyl-[1,2,4]oxadiazol-5-yl)-ethyl]-amine (Ex. 11-10);
[3-(4-Methoxy-2-methyl-phenyl)-2,5-dimethyl-pyrazolo[1,5-a]pyrimidin-7-yl]-[1-(3-trifluoromethyl-[1,2,4]oxadiazol-5-yl)-propyl]-amine (Ex. 11-11);
[1-(3-Cyclopropyl-[1,2,4]oxadiazol-5-yl)-cyclopropyl]-[3-(4-methoxy-2-methyl-phenyl)-2,5-dimethyl-pyrazolo[1,5-a]pyrimidin-7-yl]-amine (Ex. 11-12);
[3-(4-Methoxy-2-methyl-phenyl)-2,5-dimethyl-pyrazolo[1,5-a]pyrimidin-7-yl]-[1-(3-methyl-[1,2,4]oxadiazol-5-yl)-cyclopropyl]-amine (Ex. 11-13);
[1-(3-Ethyl-[1,2,4]oxadiazol-5-yl)-cyclopropyl]-[3-(4-methoxy-2-methyl-phenyl)-2,5-dimethyl-pyrazolo[1,5-a]pyrimidin-7-yl]-amine (Ex. 11-14);
[3-(4-Methoxy-2-methyl-phenyl)-2,5-dimethyl-pyrazolo[1,5-a]pyrimidin-7-yl]-(3-propyl-[1,2,4]oxadiazol-5-ylmethyl)-amine (Ex. 11-15);
[3-(4-Methoxy-2-methyl-phenyl)-2,5-dimethyl-pyrazolo[1,5-a]pyrimidin-7-yl]-[1-(3-trifluoromethyl-[1,2,4]oxadiazol-5-yl)-cyclopropyl]-amine (Ex. 11-16);
[2-(3-Ethyl-[1,2,4]oxadiazol-5-yl)-(R)-1-methyl-ethyl]-[3-(4-methoxy-2-methyl-phenyl)-2,5-dimethyl-pyrazolo[1,5-a]pyrimidin-7-yl]-amine (Ex. 11-17);
[3-(6-Dimethylamino-4-methyl-pyridin-3-yl)-2,5-dimethyl-pyrazolo[1,5-a]pyrimidin-7-yl]-[3-methyl-(R)-1-(3-methyl-[1,2,4]oxadiazol-5-yl)-butyl]-amine (Ex. 11-18);
3-(2,4-Dimethoxy-phenyl)-2,5-dimethyl-7-[(S)-2-(3-methyl-[1,2,4]oxadiazol-5-yl)-pyrrolidin-1-yl]-pyrazolo[1,5-a]pyrimidine (Ex. 11-19);
[3-(2,4-Dimethoxy-phenyl)-2,5-dimethyl-pyrazolo[1,5-a]pyrimidin-7-yl]-[1-(3-methyl-[1,2,4]oxadiazol-5-yl)-propyl]-amine (Ex. 11-20);
[3-(2,4-Dimethoxy-phenyl)-2,5-dimethyl-pyrazolo[1,5-a]pyrimidin-7-yl]-[1-(3-methyl-[1,2,4]oxadiazol-5-yl)-ethyl]-amine (Ex. 11-21);
[3-(2,4-Dimethoxy-phenyl)-2,5-dimethyl-pyrazolo[1,5-a]pyrimidin-7-yl]-[1-(3-methyl-[1,2,4]oxadiazol-5-yl)-butyl]-amine (Ex. 11-22);

[3-(2,4-Dimethoxy-phenyl)-2,5-dimethyl-pyrazolo[1,5-a]
  pyrimidin-7-yl]-[3-methyl-1-(3-methyl-[1,2,4]oxadiazol-
  5-yl)-butyl]-amine (Ex. 11-23);
[3-(2,4-Dimethoxy-phenyl)-2,5-dimethyl-pyrazolo[1,5-a]
  pyrimidin-7-yl]-methyl-(3-methyl-[1,2,4]oxadiazol-5-yl-
  methyl)-amine (Ex. 11-24);
Benzyl-[3-(6-dimethylamino-4-methyl-pyridin-3-yl)-2,5-
  dimethyl-pyrazolo[1,5-a]pyrimidin-7-yl]-(3-methyl-[1,2,
  4]oxadiazol-5-ylmethyl)-amine (Ex. 11-25);
[3-(4-Methoxy-2-methyl-phenyl)-2,5-dimethyl-pyrazolo[1,
  5-a]pyrimidin-7-yl]-[1-(3-methyl-[1,2,4]oxadiazol-5-yl)-
  propyl]-amine (Ex. 11-26);
[3-(4-Methoxy-2-methyl-phenyl)-2,5-dimethyl-pyrazolo[1,
  5-a]pyrimidin-7-yl]-[1-methyl-2-(3-methyl-[1,2,4]oxa-
  diazol-5-yl)-ethyl]-amine (Ex. 12-1);
Benzyl-[3-(4-methoxy-2-methyl-phenyl)-2,5-dimethyl-
  pyrazolo[1,5-a]pyrimidin-7-yl]-(3-methyl-[1,2,4]oxadia-
  zol-5-ylmethyl)-amine (Ex. 12-2);
[3-(4-Methoxy-2-methyl-phenyl)-2,5-dimethyl-pyrazolo[1,
  5-a]pyrimidin-7-yl]-[2,2,2-trifluoro-1-(3-methyl-[1,2,4]
  oxadiazol-5-ylmethyl)-ethyl]-amine (Ex. 12-3);
[2-(3-Cyclopropyl-[1,2,4]oxadiazol-5-yl)-1-methyl-ethyl]-
  [3-(4-methoxy-2-methyl-phenyl)-2,5-dimethyl-pyrazolo
  [1,5-a]pyrimidin-7-yl]-amine (Ex. 12-4);
[2-(3-Isopropyl-[1,2,4]oxadiazol-5-yl)-1-methyl-ethyl]-[3-
  (4-methoxy-2-methyl-phenyl)-2,5-dimethyl-pyrazolo[1,
  5-a]pyrimidin-7-yl]-amine (Ex. 12-5);
[2-(3-Cyclopropyl-[1,2,4]oxadiazol-5-yl)-(S)-1-methyl-
  ethyl]-[3-(4-methoxy-2-methyl-phenyl)-2,5-dimethyl-
  pyrazolo[1,5-a]pyrimidin-7-yl]-amine (Ex. 12-6);
[2-(3-Isopropyl-[1,2,4]oxadiazol-5-yl)-(S)-1-methyl-ethyl]-
  [3-(4-methoxy-2-methyl-phenyl)-2,5-dimethyl-pyrazolo
  [1,5-a]pyrimidin-7-yl]-amine (Ex. 12-7);
[3-(4-Methoxy-2-methyl-phenyl)-2,5-dimethyl-pyrazolo[1,
  5-a]pyrimidin-7-yl]-[(S)-1-methyl-2-(3-methyl-[1,2,4]
  oxadiazol-5-yl)-ethyl]-amine (Ex. 12-8);
[3-(4-Methoxy-2-methyl-phenyl)-2,5-dimethyl-pyrazolo[1,
  5-a]pyrimidin-7-yl]-[1-(3-methyl-[1,2,4]oxadiazol-5-yl-
  methyl)-propyl]-amine (Ex. 12-9);
[1-(3-Cyclopropyl-[1,2,4]oxadiazol-5-ylmethyl)-propyl]-
  [3-(2,4-dimethoxy-phenyl)-2,5-dimethyl-pyrazolo[1,5-a]
  pyrimidin-7-yl]-amine (Ex. 12-10);
[3-(2,4-Dimethoxy-phenyl)-2,5-dimethyl-pyrazolo[1,5-a]
  pyrimidin-7-yl]-[1-(3-methyl-[1,2,4]oxadiazol-5-ylm-
  ethyl)-propyl]-amine (Ex. 12-11);
[3-(4-Methoxy-2-methyl-phenyl)-2,5-dimethyl-pyrazolo[1,
  5-a]pyrimidin-7-yl]-[(S)-1-(3-methyl-[1,2,4]oxadiazol-5-
  yl)-butyl]-amine (Ex. 13-1);
[3-(4-Methoxy-2-methyl-phenyl)-2,5-dimethyl-pyrazolo[1,
  5-a]pyrimidin-7-yl]-[2,2,2-trifluoro-(S)-1-(3-methyl-[1,2,
  4]oxadiazol-5-ylmethyl)-ethyl]-amine (Ex. 13-2);
[3-(4-Methoxy-2-methyl-phenyl)-2,5-dimethyl-pyrazolo[1,
  5-a]pyrimidin-7-yl]-[1-methyl-2-(3-trifluoromethyl-[1,2,
  4]oxadiazol-5-yl)-ethyl]-amine (Ex. 13-3);
[3-(2-Chloro-4-methoxy-phenyl)-2,5-dimethyl-pyrazolo[1,
  5-a]pyrimidin-7-yl]-[2,2,2-trifluoro-(S)-1-(3-methyl-[1,2,
  4]oxadiazol-5-ylmethyl)-ethyl]-amine (Ex. 13-4);
[3-(4-Methoxy-2-methyl-phenyl)-2,5-dimethyl-pyrazolo[1,
  5-a]pyrimidin-7-yl]-[(R)-1-methyl-2-(3-trifluoromethyl-
  [1,2,4]oxadiazol-5-yl)-ethyl]-amine (Ex. 13-5);
[3-(2-Chloro-4-methoxy-phenyl)-2,5-dimethyl-pyrazolo[1,
  5-a]pyrimidin-7-yl]-[(R)-1-methyl-2-(3-trifluoromethyl-
  [1,2,4]oxadiazol-5-ylmethyl)-ethyl]-amine (Ex. 13-6);
[3-(2,4-Dimethoxy-phenyl)-2,5-dimethyl-pyrazolo[1,5-a]
  pyrimidin-7-yl]-[(R)-1-methyl-2-(3-trifluoromethyl-[1,2,
  4]oxadiazol-5-yl)-ethyl]-amine (Ex. 13-7);
[3-(2,4-Dimethoxy-phenyl)-2,5-dimethyl-pyrazolo[1,5-a]
  pyrimidin-7-yl]-[2,2,2-trifluoro-(S)-1-(3-methyl-[1,2,4]
  oxadiazol-5-ylmethyl)-ethyl]-amine (Ex. 13-8);
[3-(2,4-Dimethoxy-phenyl)-2,5-dimethyl-pyrazolo[1,5-a]
  pyrimidin-7-yl]-[2,2,2-trifluoro-(S)-1-(3-trifluoromethyl-
  [1,2,4]oxadiazol-5-ylmethyl)-ethyl]-amine (Ex. 13-9);
[3-(4-Methoxy-2-methyl-phenyl)-2,5-dimethyl-pyrazolo[1,
  5-a]pyrimidin-7-yl]-[(S)-1-(3-methyl-[1,2,4]oxadiazol-5-
  yl)-propyl]-amine (Ex. 14-1);
[3-(4-Methoxy-2-methyl-phenyl)-2,5-dimethyl-pyrazolo[1,
  5-a]pyrimidin-7-yl]-[(R)-1-(3-methyl-[1,2,4]oxadiazol-5-
  yl)-propyl]-amine (Ex. 14-2);
3-(4-Methoxy-2-methyl-phenyl)-2,5-dimethyl-7-[(S)-2-(3-
  methyl-[1,2,4]oxadiazol-5-ylmethyl)-pyrrolidin-1-yl]-
  pyrazolo[1,5-a]pyrimidine (Ex. 14-3);
[3-(2-Chloro-4-methoxy-phenyl)-2,5-dimethyl-pyrazolo[1,
  5-a]pyrimidin-7-yl]-[(S)-1-(3-methyl-[1,2,4]oxadiazol-5-
  yl)-propyl]-amine (Ex. 14-4);
[3-(2,4-Dimethoxy-phenyl)-2,5-dimethyl-pyrazolo[1,5-a]
  pyrimidin-7-yl]-(2-methoxy-ethyl)-(3-methyl-[1,2,4]oxa-
  diazol-5-ylmethyl)-amine (Ex. 15-1);
(5-{2,5-Dimethyl-7-[(S)-2-(3-methyl-[1,2,4]oxadiazol-5-
  yl)-pyrrolidin-1-yl]-pyrazolo[1,5-a]pyrimidin-3-yl}-4-
  methyl-pyridin-2-yl)-dimethyl-amine (Ex. 15-2);
[3-(6-Dimethylamino-4-methyl-pyridin-3-yl)-2,5-dimethyl-
  pyrazolo[1,5-a]pyrimidin-7-yl]-(2-methoxy-ethyl)-(3-
  methyl-[1,2,4]oxadiazol-5-ylmethyl)-amine (Ex. 15-3);
[3-(4-Ethoxy-phenyl)-2,5-dimethyl-pyrazolo[1,5-a]pyrimi-
  din-7-yl]-(2-methoxy-ethyl)-(3-methyl-[1,2,4]oxadiazol-
  5-ylmethyl)-amine (Ex. 15-4);
[3-(2,4-Dimethoxy-phenyl)-2,5-dimethyl-pyrazolo[1,5-a]
  pyrimidin-7-yl]-(2-methoxy-ethyl)-[3-(3-methyl-[1,2,4]
  oxadiazol-5-yl)-propyl]-amine (Ex. 16-1);
[3-(4-Methoxy-2-methyl-phenyl)-2,5-dimethyl-pyrazolo[1,
  5-a]pyrimidin-7-yl]-[(R)-1-methyl-2-(5-methyl-[1,2,4]
  oxadiazol-3-yl)-ethyl]-amine (Ex. 17-1);
[3-(4-Methoxy-2-methyl-phenyl)-2,5-dimethyl-pyrazolo[1,
  5-a]pyrimidin-7-yl]-[(S)-1-(5-methyl-[1,2,4]oxadiazol-3-
  ylmethyl)-propyl]-amine (Ex. 17-2);
[3-(4-Methoxy-2-methyl-phenyl)-2,5-dimethyl-pyrazolo[1,
  5-a]pyrimidin-7-yl]-[(R)-1-(5-methyl-[1,2,4]oxadiazol-3-
  ylmethyl)-propyl]-amine (Ex. 17-3);
[3-(4-Methoxy-2-methyl-phenyl)-2,5-dimethyl-pyrazolo[1,
  5-a]pyrimidin-7-yl]-[(S)-1-methyl-2-(5-methyl-[1,2,4]
  oxadiazol-3-yl)-ethyl]-amine (Ex. 17-4);
[(R)-2-(5-Cyclopropyl-[1,2,4]oxadiazol-3-yl)-1-methyl-
  ethyl]-[3-(4-methoxy-2-methyl-phenyl)-2,5-dimethyl-
  pyrazolo[1,5-a]pyrimidin-7-yl]-amine (Ex. 18-1);
[3-(4-Methoxy-2-methyl-phenyl)-2,5-dimethyl-pyrazolo[1,
  5-a]pyrimidin-7-yl]-[(R)-1-methyl-2-(5-trifluoromethyl-
  [1,2,4]oxadiazol-3-yl)-ethyl]-amine (Ex. 18-2);
[3-(4-Methoxy-2-methyl-phenyl)-2,5-dimethyl-pyrazolo[1,
  5-a]pyrimidin-7-yl]-[(S)-2,2,2-trifluoro-1-(5-methyl-[1,2,
  4]oxadiazol-3-ylmethyl)-ethyl]-amine (Ex. 19-1);
Ethyl-[3-(4-methoxy-2-methyl-phenyl)-2,5-dimethyl-pyra-
  zolo[1,5-a]pyrimidin-7-yl]-(3-methyl-[1,2,4]oxadiazol-5-
  ylmethyl)-amine (Ex. 20-1);
3-(4-Methoxy-2-methyl-phenyl)-2,5-dimethyl-7-[2-(3-me-
  thyl-[1,2,4]oxadiazol-5-ylmethyl)-piperidin-1-yl]-pyra-
  zolo[1,5-a]pyrimidine (Ex. 20-2);
[3-(4-Methoxy-2-methyl-phenyl)-2,5-dimethyl-pyrazolo[1,
  5-a]pyrimidin-7-yl]-(1-[1,3,4]oxadiazol-2-yl-propyl)-
  amine (Ex. 21-1);
[3-(4-Methoxy-2-methyl-phenyl)-2,5-dimethyl-pyrazolo[1,
  5-a]pyrimidin-7-yl]-[1-(5-methyl-[1,3,4]oxadiazol-2-yl)-
  propyl]-amine (Ex. 22-1);

[3-(4-Methoxy-2-methyl-phenyl)-2,5-dimethyl-pyrazolo[1,5-a]pyrimidin-7-yl]-[1-methyl-2-(5-methyl-[1,3,4]oxadiazol-2-yl)-ethyl]-amine (Ex. 23-1);

[3-(4-Methoxy-2-methyl-phenyl)-2,5-dimethyl-pyrazolo[1,5-a]pyrimidin-7-yl]-[1-methyl-2-(5-trifluoromethyl-[1,3,4]oxadiazol-2-yl)-ethyl]-amine (Ex. 23-2);

[3-(2-Chloro-4-methoxy-phenyl)-2,5-dimethyl-pyrazolo[1,5-a]pyrimidin-7-yl]-[1-(3-methyl-[1,2,4]oxadiazol-5-yl)-propyl]-amine (Ex. 24-1);

[3-(4-Chloro-2-methoxy-phenyl)-2,5-dimethyl-pyrazolo[1,5-a]pyrimidin-7-yl]-[1-(3-methyl-[1,2,4]oxadiazol-5-yl)-propyl]-amine (Ex. 24-2);

[3-(3-Chloro-4-fluoro-phenyl)-2,5-dimethyl-pyrazolo[1,5-a]pyrimidin-7-yl]-[1-(3-methyl-[1,2,4]oxadiazol-5-yl)-propyl]-amine (Ex. 24-3);

[3-(4-Chloro-2-methyl-phenyl)-2,5-dimethyl-pyrazolo[1,5-a]pyrimidin-7-yl]-[1-(3-methyl-[1,2,4]oxadiazol-5-yl)-propyl]-amine (Ex. 24-4);

[3-(2-Chloro-4-trifluoromethyl-phenyl)-2,5-dimethyl-pyrazolo[1,5-a]pyrimidin-7-yl]-[1-(3-methyl-[1,2,4]oxadiazol-5-yl)-propyl]-amine (Ex. 24-5); and

[3-(2-Chloro-4-methyl-phenyl)-2,5-dimethyl-pyrazolo[1,5-a]pyrimidin-7-yl]-[1-(3-methyl-[1,2,4]oxadiazol-5-yl)-propyl]-amine (Ex. 24-6).

Figure 4:
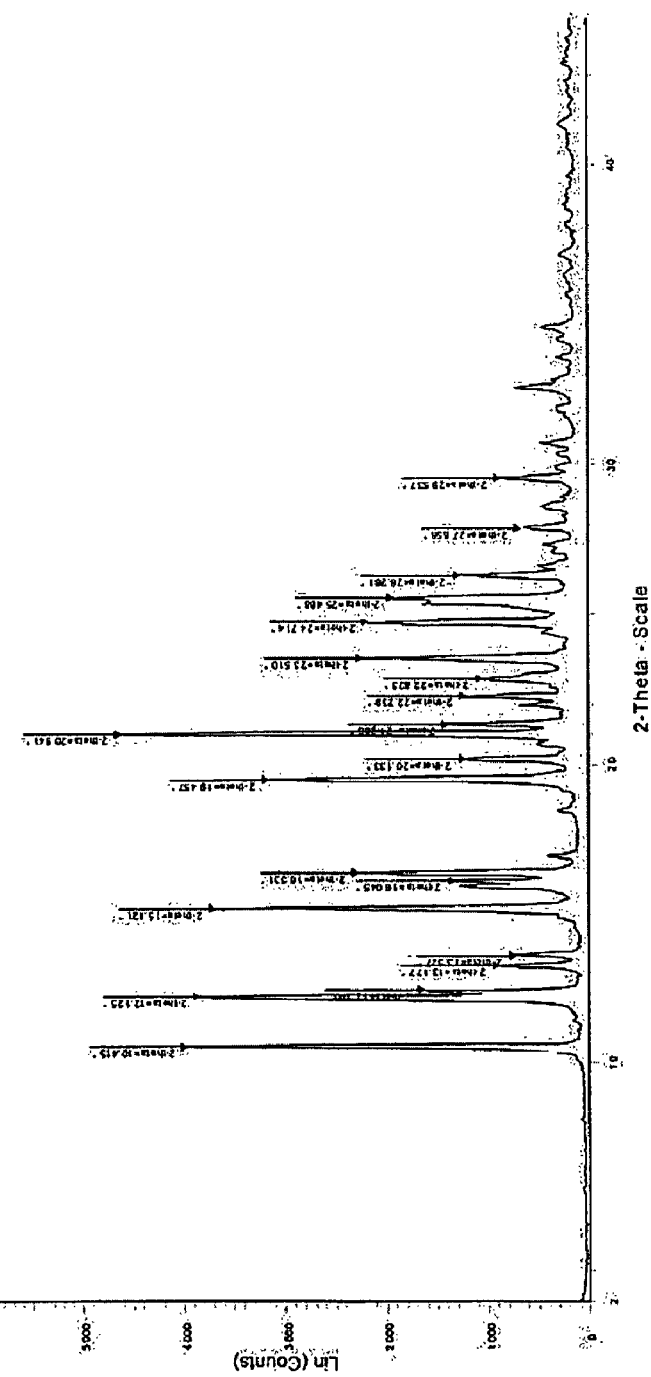
FIG. 4 shows X-Ray powder diffraction data obtained for polymorph Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine as described before. Form 1 is characterised by having an XRPD pattern with signals substantially as listed in Table 1.
Figure 6:
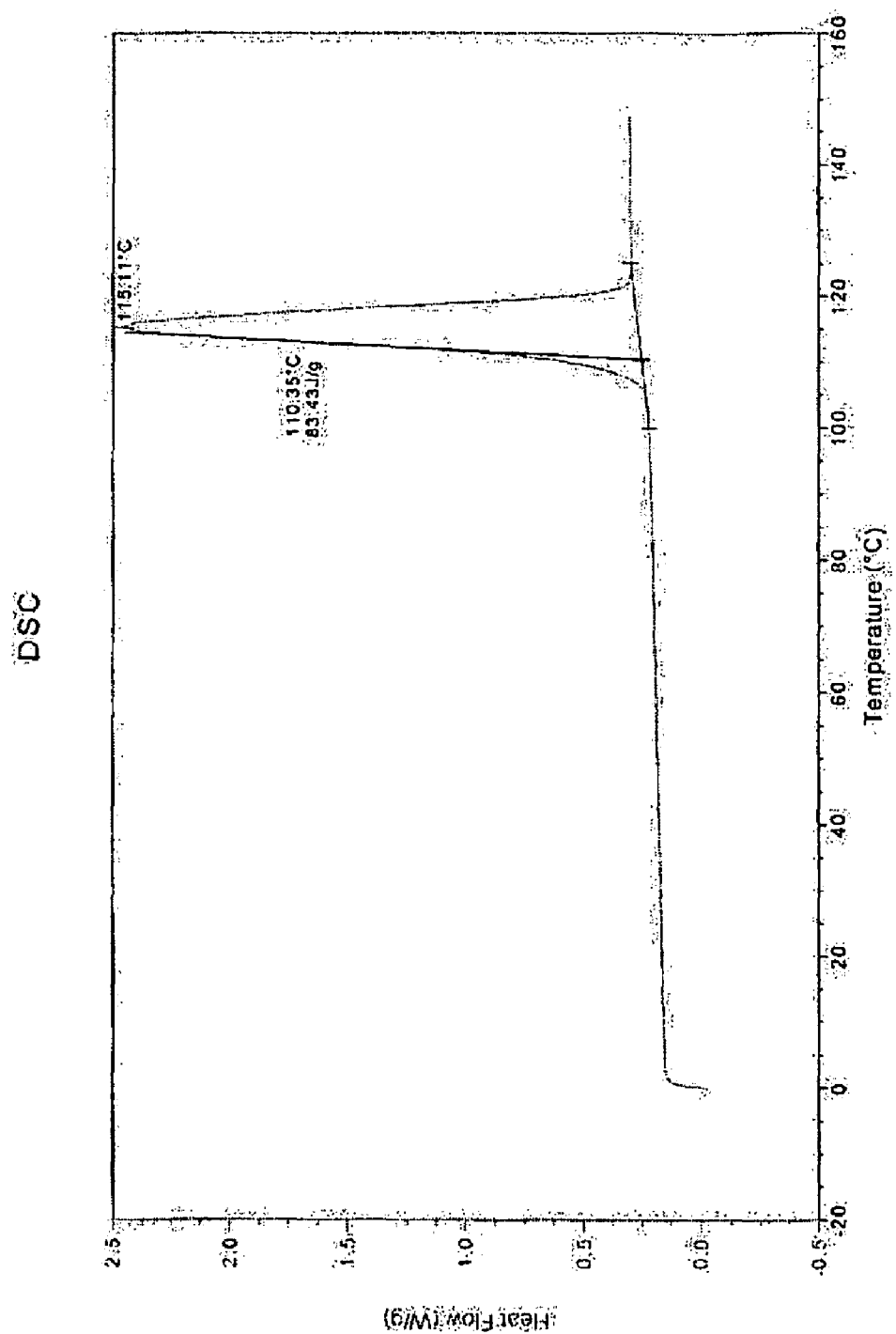
FIG. 6 shows a Differential Scanning Calorimetry (DSC) thermogram of polymorph Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

In another embodiment of the present invention, polymorphs of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine (Example 14-1) are reported. Polymorph Form 1 exhibits a predominant endotherm peak at about 108.3° C. and exhibits a X-ray powder diffraction spectrum as shown in FIG. 1. The X-ray powder diffraction pattern of polymorph Form 1 as shown in FIG. 1 exhibits predominant peaks (expressed in degrees 2θ(+/−0.15 degrees 2θ) at one or more of the following positions: 6.721, 11.757, 13.323, 18.222, 21.426 and 21.974. More specifically, such characteristic peaks are at 11.757 and 21.974, and further at 6.721 and further at 13.323, 18.222, and 21.426. Polymorph Form 2 exhibits a predominant endotherm peak at about 115.1° C. as shown in FIG. 6 and exhibits a X-ray powder diffraction spectrum having peaks as shown as shown in FIG. 4.

In another embodiment, [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine is in the form of a composition or mixture of polymorph Form 1 along with one or more other crystalline, solvate, amorphous, or other forms. More specifically, the composition may comprise from trace amounts up to 100% polymorph Form 1, or any amount in between—for example, the composition may comprise less than 0.1%, 0.5%, 1%, 2%, 5%, 10%, 20%, 30%, 40% or 50% by weight of polymorph Form 1 based on the total amount of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine in the composition. Alternatively, the composition may comprise at least 50%, 60%, 70%, 80%, 90%, 95%, 97%, 98%, 99%, 99.5% or 99.9% by weight of polymorph Form 1 based on the total amount of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine in the composition.

In another embodiment, [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine is in the form of a composition or mixture of polymorph Form 2 along with one or more other crystalline, solvate, amorphous, or other forms. More specifically, the composition may comprise from trace amounts up to 100% polymorph Form 2, or any amount in between—for example, the composition may comprise less than 0.1%, 0.5%, 1%, 2%, 5%, 10%, 20%, 30%, 40% or 50% by weight of polymorph Form 2 based on the total amount of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine in the composition. Alternatively, the composition may comprise at least 50%, 60%, 70%, 80%, 90%, 95%, 97%, 98%, 99%, 99.5% or 99.9% by weight of polymorph Form 2 based on the total amount of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine in the composition.

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In general, the compounds of structure (I) may be made according to the organic synthesis techniques known to those skilled in this field, as well as by the representative methods set forth in the Examples. For example, the synthesis of structure (I) may generally proceed according to the following Reaction Scheme 1 through Reaction Scheme 6, which schemes are presented for purposes of exemplification and not limitation.

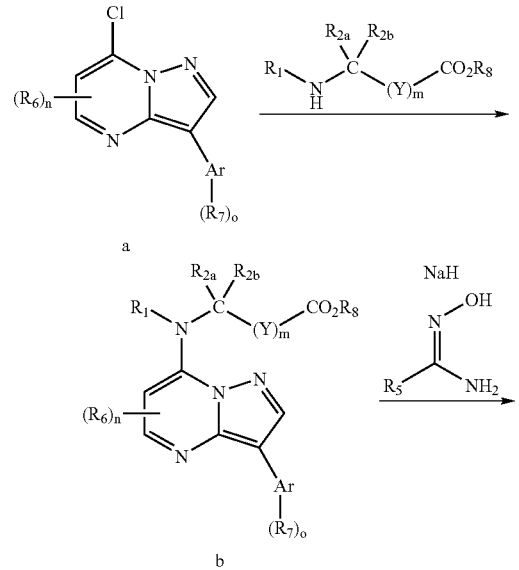

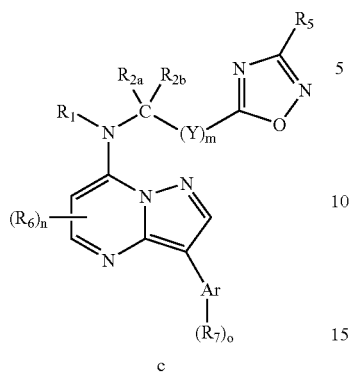

c

Reaction of 7-chloro-pyrazolo-[1,5a]-pyrimidine a with amino acid ester under anhydrous conditions affords amino acid ester b. Reaction of Cmpd b with NaH and substituted amidoxime under anhydrous conditions affords the 5-yl-[1,2,4]oxadiazole Cmpd c.

Reaction Scheme 2

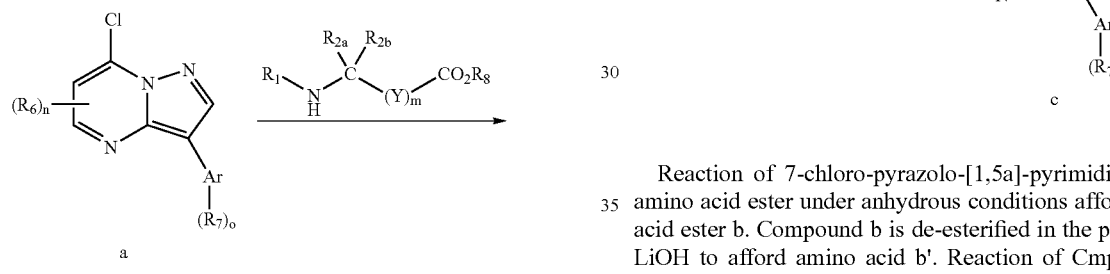

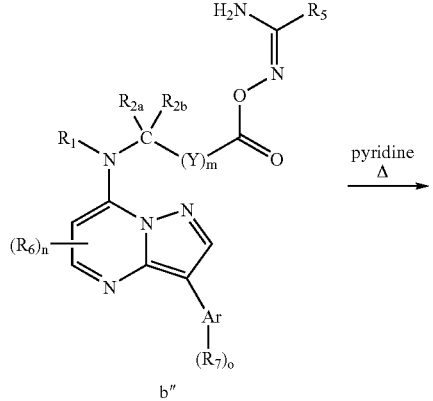

c

Reaction of 7-chloro-pyrazolo-[1,5a]-pyrimidine a with amino acid ester under anhydrous conditions affords amino acid ester b. Compound b is de-esterified in the presence of LiOH to afford amino acid b'. Reaction of Cmpd b' with amidoxime in the presence of DIC and HOBT affords Cmpd b" which undergoes ring closure upon incubation in pyridine at elevated temperature to afford the 5-yl-[1,2,4]oxadiazole Cmpd c.

Reaction Scheme 3

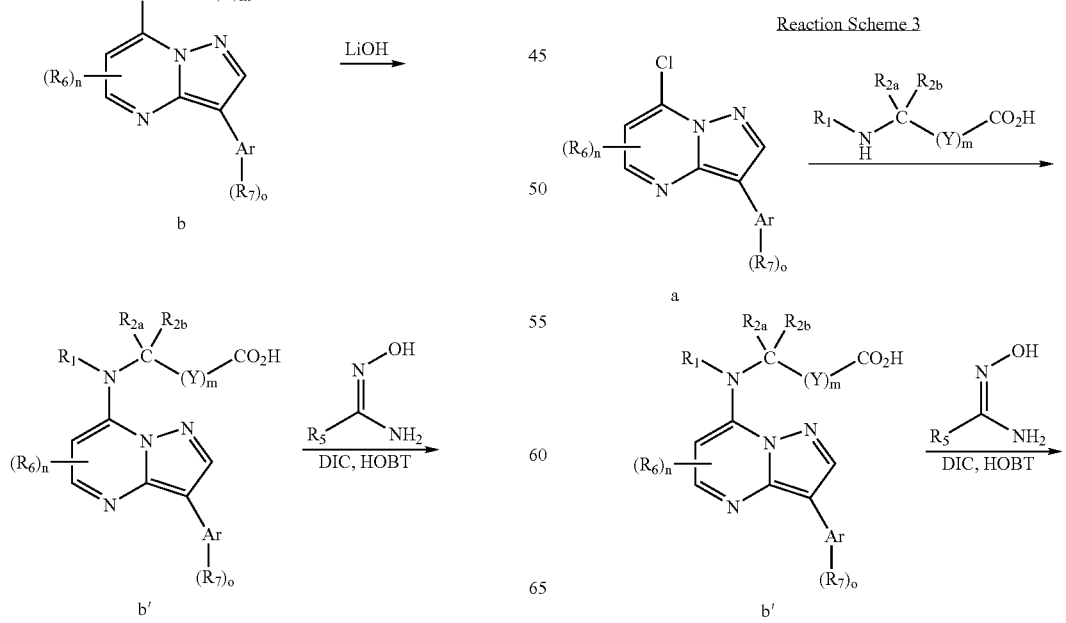

-continued

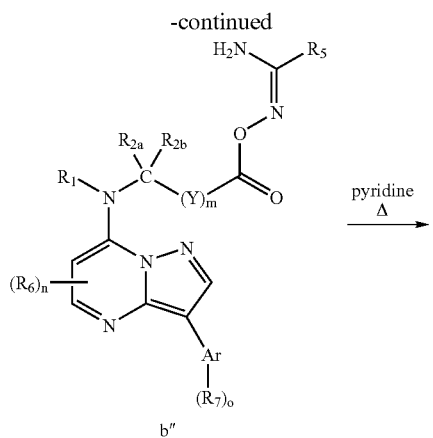

b''

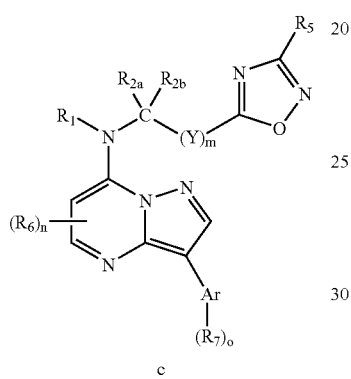

c

Reaction of 7-chloro-pyrazolo-[1,5a]-pyrimidine a with amino acid affords amino acid b'. Reaction of Cmpd b' with amidoxime in the presence of DIC and HOBT affords Cmpd b'' which undergoes ring closure upon incubation in pyridine at elevated temperature to afford the 5-yl-[1,2,4]oxadiazole Cmpd c.

-continued

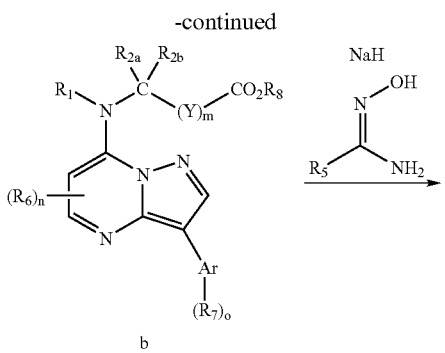

b

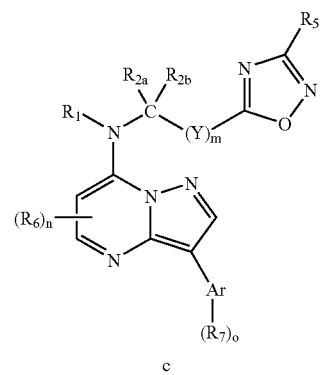

c

Reaction of 7-chloro-pyrazolo-[1,5a]-pyrimidine a with substituted amine affords Cmpd d, which reacts with bromo ester to afford amino acid ester b. Compound b reacts with amidoxime in the presence of NaH to afford the 5-yl-[1,2,4] oxadiazole Cmpd c.

Reaction Scheme 4

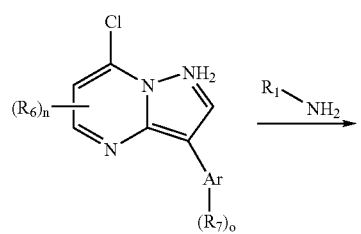

a

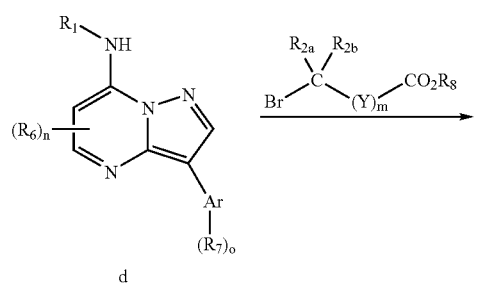

d

Reaction Scheme 5

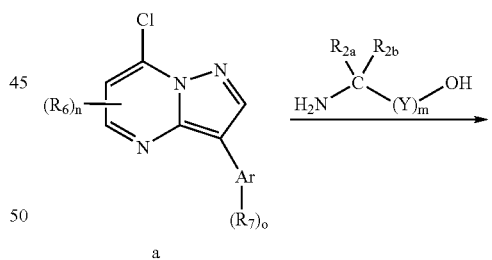

a

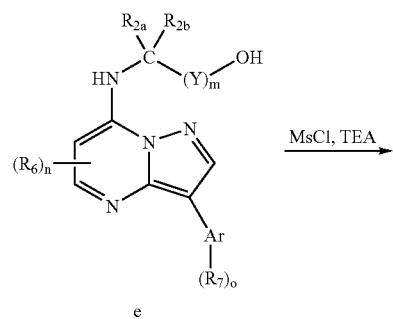

e undergoes ring closure in the presence of DMA-DMA to afford the 3-yl-[1,2,4]oxadiazole Cmpd i.

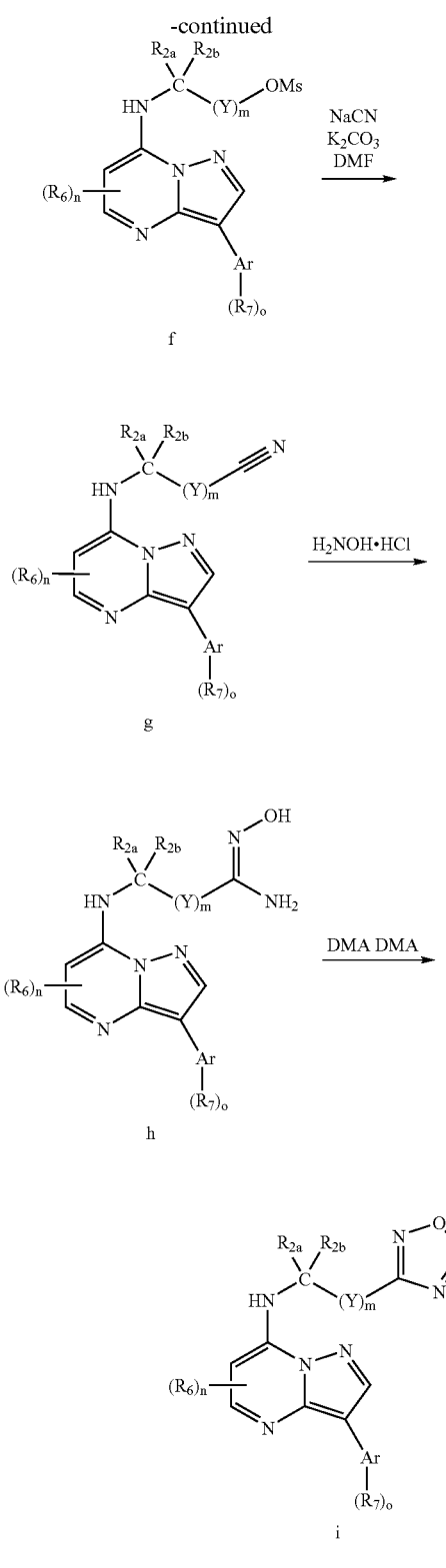

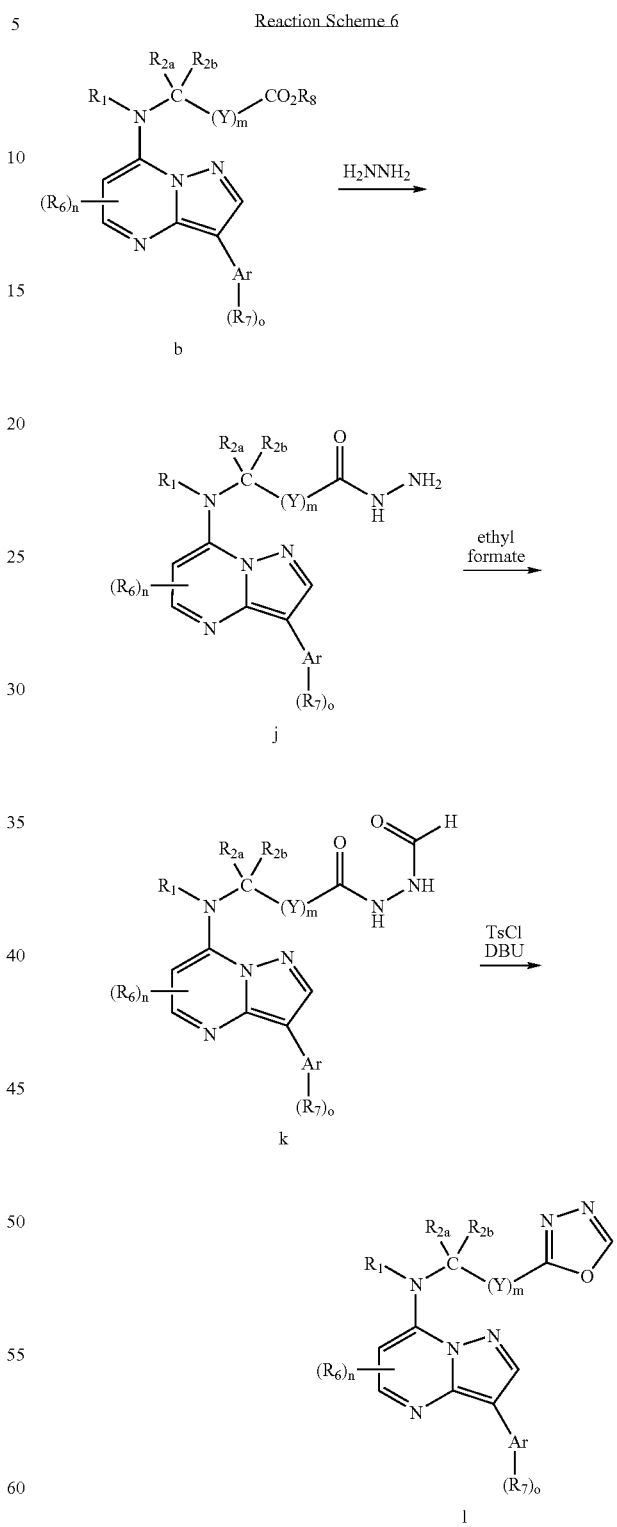

Reaction of 7-chloro-pyrazolo-[1,5a]-pyrimidine a with aminol and triethylamine (TEA) in acetonitrile affords aminol e which can be mesylated by p-toluenesulfonyl chloride in the presence of TEA to afford Cmpd f. Cyano functionality can be introduced into Cmpd f affording Cmpd g, which can react with hydroxylamine to give Cmpd h. Compound h Reaction of 7-chloro-pyrazolo-[1,5a]-pyrimidine amino acid ester b with hydrazine giving Cmpd j followed by reaction with ethyl formate giving Cmpd k and ring closure with TsCl and DBU affords the 5-yl-[1,3,4]oxadiazole Cmpd l.

Reaction Scheme 7

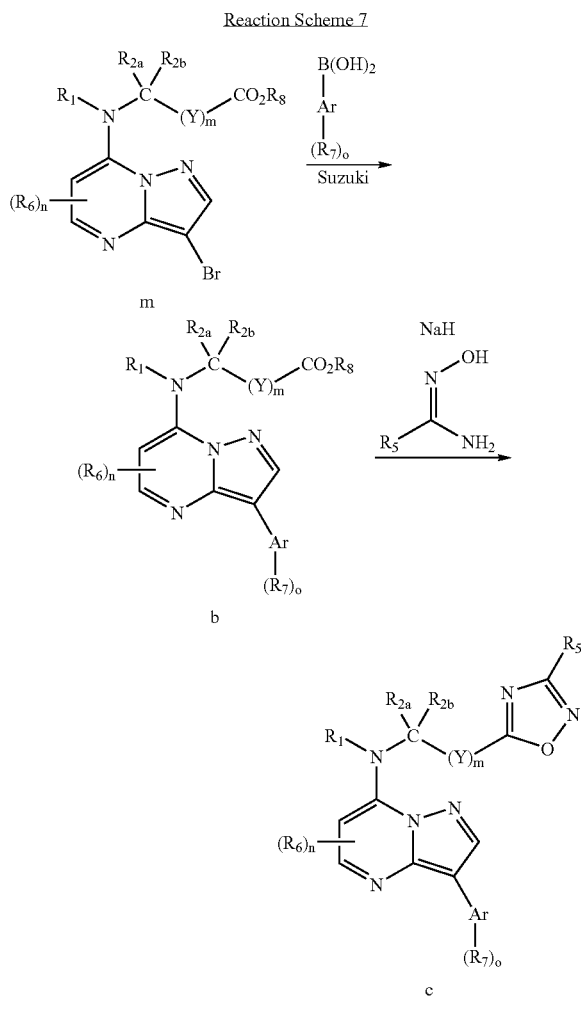

Reaction of 3-bromo-7-amino-pyrazolo-[1,5a]-pyrimidine amino acid ester m with arylboronic acid under conditions of the Suzuki reaction affords the 3-aryl-7-amino-pyrazolo-[1,5a]-pyrimidine amino acid ester b which reacts with NaH and substituted amidoxime to afford Cmpd c.

The effectiveness of a compound as a CRF receptor antagonist may be determined by various assay methods. CRF antagonists of this invention may be capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (J. Neuroscience 7:88, 1987) and Battaglia et al. (Synapse 1:572, 1987). As mentioned above, CRF antagonists of this invention include compounds which demonstrate CRF receptor affinity. CRF receptor affinity may be determined by binding studies that measure the ability of a compound to inhibit the binding of a radiolabeled CRF (e.g., [$^{125}$I]tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention may have a $K_i$ of less than 10 µM. In one embodiment of this invention, a CRF receptor antagonist has a $K_i$ of less than 1 µM, and in a another embodiment the $K_i$ is less than 0.25 µM (i.e., 250 nM). As set forth in greater detail below, the $K_i$ values may be assayed by the methods set forth in Example 25. CRF receptor antagonists of the present invention having a $K_i$ of less than 0.10 µM (i.e., 100 nM) include Examples 11-1, 11-2, 11-3, 11-4, 11-5, 11-6, 11-9, 11-10, 11-11, 11-13, 11-17, 11-18, 11-20, 11-23, 11-26, 12-1, 12-2, 12-3, 12-4, 12-5, 12-9, 12-10, 12-11, 13-1, 13-2, 13-3, 13-4, 13-5, 13-6, 13-7, 13-8, 13-9, 14-1, 14-2, 14-3, 14-4, 15-1, 17-1, 17-2, 17-3, 18-1, 18-2, 19-1, 20-1, 20-2, 21-1, 22-1, 23-2, 24-1, 24-2, 24-4, and 24-6.

CRF receptor antagonists of the present invention may demonstrate activity at the CRF receptor site, and may be used as therapeutic agents for the treatment of a wide range of disorders or illnesses including endocrine, psychiatric, and neurological disorders or illnesses. More specifically, CRF receptor antagonists of the present invention may be useful in treating physiological conditions or disorders arising from the hypersecretion of CRF. Because CRF is believed to be an important neurotransmitter that activates and coordinates the endocrine, behavioral and automatic responses to stress, CRF receptor antagonists of the present invention may be useful in the treatment of neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), pain, Cushing's disease, infantile spasms, epilepsy and other seizures in both infants and adults, and various substance abuse and withdrawal (including alcoholism).

Within the context of the present invention, the following terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of the present invention including salts and pharmaceutically acceptable solvates thereof may also be of use in the treatment of the following disorders:—

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

Anxiety disorders including Social Anxiety Disorder, Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder and Anxiety Disorder Not Otherwise Specified (300.00):

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-Induced Sleep Disorder including the subtypes Insomnia Type, Hypersomnia Type, Parasomnia Type and Mixed Type:

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50):

Autistic Disorder (299.00); Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9):

Enhancement of cognition including the treatment of cognition impairment in other diseases such as schizophrenia, bipolar disorder, depression, other psychiatric disorders and psychotic conditions associated with cognitive impairment, e.g. Alzheimer's disease: and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

All of the various forms and sub-forms of the disorders mentioned herein are contemplated as part of the present invention.

"Treatment" includes prophylaxis, where this is appropriate for the relevant condition(s).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention include a pharmaceutically effective amount of a CRF receptor antagonist of the present invention (i.e., a compound of structure (I)) and a pharmaceutically acceptable carrier or diluent. Thus, the CRF receptor antagonist is present in the composition in an amount which is effective to treat a particular disorder. In one embodiment of the invention, the pharmaceutical compositions of the present invention may include a CRF receptor antagonist in an amount from 0.1 mg to 250 mg per dosage depending upon the route of administration. In another embodiment the dosage may be from 1 mg to 60 mg. In other embodiments, the dosage may be, for example, 5 mg, 10 mg, 15 mg or 20 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment, the present invention provides a method for treating a variety of disorders or illnesses, including endocrine, psychiatric and neurological disorders or illnesses. Such methods include administering of a compound of the present invention to a mammal (e.g., a person) in an amount sufficient to treat the disorder or illness. Such methods include systemic administration of a pharmaceutical composition containing a pharmaceutically effective amount of a CRF receptor antagonist of this invention. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

In another embodiment, the present invention permits the diagnostic visualization of specific sites within the body by the use of radioactive or non-radioactive pharmaceutical agents Use of a compound of the present invention may provide a physiological, functional, or biological assessment of a patient or provide disease or pathology detection and assessment. Radioactive pharmaceuticals are employed in scintigraphy, positron emission tomography (PET), computerized tomography (CT), and single photon emission computerized tomography (SPECT). For such applications, radioisotopes are incorporated of such elements as iodine (I) including $^{123}$I (PET), $^{125}$I (SPECT), and $^{131}$I, technetium (Tc) including $^{99}$Tc (PET), phosphorus (P) including 31P and $^{32}$P, chromium (Cr) including $^{51}$Cr, carbon (C) including $^{11}$C, fluorine (F) including $^{18}$F, thallium (Tl) including $^{201}$Tl, and like emitters of positron and ionizing radiation. Non-radioactive pharmaceuticals are employed in magnetic resonance imaging (MRI), fluoroscopy, and ultrasound. For such applications, isotopes are incorporated of such elements as gadolinium (Gd) including $^{153}$Gd, iron (Fe), barium (Ba), manganese (Mn), and thallium (Tl). Such entities are also useful for identifying the presence of particular target sites in a mixture and for labeling molecules in a mixture.

The following examples are provided for purposes of illustration and not for purposes of limitation.

EXAMPLES

The CRF receptor antagonists of this invention may be prepared by the methods disclosed in the Examples. Example 25 presents a method for determining the receptor binding affinity, and Example 26 discloses an assay for screening compounds of this invention for CRF-stimulated adenylate cyclase activity.

Abbreviations:
AcCN, MeCN: acetonitrile
AcCN: Acetonitrile
DBU: Diaminobutyric acid
DCM: Dichloromethane
DEAD: diethylazodicarboxylate
DIC: N,N'-Diisopropylcarbodiimide
DIU: N,N'-diisopropylurea
DMA-DMA: N,N-dimethylacetamide dimethyl acetal
DME: 1,2-dimethoxyethane
DMF: Dimethylformamide
DMF-DMA: N,N-dimethylformamide dimethyl acetal
EAA: Ethyl acetoacetate
HOBT: 1-Hydroxybenzotriazole
LC/MS: liquid chromatography-mass spectroscopy
MDA: Malondialdehyde bis-dimethylacetal
MsCl: Methanesulfonyl chloride
NaBH(OAc)$_3$: Sodium Triacetoxyborohydride
Pd—C: Palladium (10%) on Carbon
TEA: Triethylamine
TFA: Trifluoroacetic acid
THF: Tetrahydrofuran
TosMIC: Tosylmethyl isocyanide
TsCl: p-toluenesulfonyl chloride
TsOH: p-Toluenesulfonic acid Prep. HPLC-MS Gilson HPLC-MS equipped with Gilson 215 auto-sampler/fraction collector, an UV detector and a ThermoFinnigan AQA Single QUAD Mass detector (electrospray);
HPLC column: BHK ODS-O/B, 5μ, 30×75 mm
HPLC gradients: 35 mL/min, 10% acetonitrile in water to 100% acetonitrile in 7 min, maintaining 100% acetonitrile for 3 min.

Analytical Method 1-High Performance Liquid Chromatography (HPLC-MS)

Platform: HP 1100 series: equipped with an auto-sampler, an UV detector (220 nM and 254 nM), a MS detector (electrospray);
Column: Phenomenex SynergiMAX-RP, 4 micron, 2×50 mm;
Mobile phase: A=water, 0.025% TFA; B=acetonitrile, 0.025% TFA;
Flow rate: 1.0 mL/min;
Gradient: 5% B/95% A to 95% B/5% A over 13 min, then hold 2.5 min;

Analytical Method 2-Supercritical Fluid Chromatography (SFC)

Platform: Berger FCM1200 SFC pump, Agilent Diode Array Detector, Agilent Model 220 Microplate autosampler, Agilent Model 1946 MSD (APCI interface);
Column: Berger Pyridine 60A, 4 micron, 3×150 mm;
Solvents: SFC Grade CO$_2$, Optima-grade methanol with 1.5% water and 0.025% ethanesulfonic acid;
Flow rate: 4.0 mL/min, 120 Bar backpressure;
Gradient: 5-55% methanol/CO$_2$ in 2.4 min.

Analytical Method 3-Analytical HPLC-MS (LC-MS)

Platform: HP 1100 series: equipped with an auto-sampler, a UV detector (220 nM and 254 nM), and an MS detector (APCI);
Column: Waters XTerra 3×250 mm;
Solvent A: water with 0.025% TFA
Solvent B: acetonitrile with 0.025% TFA
Flowrate: 1.0 mL/min;
Gradient: 5% B for 1.55 min, then 10 to 90% B over 46 min (47.55 min total)

Analytical Method 4-Analytical HPLC-MS (LC-MS),

Platform: HP/Agilent 1100 series: equipped with an auto-sampler, a UV detector (220 nM and 254 nM), and an MS detector (APCI);
Column: Phenomonex Synergymax RP 2.0×50 mm;

Flowrate: 1.0 mL/min;
Solvent A: 0.05% TFA in water
Solvent B: 0.05% TFA in acetonitrile
Gradient: 5% B for 0.25 min, then from 5% B to 90% B from 0.25 to 2.25 min, then 90% B from 2.25 to 3.25 min.

Example 1

Synthesis of Reagent [5-(7-chloro-2,5-dimethyl-pyrazolo[1,5-a]pyrimidin-3-yl)-4-methyl-pyridin-2-yl]-dimethyl-amine

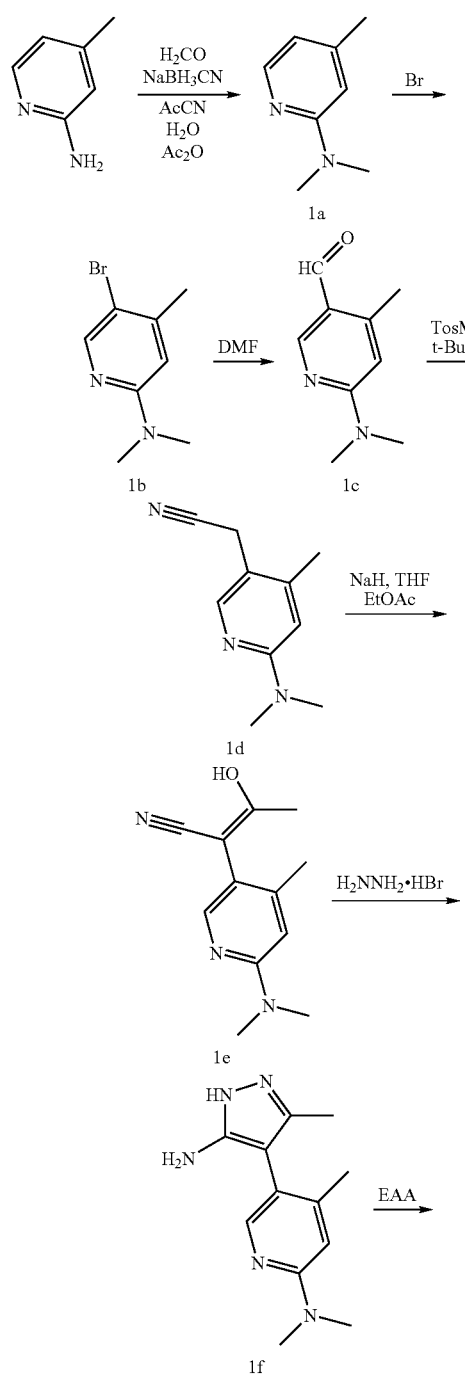

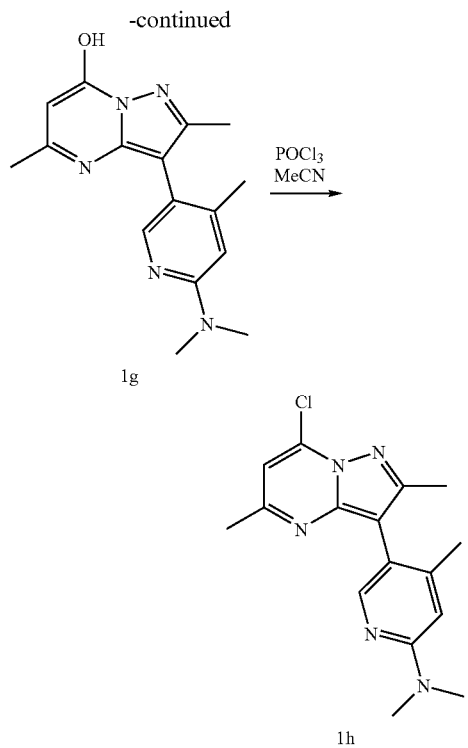

Step 1A:

To a mixture of 2-amino-4-picoline (33 g), NaBH$_3$CN (57 g), formaldehyde (37% aq. solution, 240 mL) in acetonitrile (1 L) and water (200 mL) was added dropwise acetic acid (60 mL) at 0° C. in 2 hr. The resultant solution was stirred at RT for 7 days and then concentrated in vacuo. The residue was basified with solid NaOH to pH 10 and extracted with hexanes (3×700 mL). The combined extract was washed with 1N aq. NaOH and brine, dried over Na$_2$SO$_4$ and evaporated in vacuo to give 2-dimethylamino-4-methylpyridine as a colorless oil (Cmpd 1a, 36 g, 88%). $^1$H NMR (CDCl$_3$): 2.26 (s, 3H), 3.07 (s, 6H), 6.33 (s, 1H), 6.40 (d, 1H), 8.02 (d, 1H); MS (CI) m/e 137 (MH$^+$).

Step 1B:

A mixture of Cmpd 1a (32 g), Na$_2$CO$_3$ (30 g) in DCM (50 mL) and water (400 mL) was treated dropwise with a solution of bromine (13 mL) in DCM (50 mL) at 0° C. in 0.5 hr. The resultant light brown suspension was stirred at 0° C. for 0.5 hr. The resultant was extracted with hexanes (2×600 mL) and the combined extract was washed with brine, dried over Na$_2$SO$_4$ and evaporation in vacuo. The crude resultant was purified by chromatography on silica gel with 1:5 ethyl acetate/hexanes to give 5-bromo-2-dimethylamino-4-methylpyridine as a tan solid (Cmpd 1b, 78% yield). $^1$H NMR (CDCl$_3$): 2.30 (s, 3H), 3.04 (s, 6H), 6.38 (s, 1H), 8.14 (s, 1H); MS (CI) m/e 216 (MH$^+$).

Step 1C:

Into a suspension of magnesium (11.3 g) in THF (20 mL) was added a quarter portion of a solution of Cmpd 1b (48.5 g) from Step 1B in THF (100 mL). The reaction was initiated with 5 drops of 1,2-dibromoethane with slightly heating. After initiation of the reaction 10 mL of THF was added. The rest of the solution of Cmpd 1b was added dropwise to maintain a gentle reflux. After completion of addition the mixture was stirred at RT for 0.5 hr before DMF (1.5 eq.) was slowly injected at 0° C. The resultant mixture was stirred at RT overnight and quenched with saturated aq. NH$_4$Cl. The resultant was extracted with ether (2×500 mL) and the combined extract was washed with brine, dried over MgSO$_4$, filtered and concentrated in vacuo. The resultant was purified by chromatography on silica gel with 1:5 ethyl acetate/hexanes to afford 2-dimethylamino-4-methyl-5-formylpyridine as a tan solid (Cmpd 1c, 77% yield). The analytic sample was obtained by crystallization from ether/hexanes. $^1$H NMR (CDCl$_3$): 2.57 (s, 3H), 3.11 (s, 6H), 6.28 (s, 1H), 8.43 (s, 1H), 9.87 (s, 1H); MS (CI) m/e 165 (MH$^+$).

Step 1D:

Into a suspension of tBuOK (12.5 g) in DME (70 mL) at −50° C. was added dropwise a solution of TosMIC (15.6 g) in DME (70 mL). The brown solution was stirred at −50° C. for 10 min before a solution of Cmpd 1c (11 g) in DME (70 mL) was added dropwise. The resultant mixture was stirred at −50° C. for 0.5 hr and quenched with methanol (70 mL). This mixture was heated to reflux for 1 hr and the solvent was evaporated and partitioned in ethyl acetate-water. The organic layer was washed with brine, dried over MgSO$_4$ and filtered through a silica gel pad with ethyl acetate. This work-up gave 2-dimethylamino-4-methyl-5-(cyanomethyl)pyridine as a yellow solid (Cmpd id, 9.5 g, 80%). $^1$H NMR (CDCl$_3$): 2.31 (s, 3H), 3.08 (s, 6H), 3.54 (s, 2H), 6.36 (s, 1H), 7.99 (s, 1H); MS (CI) m/e 176 (MH$^+$)

Step 1E:

Into a suspension of Cmpd 1d (40 g, 0.23 mol) and NaH (2.5 eq.) in THF (100 mL) was added about 5 mL of ethyl acetate. The mixture was stirred at RT until an exothermic reaction started and hydrogen evolved vigorously. Ethyl acetate (50 µL) was then added dropwise to maintain a gentle reflux. The mixture was stirred at RT for 2 hr before it was quenched with water (100 mL). The organic phase was separated and the aqueous phase was washed several times with ethyl ether. The aqueous phase was then acidified with acetic acid, and the resultant was extracted with ethyl acetate (5×800 mL). The combined extract was washed with brine (50 mL) and dried over MgSO$_4$. Concentration in vacuo gave the keto form 1-cyano-1-(6-dimethylamino-4-methylpyridin-3-yl)acetone and the 3-hydroxy-but-2-enenitrile enol form (Cmpd 1e) as a brown solid (40 g, 80% yield). $^1$H NMR (CDCl$_3$): 1:1 mixture of enol and ketone form, 2.24 (s, 1.5×3H), 2.32 (s, 0.5×3H), 2.88 (s, 0.5×6H), 3.09 (s, 0.5×6H), 4.50 (brs, 0.5× 1H), 4.62 (s, 0.5×1H), 6.13 (s, 0.5×1H), 6.35 (s, 0.5×1H), 7.60 (s, 0.5×1H), 8.05 (s, 0.5×1H); MS (CI) m/e 218 (MH$^+$).

Step 1F:

A mixture of Cmpd 1e (30 g) and hydrazine hydrobromide (62 g) in ethanol (150 mL) and water (20 mL) was heated to reflux for 1 hr. Ethanol was removed in vacuo and the residue was diluted with water (50 mL). The aqueous phase was basified with solid Na$_2$CO$_3$ and the resultant was extracted with ethyl acetate. The extract was dried over MgSO$_4$, filtered and concentrated in vacuo to give 3-amino-4-(6-dimethylamino-4-methylpyridin-3-yl)-5-methylpyrazole as a brownish oil (Cmpd 1f, 30 g, 93% yield) which was crystallized from ether-hexanes. $^1$H NMR (CDCl$_3$): 2.07 (s, 3H), 2.14 (s, 3H), 3.10 (s, 6H), 4.10 (brs, 3H), 6.45 (s, 1H), 7.92 (s, 1H); MS (CI) m/e 232 (MH$^+$)

Step 1G:

A solution of Cmpd 1f (29.5 g) and ethyl acetoacetate (2.5 eq.) in dioxane (100 mL) was heated to reflux for 20 hr. The suspension was cooled, and ether (200 mL) was added. The solid was collected by vacuum filtration and 2,5-dimethyl-3-(6-dimethylamino-4-methylpyridin-3-yl)-7-hydroxypyrazolo[1,5-a]pyrimidine was obtained as a tan solid (Cmpd 1g, 23.5 g, 62% yield). The filtrate was concentrated in vacuo and the residue was dissolved in water (50 mL). This aqueous phase was extracted with ether (3×300 mL) to remove starting material and impurity. The product was then extracted with DCM (5×300 mL) affording another 6 g (total yield 78%) of Cmpd 1g. $^1$H NMR (CDCl$_3$): 2.10 (s, 3H), 2.20 (s, 3H), 2.33 (s, 3H), 2.91 (s, 6H), 5.64 (s, 1H), 6.24 (s, 1H), 7.65 (s, 1H). MS (CI) m/e 298 (MH$^+$)

Step 1H:

A suspension of Cmpd 1g (11 g) and POCl$_3$ (2 eq.) in acetonitrile (50 mL) was heated to reflux for 8 hr. The reaction was quenched with ice and basified with Na$_2$CO$_3$. The product was extracted with ethyl acetate (2×200 mL). The extract was dried over MgSO$_4$, filtrated through a silica gel pad and concentrated in vacuo to give [5-(7-Chloro-2,5-dimethyl-pyrazolo[1,5-a]pyrimidin-3-yl)-4-methyl-pyridin-2-yl]-dimethyl-amine as a yellowish solid (Cmpd 1 h, 11.5 g, 99% yield). $^1$H NMR (CDCl$_3$): 2.13 (s, 3H), 2.43 (s, 3H), 2.53 (s, 3H), 3.11 (s, 6H), 6.49 (s, 1H), 6.78 (s, 1H), 8.01 (s, 1H); MS (CI) m/e 316 (MH$^+$)

Example 2

Synthesis of Reagent
(2,4-dimethoxy-phenyl)-acetonitrile

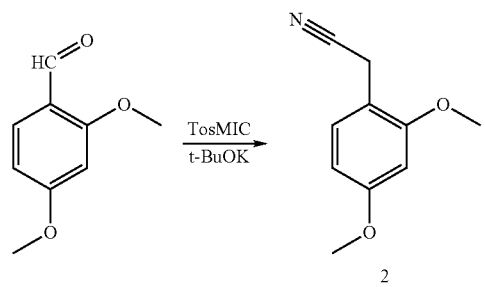

Step 2:

Into a suspension t-BuOK (47.3 g) in DME (150 mL) at −30° C. (dry ice/acetone bath) was added dropwise a solution of TosMIC (58.8 g) in DME (150 mL), keeping the temperature of the mixture below −30° C. The solution was stirred and allowed to cool to −60° C. over 10 minutes before a solution of 2,4-dimethoxybenzaldehyde (50 gl) in DME (150 mL) was added dropwise, keeping the temperature of the reaction mixture below −50° C. The reaction mixture was stirred at −50 to −60° C. for 1 hr, then methanol (200 mL) was added. This mixture was heated to reflux for 2 hr. The solvent was evaporated and the residue was partitioned between ethyl acetate and water with acetic acid (40 mL) added. The aqueous layer was extracted with one additional portion of ethyl acetate, then the combined ethyl acetate layers were washed with brine, dried over magnesium sulfate, filtered, and concentrated. The residue was purified by silica gel column chromatography, eluting with 1:1 hexanes/ethyl acetate to provide 2 (48.8 g).

Example 3

Synthesis of Reagents 2-chloro-4-methoxy-benzaldehyde and (2-chloro-4-methoxy-phenyl)-acetonitrile

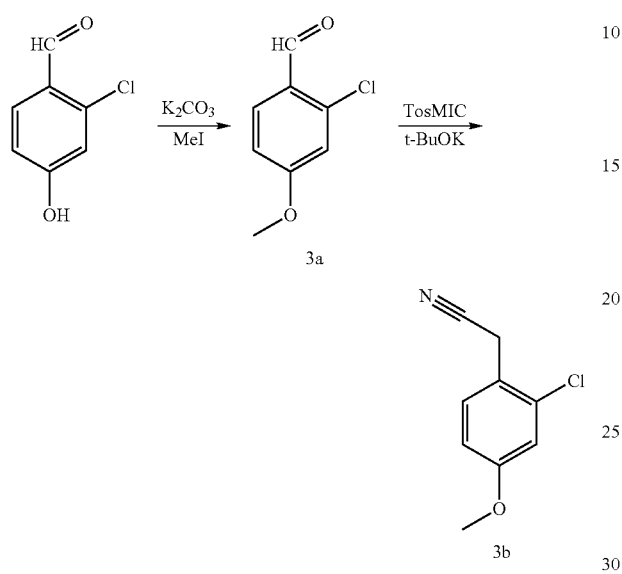

Step 3A:

2-chloro-4-hydroxybenzaldehyde (9.56 g) and K$_2$CO$_3$ (25.3 g) were stirred with DMF (30 mL) at RT for 30 min. Iodomethane (4.0 mL) was added, the reaction vessel was sealed, and the mixture was stirred at RT for 16 hr. 300 mL of 2:1 hexanes/ethyl acetate was added, after which the mixture was washed 3 times with water and once with brine. The organic layer was dried over sodium sulfate, filtered then evaporated to a volume of about 50 mL. The precipitate which formed was filtered and washed with hexanes to provide Cmpd 3a as a tan solid (6.0 g).

Step 3B:

Formation of the acetonitrile Cmpd 3b followed the procedure of Step 2 employing t-BuOK and TosMIC in DME.

Example 4

Synthesis of Reagent 7-Chloro-3-(4-methoxy-2-methyl-phenyl)-2,5-dimethyl-pyrazolo[1,5-a]pyrimidine

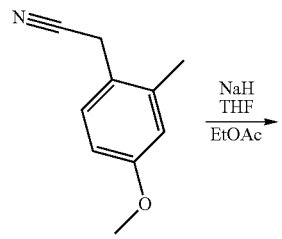

Step 4A:

Sodium hydride (12.0 g of 60% suspension in oil) was added to a solution of 4-methoxy-2-methylphenylacetonitrile (30 g) in anhydrous THF (300 mL) at RT under nitrogen. About 2 mL of ethyl acetate was added and the mixture was heated gradually to an internal temperature of 66° C. After about 10 minutes a vigorous reaction ensued, and heating was discontinued while additional ethyl acetate (75 mL) was added dropwise over about 20 minutes to maintain reflux. Vigorous hydrogen evolution was observed. By the end of the ethyl acetate addition, the reaction mixture began to cool, and the mixture was stirred and allowed to cool over 3 hr. 150 mL water was added followed by 300 mL ether. The aqueous layer was washed with two additional portions of ether. The ether extracts were discarded. The aqueous layer was acidified with 20 mL concentrated hydrochloric acid (pH ~5), then the mixture was extracted with three portions of ethyl acetate. The combined ethyl acetate extracts were dried over sodium sulfate, filtered and evaporated to give crude ketonitrile 4a as a slightly amber oil (39 g) which was carried forward without further purification.

Alternate Step 4A:

Sodium hydride (35.44 g of 60% suspension in oil, 1.48 mol) was added to a solution of 4-methoxy-2-methylphenylacetonitrile (148.8 g, 0.92 mol) in anhydrous THF (2 L) at rt. EtOAc (30 mL) was added and the mixture was heated gradually to an internal temperature of 70.1° C. Reaction initiated, and heating was discontinued immediately by removing the heating mantle completely. EtOAc (374 mL, total 4.14 mol) was added dropwise to maintain reflux. Vigorous hydrogen evolution was observed and the reaction was stirred for 2 hours after complete EtOAc addition. Water (750 mL) was added, followed by hexane (750 mL) with vigorous stirring and the aqueous layer was separated and acidified with conc. HCl to pH ~2. The aqueous layer was extracted with EtOAc (3×400 mL) and the combined extracts dried (MgSO$_4$) and concentrated in vacuo to afford 4a as an amber colored oil (183.8 g, 0.90 mol, 98%, 99% purity).

Step 4B:

A mixture of crude 4a (37.8 g) and hydrazine monohydrobromide (23.1 g) was suspended in absolute ethanol (225 mL) and water (25 mL). The mixture was refluxed for approximately 3 hr. The reaction mixture was allowed to cool, then the solvent was evaporated. Ethyl acetate was added, and the mixture neutralized by addition of saturated aq. NaHCO$_3$ (200 mL), and the mixture was extracted with ethyl acetate (4×100 mL). The combined organic layers were washed with brine (100 mL), dried over magnesium sulfate, filtered and evaporated to give crude Cmpd 4b as a pale orange oil (45 g) which was carried forward without further purification.

Alternate Step 4B:

Compound 4a (183.8 g, 0.9 mol) was dissolved in EtOH (1.09 L) and water (109 mL) and hydrazine hydrobromide (112.39 g, 0.99 mol) was added. The mixture was refluxed (90° C. bath temperature) for 2.5 h, at which time LC/MS monitoring showed complete reaction. The reaction mixture was allowed to cool and concentrated in vacuo to remove EtOH and partitioned between NaHCO$_3$ (950 mL, sat. aq.) and EtOAc (400 mL). The aqueous layer was separated and extracted further with EtOAc (3×400 mL) and the combined organic layers were washed with brine (400 mL), dried (MgSO$_4$) and concentrated in vacuo to give the crude aminopyrazole 4b as an amber colored oil (168.8, 80% pure), which was carried on without further purification.

Step 4C:

Ethyl acetoacetate (EAA) (28.4 mL) was added to a solution of 4b (40.2 g, 0.18 mol) in dry dioxane (180 mL). The mixture was refluxed at 115° C. for about 20 h, during which time pyrazolopyrimidine 4c precipitated from solution as a white solid. The reaction mixture was cooled and the precipitate was filtered and washed with cold ether. The precipitate was then dried in vacuo to yield 22.5 g (0.079 mol, 42.7%) of Cmpd 4c as an off-white solid.

Alternative Step 4C:

Ethyl acetoacetate (EAA) (200 mL) was added to a solution of the crude 4b (180 g, 0.62 mol) in absolute ethanol (500 mL) and glacial acetic acid (500 mL). The mixture was heated to reflux for 2 h, during which time pyrazolopyrimidine 4c precipitated from solution as a white solid. The reaction mixture was cooled and the precipitate was filtered and washed with cold ether. The precipitate was then dried in vacuo to yield 131 g (0.46 mol, 75%) of Cmpd 4c as an off-white solid.

Step 4D:

Phosphorous oxychloride (12 mL) was added to a suspension of 4c (12.1 g) in anhydrous acetonitrile (60 mL) at RT. The mixture was heated at 80° C. for 30 h, at which point the reaction mixture was a clear, deep-red solution. The reaction mixture was poured onto 300 mL of ice/water, and the reaction flask was rinsed with 100 mL ethyl acetate. The mixture was then stirred and neutralized with sat. aq. sodium carbonate. The red mixture became yellow upon neutralization. The layers were separated and the aqueous layer was extracted with ethyl acetate (4×100 mL). The combined organic layers were washed with brine (100 mL), dried over magnesium sulfate, filtered, and concentrated to give a clear brown oil. The crude product was chromatographed on silica gel using 2:1 hexanes/ethyl acetate, giving Cmpd 4d (12.1 g, 94%) as a clear yellow oil, which solidified upon standing.

Alternate Step 4D:

To a suspension of pyrazolopyrimidine 4c (235.1 g, 0.83 mol) in anhydrous acetonitrile (1.2 L) was added phosphorous oxychloride (232 mL, 2.49 mol) at rt. The mixture was heated to 80° C. and stirred for 20 h and allowed to cool and concentrated in vacuo to approximately ¼ the volume. Ice chips and water were carefully added with stirring to make the total volume up to 1 L. Ensuring the temperature was always below 5° C. using an ice bath and adding more ice chips to the mixture, the pH was brought to around 6-7 using NaOH (2 M, aq.). The resulting cold suspension was extracted with EtOAc (3×500 mL) and the combined organic layers dried (MgSO$_4$) and concentrated in vacuo to give chloropyrimidine 4d as a red waxy crystalline solid (258.3 g, 93% purity), which was used directly for the next step.

Also prepared by this method were:

4e 2,5-dimethyl-3-(2,4-dimethoxyphenyl)-7-chloropyrazolo[1,5-a]-pyrimidine (starting from 2);

4f 2,5-dimethyl-3-(2-chloro-4-methoxyphenyl)-7-chloropyrazolo[1,5-a]-pyrimidine (starting from 3b); and 4 g 2,5-dimethyl-3-(4-ethoxyphenyl)-7-chloropyrazolo[1, 5-a]-pyrimidine (starting from 4-ethoxyphenylacetonitrile).

Example 5

Synthesis of Reagent 2-(3-bromo-2,5-dimethyl-pyrazolo[1,5-a]pyrimidin-7-ylamino)-butyric acid methyl ester

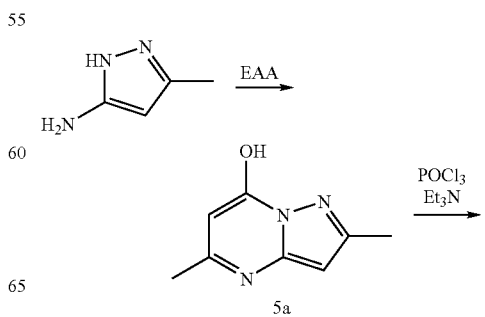

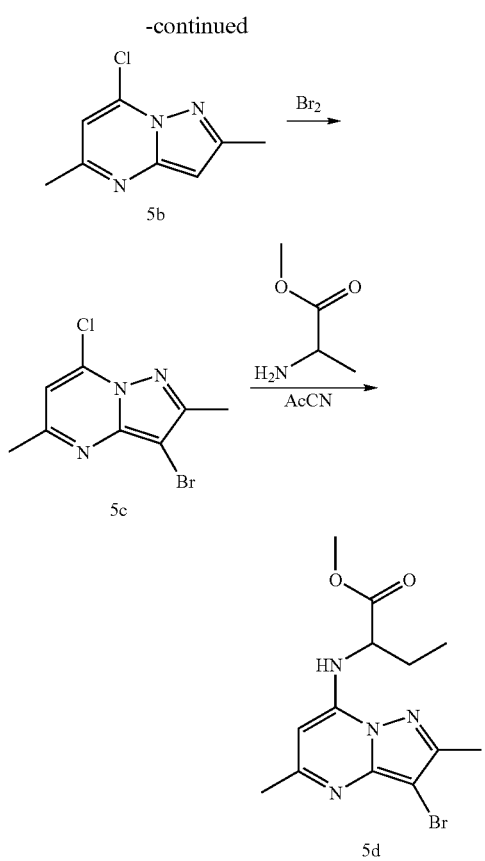

Step 5A:

A solution of 3-amino-5-methylpyrazole (20.0 g), ethyl acetoacetate (32.0 g), acetic acid (6 mL), and dioxane (150 mL) was refluxed for 16 hr. A white solid precipitated, which was collected by filtration. The filter cake was washed with ether to provide 5a (29.0 g, 86%) as a white solid.

Step 5B:

To a suspension of 5a (5.0 g) in 1,4-dioxane (30 mL) was added triethylamine (8.50 mL) and phosphorous oxychloride (7.4 mL). The reaction was heated under nitrogen at 100° C. for 2 hr. The reaction mixture was cooled in an ice bath then treated successively with water and aq. sodium bicarbonate solution (final pH 8). Dichloromethane was added and the mixture was washed three times with water. The combined organic layers were dried over magnesium sulfate, filtered, and concentrated to a dark brown oil. The crude resultant was purified by silica gel chromatography using 30% ethyl acetate in hexanes as eluant, providing 5b (3.8 g, 70%) as a white solid. LC/MS: 182.0 (MH+)

Step 5C:

Bromine (0.51 mL) was added to a solution of 5b (1.5 g) in 1:1 methanol/water (40 mL) at −10° C. After 10 min, the mixture was filtered to collect the precipitate that had formed. The filter cake was washed with cold MeOH/H$_2$O (1:1) until the filtrate ran clear and was then dried under vacuum to yield 5c (3.0 g) as an off-white solid, which was used immediately without further purification.

Step 5D:

To compound 5c (prepared above) was added (RS) methyl 2-amino butyrate hydrochloride (1.3 g) followed by acetonitrile (40 mL) and 4 angstrom molecular sieves. The reaction mixture was heated at 110° C. for 5 h. Ethyl acetate and aq. sodium bicarbonate were added to the cooled reaction mixture, then the organic layer was washed three times with brine. The organic layer was dried over magnesium sulfate, filtered, and evaporated to give a crude yellow solid. Purification by silica gel chromatography using 30% ethyl acetate/hexanes as eluant provided 5d (800 mg, 28%) as an off white solid.

Example 6

Synthesis of Reagent N-Hydroxy-acetamidine

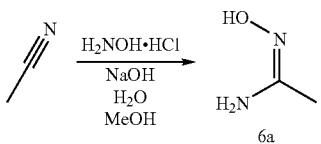

Step 6:

Sodium hydroxide (39 g of a 50% aq. solution) was added to a suspension of hydroxylamine hydrochloride (34 g) in methanol (100 mL) at RT. Acetonitrile (20 g) was added and the mixture was heated at 60° C. for 15 hr. The mixture was cooled and the solvents evaporated, then 300 mL ethanol was added to the residue. The solid was filtered off and rinsed with 200 mL ethanol, then the filtrate was evaporated to a volume of 75 mL. The resulting precipitate was collected by filtration, rinsed with ethanol, then dried under vacuum to provide acetamide oxime 6a (19.5 g) as a white solid.

Also prepared by this method were:

6b: propionamide oxime and

6c: butyramide oxime.

Example 7

Synthesis of Reagent
2,2,2-trifluoro-N-hydroxy-acetamidine

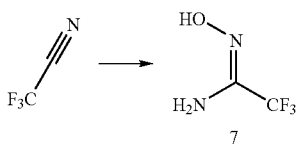

Step 7:

Sodium methoxide solution (35.9 mL of a 25% w/w solution in methanol) was added to a suspension of hydroxylamine hydrochloride (10.9 g) in methanol (200 mL) at RT.

The mixture was stirred for 10 min then filtered, and the solid was rinsed with methanol. The filtrate was cooled and stirred in an ice bath, then trifluoroacetonitrile gas (16.7 g) was bubbled into the solution over 30 min. The reaction mixture was allowed to warm to RT then was evaporated to a volume of 100 mL and filtered to remove solids. The filtrate was evaporated to provide a crude waxy solid (18 g). A portion of this was further purified by bulb-to-bulb vacuum distillation, affording Cmpd 7 as a tan waxy solid.

Example 8

Synthesis of Reagent
(S)-4,4,4-trifluoro-3-methyl-butyric acid ethyl ester

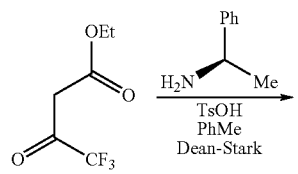

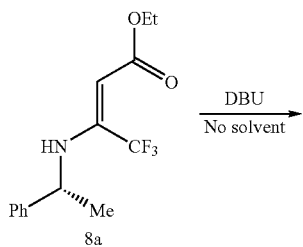

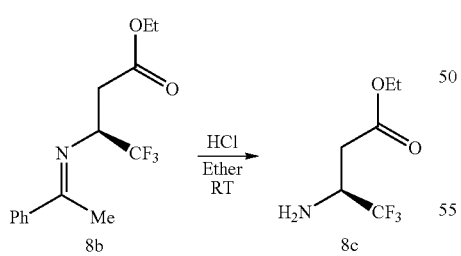

Step 8A:

(R)-alpha-methyl benzylamine (16.0 g) was added to a solution of ethyl 4,4,4-trifluorobutyrate (24.4 g) in toluene (75 mL). p-Toluenesulfonic acid hydrate (630 mg) was added, and the mixture was heated to reflux with removal of water via Dean-Stark trap. After 2 hr, the mixture was cooled, ethyl acetate (100 mL) was added, and the solution was washed with aq. sodium bicarbonate followed by brine. The organic layer was dried over sodium sulfate, filtered and evaporated to a yellow oil. The oil was subjected to vacuum distillation (collection at 102-110° C., ca. 5 mm Hg), providing 17.5 g of Cmpd 8a as a colorless oil.

Step 8B:

DBU (18.1 mL) was added to 8a (17.44 g), and the brown mixture was heated at 70° C. for 12 hr. The cooled mixture was applied to a plug of silica gel, eluting with 4:1 hexanes/ethyl acetate to provide Cmpd 8b (14.5 g) as a yellow oil.

Step 8C:

Hydrochloric acid (7.0 mL, 2N) was added to a solution of Cmpd 8b (800 mg) in ether (10 mL). The mixture was stirred vigorously at RT for 15 hr, then the layers were separated. The aqueous layer was washed three times with ether then was evaporated to dryness. The residue was co-evaporated twice with toluene, then dried under vacuum to provide Cmpd 8c (410 mg) as a gum.

Example 9

Synthesis of Reagent 3-amino-pentanoic acid methyl ester

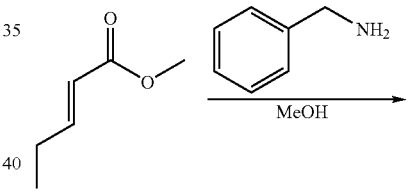

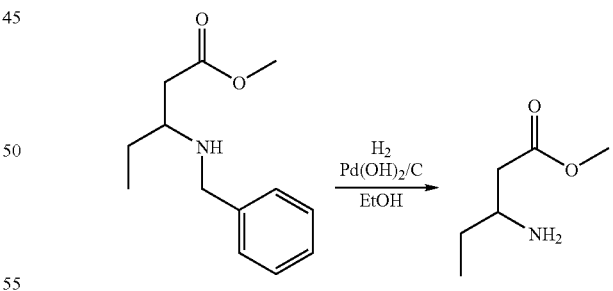

Step 9A:

Benzylamine (2.51 mL) was added to a solution of methyl trans-2-pentenoate (2.62 g) in methanol (10 mL). The reaction vessel was sealed and the solution was heated at 85° C. for 3 hr. The solvent was evaporated, and the residue was chromatographed on silica gel, eluting with 3:1 hexanes/ethyl acetate to provide 9a (2.9 g) as a yellow oil.

47

Step 9B:

A mixture of 9a (2.3 g), 20% palladium hydroxide on charcoal (530 mg), and ethanol (10 mL) was stirred at RT under a hydrogen atmosphere (1 atm, balloon) for 17 hr. The reaction mixture was sparged with nitrogen then filtered and evaporated. The residue was dissolved in DCM, dried over sodium sulfate, filtered and evaporated to provide Cmpd 9b (1.7 g) as a colorless oil, contaminated with approximately 20% of the corresponding ethyl ester.

Example 10

Synthesis of Reagent (S)-norvaline methyl ester hydrochloride

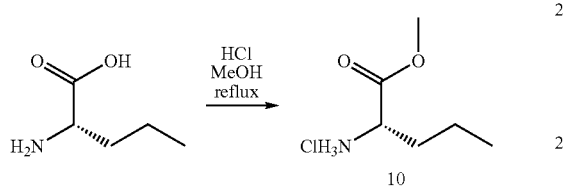

Step 10:

Acetyl chloride (3.0 mL) was added to methanol (60 mL) with stirring in an ice bath. (S)-norvaline (3.0 g) was added to the methanol solution, and the mixture was heated to reflux for 19 hr. The cooled solution was evaporated to dryness, then the residue was co-evaporated three times with toluene, then dried under vacuum to provide Cmpd 10 (4.3 g) as a white solid.

Example 11

Synthesis of [1-(3-cyclopropyl-[1,2,4]oxadiazol-5-yl)-propyl]-[3-(4-methoxy-2-methyl-phenyl)-2,5-dimethyl-pyrazolo[1,5-a]pyrimidin-7-yl]-amine

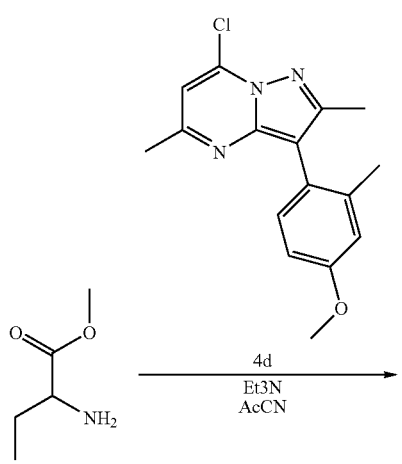

48

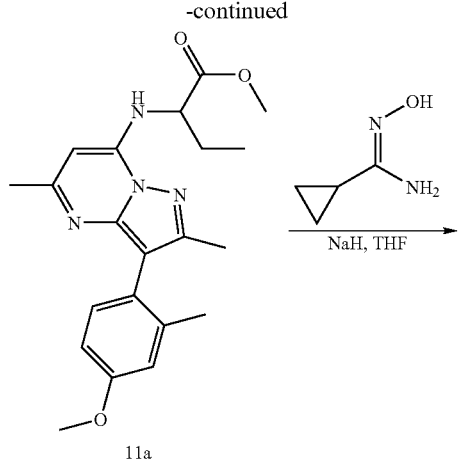

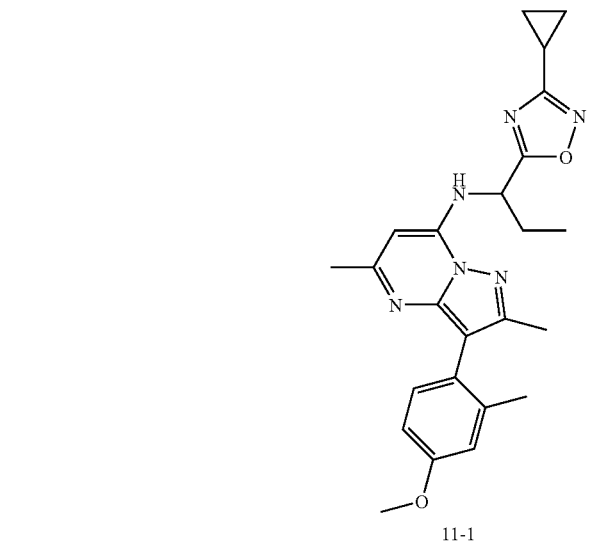

Step 11A:

(RS)-Methyl-2-aminobutyrate hydrochloride salt (0.81 g) was added to a solution of Cmpd 4d (0.800 g) in anhydrous acetonitrile (4 mL). Triethylamine (0.74 mL) was added, and the mixture was heated in a sealed tube in a microwave reactor at 150° C. for 35 min. The solvent was evaporated, then the crude residue was purified by silica gel chromatography using 2:1 hexanes/ethyl acetate as eluant to provide Cmpd 11a (0.585 g, 58%) as a slightly yellow solid.

Step 11B:

Sodium hydride (7 mg of a 60% suspension in mineral oil) was added to a suspension of N-Hydroxycyclopropanecarboxamidine (20 mg) in anhydrous THF (1 mL). The mixture was stirred at RT for 45 min, then a solution of 11a (50 mg) in anhydrous THF (0.5 mL) was added, and the mixture was heated at 75° C. for 1 hr. The mixture was cooled and concentrated, then the residue was purified by silica gel chromatography, using 2:1 hexanes/ethyl acetate as eluant to provide Cmpd 11-1 (20 mg) as a yellow oil.

Depending on the pyrazolo-[1,5a]-pyrimidine, amino acid ester and oxime reagent, the compounds in the following table were prepared:

TABLE 1
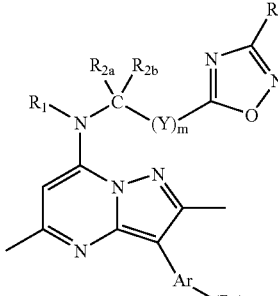
| Cmpd | | | MW | MS | $t_R$ | HPLC Method |
|---|---|---|---|---|---|---|
| 11-1 | 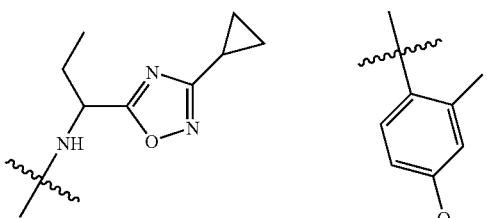 | | 432.52 | 433.0 | 5.81 | 1 |
| 11-2 | 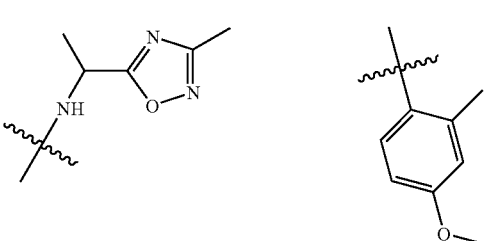 | | 392.46 | 393.0 | 4.75 | 3 |
| 11-3 | 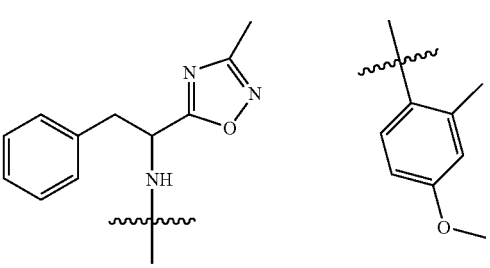 | | 468.56 | 469.2 | 6.122 | 1 |
| 11-4 | 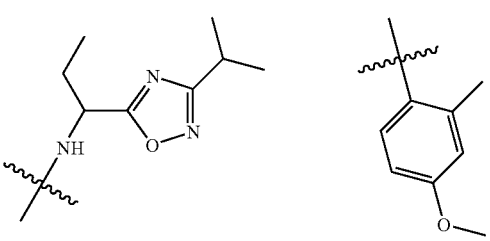 | | 434.54 | 435.1 | 6.022 | 1 |

TABLE 1-continued

| Cmpd | | | MW | MS | $t_R$ | HPLC Method |
|---|---|---|---|---|---|---|
| 11-5 | | | 420.51 | 421.0 | 5.629 | 1 |
| 11-6 | | | 378.43 | 379.0 | 4.316 | 1 |
| 11-7 | | | 404.47 | 405.0 | 5.086 | 1 |
| 11-8 | | | 406.49 | 407.0 | 5.291 | 1 |

TABLE 1-continued

| Cmpd | [R1N-C(R2a)(R2b)-(Y)m-oxadiazole-R5 group] | [Ar(R7)o group] | MW | MS | $t_R$ | HPLC Method |
|---|---|---|---|---|---|---|
| 11-9 | NH-CH(CH3)-CH2-(3-cyclopropyl-1,2,4-oxadiazol-5-yl) | 2-methyl-4-methoxyphenyl | 432.52 | 433.0 | 5.436 | 1 |
| 11-10 | NH-CH(CH3)-CH2-(3-methyl-1,2,4-oxadiazol-5-yl) | 2-methyl-4-methoxyphenyl | 406.49 | 407.0 | 4.761 | 1 |
| 11-11 | NH-CH(Et)-(3-CF3-1,2,4-oxadiazol-5-yl) | 2-methyl-4-methoxyphenyl | 460.46 | 461.0 | 6.444 | 1 |
| 11-12 | NH-C(cyclopropyl)(cyclopropyl fused)-(3-cyclopropyl-1,2,4-oxadiazol-5-yl) | 2-methyl-4-methoxyphenyl | 430.51 | 431.0 | 5.388 | 1 |

TABLE 1-continued

| Cmpd | | | MW | MS | $t_R$ | HPLC Method |
|---|---|---|---|---|---|---|
| 11-13 | | | 404.47 | 405.0 | 4.666 | 1 |
| 11-14 | | | 418.50 | 419.0 | 5.085 | 1 |
| 11-15 | | | 406.49 | 407.0 | 5.358 | 1 |
| 11-16 | | | 458.44 | 459.0 | 6.083 | 1 |

TABLE 1-continued
| Cmpd | 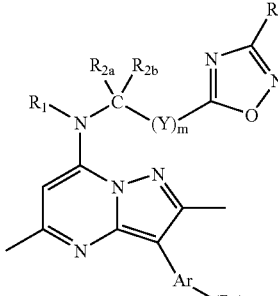 | 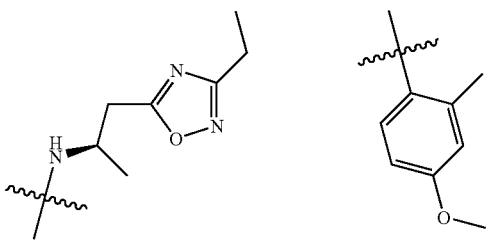 | MW | MS | $t_R$ | HPLC Method |
|---|---|---|---|---|---|---|
| 11-17 | | | 420.51 | 421.0 | 5.158 | 1 |
| 11-18 | | | 448.57 | 449.2 | 4.105 | 1 |
| 11-19 | | | 434.50 | 435.0 | 5.369 | 1 |
| 11-20 | | | 422.49 | 422.8 | 1.323 | 2 |

TABLE 1-continued
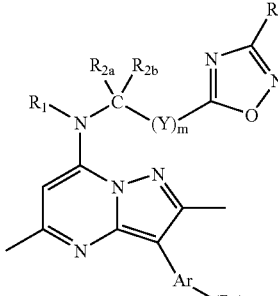
| Cmpd | (structure) | Ar(R7)o | MW | MS | $t_R$ | HPLC Method |
|---|---|---|---|---|---|---|
| 11-21 | 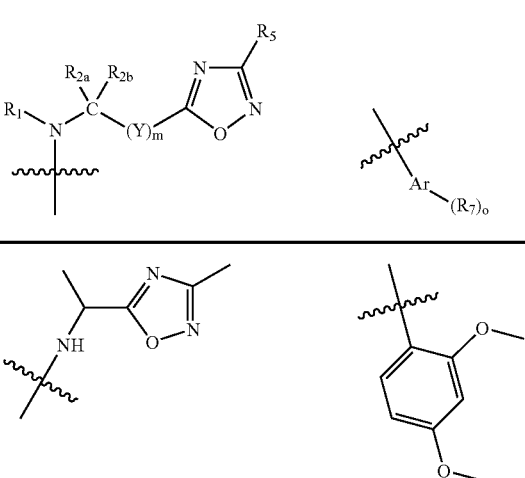 | 2,4-dimethoxyphenyl | 408.46 | 408.8 | 1.352 | 2 |
| 11-22 | 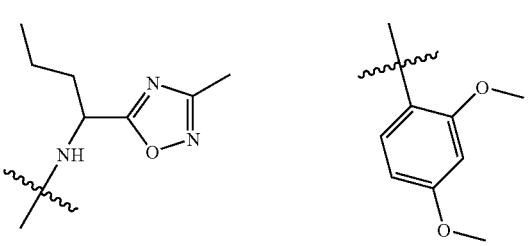 | 2,4-dimethoxyphenyl | 436.51 | 436.8 | 1.324 | 2 |
| 11-23 | 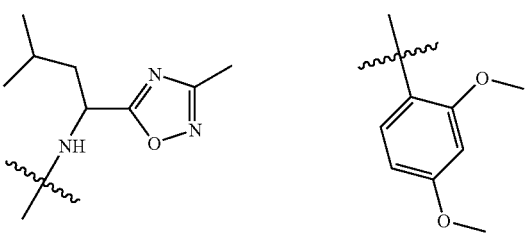 | 2,4-dimethoxyphenyl | 450.54 | 450.8 | 1.317 | 2 |
| 11-24 | 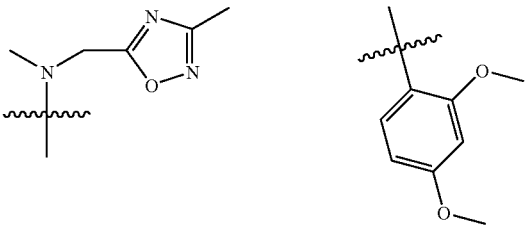 | 2,4-dimethoxyphenyl | 408.46 | 408.8 | 1.431 | 2 |

TABLE 1-continued
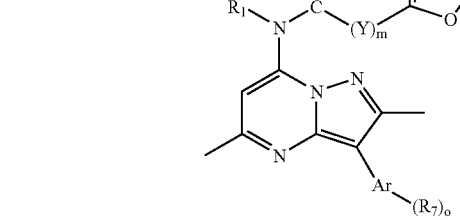
| Cmpd | (structure left) | (structure right) | MW | MS | $t_R$ | HPLC Method |
|---|---|---|---|---|---|---|
| 11-25 | benzyl-N-CH2-(3-methyl-1,2,4-oxadiazol-5-yl), methyl | 4-methyl-pyridin-2-yl-N(CH3)2 | 482.59 | 482.8 | 1.539 | 2 |
| 11-26 | 1-(3-methyl-1,2,4-oxadiazol-5-yl)propyl-NH, methyl | 2-methyl-4-methoxyphenyl | 406.49 | 407.2 | 19.23 | 1 |
Example 12
Synthesis Of [3-(4-methoxy-2-methyl-phenyl)-2,5-dimethyl-pyrazolo[1,5-a]pyrimidin-7-yl]-[1-methyl-2-(3-methyl-[1,2,4]oxadiazol-5-yl)-ethyl]-amine
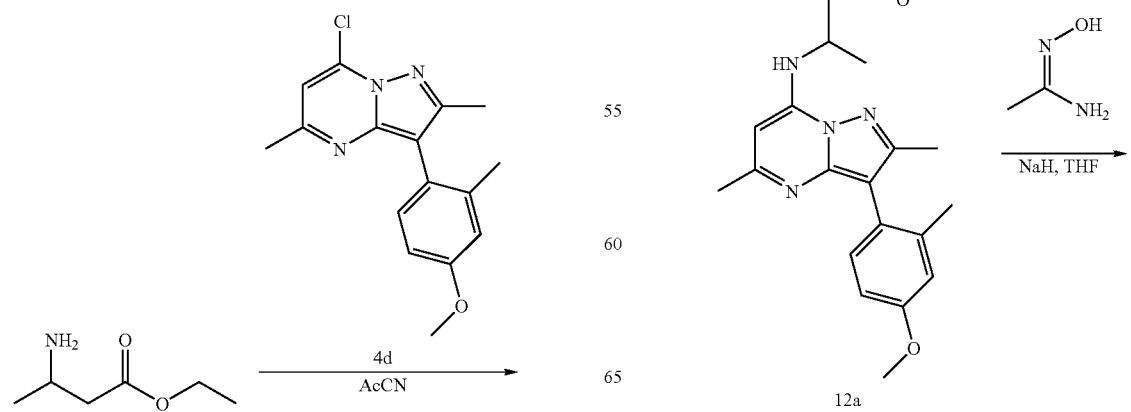
-continued -continued

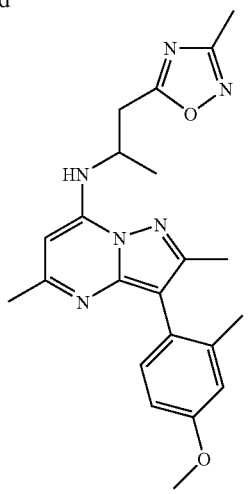

12-1

Step 12A:

(R,S)-Ethyl 3-aminobutyrate (150 mg) was added to a solution of 4d (150 mg) in anhydrous acetonitrile (0.75 mL). The mixture was heated in a sealed tube in a microwave reactor at 150° C. for 35 min. The solvent was evaporated, then the crude residue was purified by silica gel chromatography using 2:1 hexanes/ethyl acetate as eluant to provide Cmpd 12a (170 mg, 76%) as a yellow oil.

Step 12B:

Sodium hydride (21 mg of a 60% suspension in mineral oil) was added to a suspension of acetamide oxime (60 mg) in anhydrous THF (2 mL) at RT. The mixture was stirred at RT for 45 min, then a solution of 12a (160 mg) in anhydrous THF (1.6 mL) was added, the reaction vessel was sealed and the mixture was heated at 80° C. for 1.5 hr. The mixture was cooled and concentrated, then the residue was purified by silica gel chromatography, using 1:1 hexanes/ethyl acetate as eluant to provide 12-1 (72 mg) as a dark yellow oil.

Depending on the pyrazolo-[1,5a]-pyrimidine, amino acid ester and oxime reagent, the compounds in the following table were prepared:

TABLE 2

| Cmpd | R group | Ar group | MW | MS | $t_R$* |
|---|---|---|---|---|---|
| 12-1 | | | 406.49 | 407.0 | 4.831 |
| 12-2 | | | 468.56 | 469.0 | 6.558 |

TABLE 2-continued
| Cmpd | 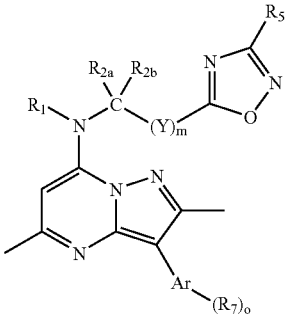 | 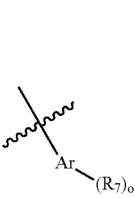 | MW | MS | t_R* |
|---|---|---|---|---|---|
| 12-3 | 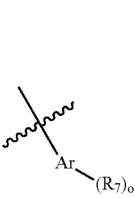 | 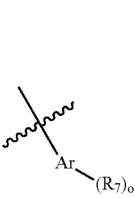 | 460.46 | 461.0 | 4.676 |
| 12-4 | 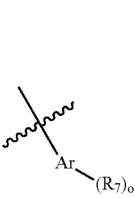 | 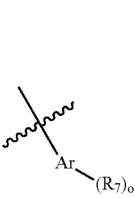 | 432.52 | 433.0 | 4.544 |
| 12-5 | 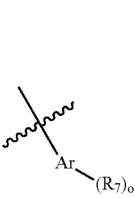 | 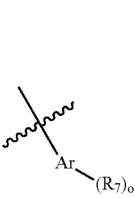 | 434.54 | 435.1 | 4.687 |

TABLE 2-continued

| Cmpd | | | MW | MS | $t_R$* |
|---|---|---|---|---|---|
| 12-6 | 3-cyclopropyl-oxadiazole-propylamine | 2-methyl-4-methoxyphenyl | 432.52 | 433.1 | 4.726 |
| 12-7 | 3-isopropyl-oxadiazole-propylamine | 2-methyl-4-methoxyphenyl | 434.54 | 435.1 | 4.961 |
| 12-8 | 3-methyl-oxadiazole-propylamine | 2-methyl-4-methoxyphenyl | 406.49 | 407.0 | 4.541 |

TABLE 2-continued
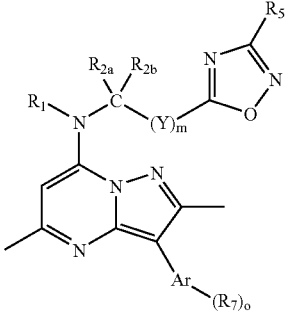
| Cmpd | | | MW | MS | $t_R$* |
|---|---|---|---|---|---|
| 12-9 | 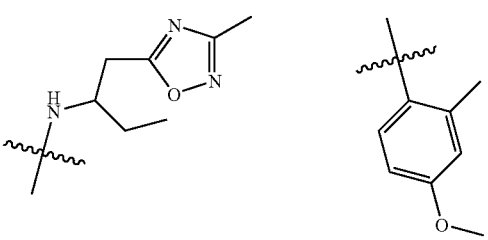 | | 420.51 | 421.1 | 5.022 |
| 12-10 | 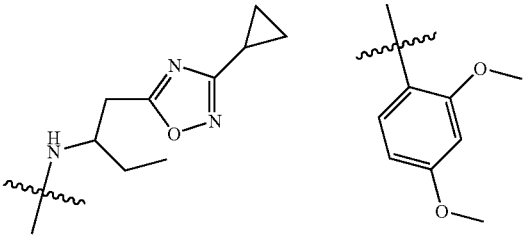 | | 462.55 | 463.0 | 5.714 |
| 12-11 | 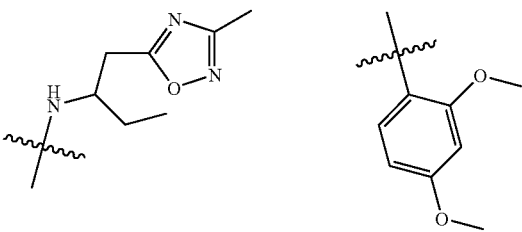 | | 436.51 | 437.0 | 5.050 |
*All HPLC employed Analytical Method 1.

Example 13

Synthesis of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-butyl]-amine

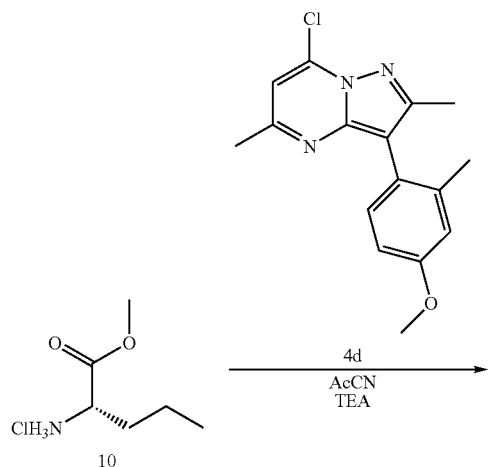

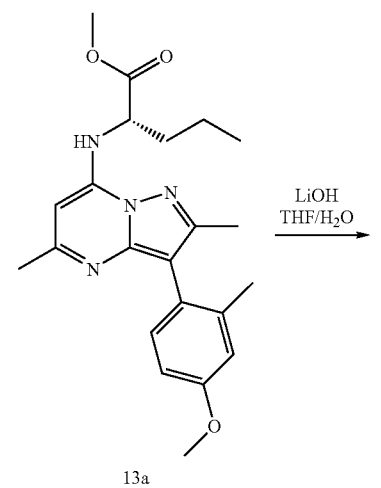

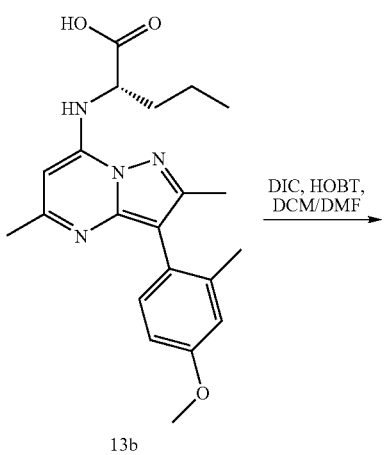

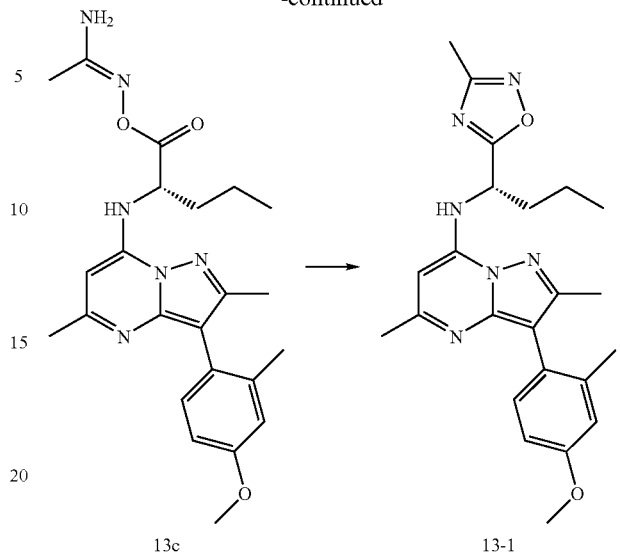

Step 13A:

A mixture of compounds 10 (416 mg) and 4d (500 mg), triethylamine (0.35 mL) and acetonitrile (4 mL) was heated at 150° C. in a microwave reactor for 35 min. The mixture was partitioned between ethyl acetate and aq. sodium bicarbonate, then the organic layer was dried over sodium sulfate, filtered, and concentrated. The residue was chromatographed on silica gel, eluting with 4:1 hexanes/ethyl acetate to provide 13a (340 mg) as a yellow oil.

Step 13B:

Lithium hydroxide hydrate (44 mg) was added to a mixture of Cmpd 13a (320 mg), THF (2 mL), and water (1 mL). The mixture was stirred vigorously at RT for 30 min, then hexanes (5 mL) was added. The layers were separated and the aqueous layer was acidified with 2N hydrochloric acid (0.6 mL, final pH 3-4). The resulting precipitate was collected by filtration, washed with water, co-evaporated with toluene, then dried under vacuum to provide Cmpd 13b (215 mg) as a white solid.

Step 13C:

A mixture of 13b (160 mg), HOBT (79 mg), acetamide oxime (47 mg), DCM (2 mL), and DMF (0.25 mL) was cooled to −15° C. DIC (0.085 mL) was added and the mixture was allowed to warm to RT over 2 hr. The solvents were evaporated, then ethyl acetate (50 mL) was added and the mixture was washed once with saturated aq. sodium bicarbonate, then once with 10% aq. potassium dihydrogen phosphate. The ethyl acetate layer was dried over sodium sulfate, filtered, and concentrated to provide Cmpd 13c.

Step 13D:

Pyridine (1.5 mL) was added to Cmpd 13c prepared in the previous step, then the mixture was heated in a sealed tube at 100° C. for 2.5 hr. The solvent was evaporated. The residue was taken up in ether then filtered to remove DIU, rinsing with several portions of ether. The filtrate was evaporated, then the residue was chromatographed on silica gel, eluting with 3:1 hexanes/ethyl acetate to provide Cmpd 13-1 as a yellow oil. The free base 13-1 (115 mg) was dissolved in ether (2 mL), then 2 M HCl in ether (0.205 mL) was added at RT, resulting in formation of a white precipitate. The supernatant was decanted, the remaining solid was washed twice with ether. Drying under vacuum at 35° C. gave 13-1 hydrochloride salt (121 mg) as a white solid.

Depending on the pyrazolo-[1,5a]-pyrimidine, amino acid ester and oxime reagent, the compounds in the following table were prepared:

TABLE 3
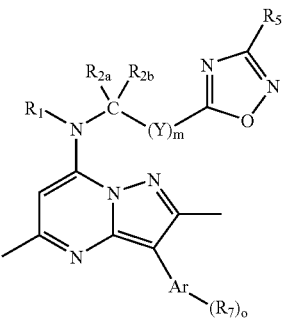
| Cmpd | | | MW | MS | $t_R$ | HPLC Method |
|---|---|---|---|---|---|---|
| 13-1 | 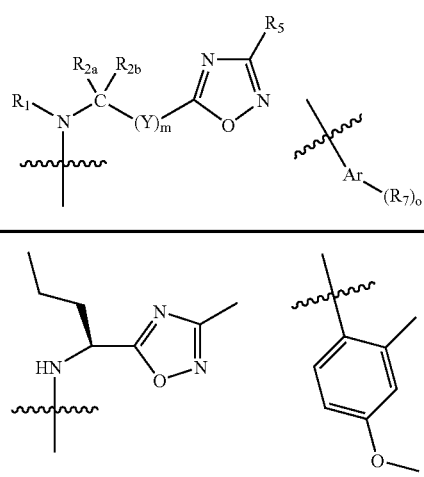 | | 420.51 | 421.1 | 20.990 | 3 |
| 13-2 | 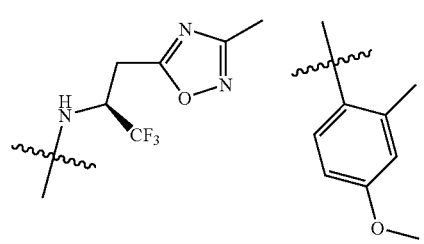 | | 460.46 | 461.1 | 5.440 | 1 |
| 13-3 | 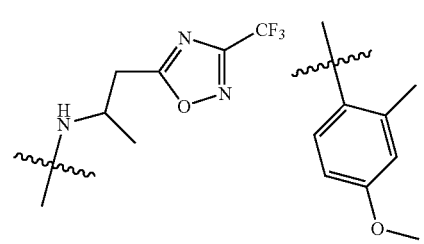 | | 460.46 | 461.0 | 5.991 | 1 |

TABLE 3-continued

| Cmpd | | | MW | MS | $t_R$ | HPLC Method |
|---|---|---|---|---|---|---|
| 13-4 | (oxadiazole-CH3, NH-CH(CF3)-CH2-) | (2-Cl, 4-OMe phenyl) | 480.88 | 481.1 | 14.033 | 3 |
| 13-5 | (oxadiazole-CF3, NH-CH(CH3)-CH2-) | (2-Me, 4-OMe phenyl) | 460.46 | 461.1 | 5.458 | 1 |
| 13-6 | (oxadiazole-CF3, NH-CH(CH3)-CH2-) | (2-Cl, 4-OMe phenyl) | 480.88 | 480.7 | 6.215 | 1 |

TABLE 3-continued
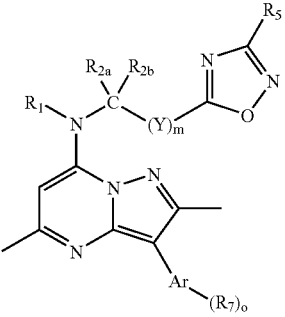
| Cmpd | R1N(R2a)(R2b)C(Y)m- | Ar(R7)o | MW | MS | $t_R$ | HPLC Method |
|---|---|---|---|---|---|---|
| 13-7 | | | 476.46 | 477.1 | 13.596 | 3 |
| 13-8 | | | 476.46 | 477.0 | 5.115 | 1 |
| 13-9 | | | 530.43 | 530.7 | 6.288 | 1 |

Example 14

Synthesis of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine

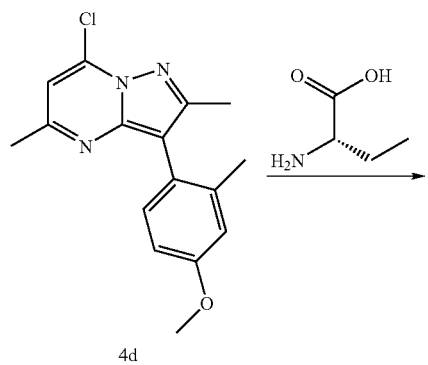

4d

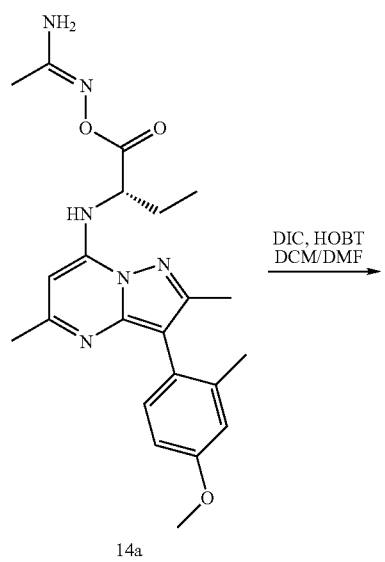

14a

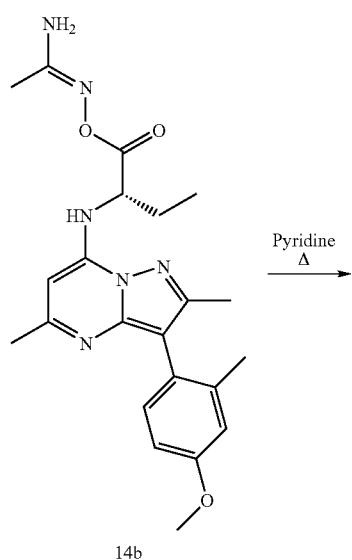

14b

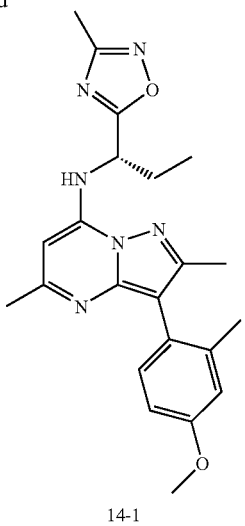

14-1

Step 14A:

A suspension of sodium bicarbonate (28.7 g) and (S)-2-aminobutyric acid (21.7 g) in water (250 mL) was added to a solution of 4d (39.7 g) in dioxane (250 mL). The mixture was stirred and heated to reflux (102° C. bath) for 14 hr. The mixture was cooled to RT, then concentrated HCl (16 mL) was added over 10 min to final pH 4.5. A copious white precipitate formed. The mixture was concentrated to a weight of about 250 g, then the residue was subjected to co-evaporation with several portions of ethyl acetate, resulting in a thick, pasty aqueous slurry. The mixture was filtered, and the filter cake was washed with water (total 350 mL). The filter cake was then dried under vacuum at 35° C., yielding compound 14a (45.2 g) as a white solid.

Alternate Step 14A:

$NaHCO_3$ (97.45 g, 1.16 mol) and (S)-2-aminobutyric acid (74.25 g, 0.72 mol) were suspended in water (900 mL). To this was added a solution of chloropyrimidine 4d (134.4 g) in dioxane (900 mL) and the resulting mixture warmed to reflux and stirred for 2.5 h. The mixture was cooled to rt, and acidified to pH 4 with adding conc. HCl (approx 88 mL) dropwise forming a copious white precipitate. The mixture was concentrated in vacuo and the resulting solid slurried in water (1 L), stirred and filtered, washing with water. More product precipitate was observed from the mother liquors and two more crops were obtained. The combined solids were dried in vacuo to give to desired carboxylic acid 14a as a cream colored solid (159.3 g, 0.4 mol, >93% purity). In an alternate workup, the reaction mixture is filtered immediately following acidification with the conc. HCl and the solid is dissolved in methylene chloride. The remaining water in the solid was separated and removed and the methylene chloride layer was dried and concentrated to give 14a.

Step 14B:

Cmpd 14a (10 g) was suspended in toluene (50 mL) and evaporated to dryness. Dry DCM (100 mL) was added followed by HOBT (4.8 g) and acetamide oxime (2.7 g). Anhydrous DMF (11 mL) was added, then the reaction mixture was stirred and cooled in an ethylene glycol/dry ice bath to an internal temperature of −15.5° C. under a nitrogen atmosphere. DIC (5.3 mL) was then added via syringe. The reaction mixture was stirred and allowed to warm over 2 hr, at which time the internal temperature was +16.5° C. The solvents were evaporated, then ethyl acetate (150 mL) was added and the mixture was washed once with 10% aq. potassium dihydrogen phosphate, twice with saturated aq. sodium bicarbonate, once again with 10% aq. potassium dihydrogen phosphate, and finally with brine. The ethyl acetate layer was dried over sodium sulfate, filtered, and concentrated to provide crude Cmpd 14b.

Alternate Step 14B:

Compound 4a (411.91 g, 0.95 mol) was suspended in $CH_2CH_2$ (3.8 L) and DMF (300 mL), to which was added acetamidoxime (95.12 g, 1.28 mol) and HOBt (167.56 g, 1.24 mol) under a nitrogen atmosphere. The mixture was cooled to an internal temperature of –30° C. and DIC (194.15 mL, 1.24 mol) was added dropwise so as to maintain the temperature below –20° C. The reaction was stirred at this temperature for 1 hour and subsequently allowed to warm to 10° C. over the next 3 hours. The mixture was concentrated in vacuo and redissolved in EtOAc (5 L). The EtOAc solution was washed with $NaHCO_3$ (3×1.5 L, sat. aq.), $KH_2PO_4$ (1500 mL, 1M), brine (2×1.5 L), dried ($MgSO_4$) and concentrated in vacuo to give 14b as a yellow foam.

Step 14C:

Pyridine (50 mL) was added to Cmpd 14b from Step 14B, then the mixture was heated under nitrogen at 100° C. for 4 hr. The resulting solution was allowed to cool, the solvent was evaporated, and the residue was co-evaporated twice with ethyl acetate and once with heptane. The residue was taken up in 50 mL ether, then filtered to remove DIU, rinsing with several portions of ether. The filtrate was evaporated, then the residue was chromatographed on silica gel, eluting with 2:1 hexanes/ethyl acetate to provide the partially purified Cmpd 14-1 as a slightly yellow foam. The foam was co-evaporated twice with heptane, then 5:1 heptane/ethyl acetate (60 mL) was added, and the resulting slurry was stirred at RT for 24 hr. The solid was filtered and rinsed with hexanes, providing 14-1 free base (7.3 g) as a white solid. The filtrate was concentrated and a second crop of 14-1 free base (0.7 g) was collected, also as a white solid.

The free base 14-1 (6.0 g) was dissolved in 80 mL acetone and cooled in an ethylene glycol/dry ice bath to –12° C. (internal). Hydrogen chloride (8.9 mL of a 2.0 M solution in ether) was added in one portion. The clear yellow solution was stirred for 1 min, then the solvent was evaporated. The residue was co-evaporated with two portions of acetone, then dried under vacuum to produce an amber foam. The foam was pulverized and then dried under vacuum at RT for 24 hr, providing the hydrochloride salt 14-1 (6.7 g) as an amorphous tan powder.

Alternate Step 14C:

Compound 4b from alternate Step 14B was dissolved in pyridine (1.8 L), warmed to 100° C., stirred for 2 hours and then was concentrated in vacuo to give a brown viscous oil. Purification by flash chromatography eluting with EtOAc: hexane (1:9, 2:8, 3:7, 4:6) gave a cream colored solid. This solid was slurried in heptane (4 L) and ground to a fine powder by stirring to give 14-1 as a white crystalline solid (248.5 g, 98.3% purity).

Depending on the pyrazolo-[1,5a]-pyrimidine, amino acid ester and oxime reagent, the compounds in the following table were prepared:

TABLE 4

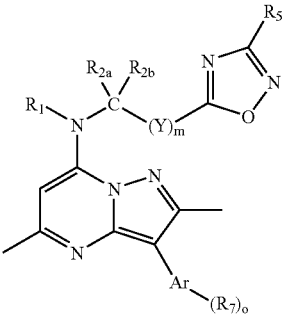

| Cmpd | | Ar(R7)o | MW | MS | $t_R$ |
|---|---|---|---|---|---|
| 14-1 | | | 406.49 | 407.0 | 4.915 |

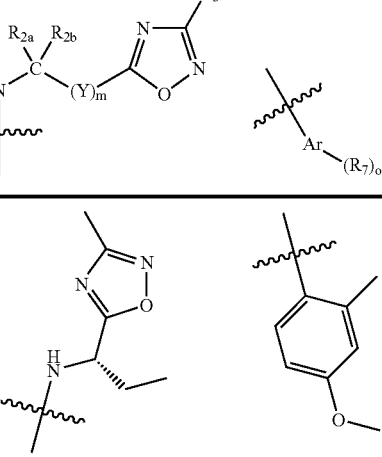

TABLE 4-continued

| Cmpd | | | MW | MS | $t_R$ |
|---|---|---|---|---|---|
| 14-2 | | | 406.49 | 407.0 | 4.82 |
| 14-3 | | | 432.52 | 433.1 | 4.987 |
| 14-4 | | | 426.91 | 427.0 | 20.71 |

Example 14A

Characterization of Polymorph Form 1 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine Free Base 14-1 prepared as shown in alternate Step 14C affording 248.5 g of 14-1 may be characterized by, for example, X-Ray powder diffraction spectrometry, Raman spectrometry and/or Differential Scanning Calorimetry (DSC). Free base of 14-1 shows the XPRD pattern of FIG. 1 and was identified as polymorph Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

Table 1 shows the XRPD angles and d spacings for polymorph Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

TABLE 1

X-Ray Powder Diffraction Spectral Lines of Polymorph Form 1

| degree 2-θ | d value Angstrom |
|---|---|
| 6.721 | 13.1397 |
| 8.361 | 10.5663 |
| 10.698 | 8.26247 |
| 11.757 | 7.52055 |
| 13.323 | 6.64016 |
| 15.112 | 5.85779 |
| 15.492 | 5.71491 |
| 15.959 | 5.54892 |
| 18.222 | 4.86461 |
| 18.965 | 4.67554 |
| 20.291 | 4.37294 |
| 21.428 | 4.14338 |
| 21.974 | 4.04163 |
| 22.664 | 3.92018 |
| 24.002 | 3.70457 |
| 25.082 | 3.54736 |
| 26.268 | 3.38993 |
| 26.941 | 3.30677 |
| 30.544 | 2.92437 |
| 31.289 | 2.85642 |

The X-ray powder diffraction pattern of polymorph Form 1 as shown in FIG. 1 exhibits predominant peaks (expressed in degrees 2θ (+/−0.15 degrees 2θ) at one or more of the following positions: 6.721, 11.757, 13.323, 18.222, 21.426 and 21.974. More specifically, such characteristic peaks are at 11.757 and 21.974, and further at 6.721 and further at 13.323, 18.222, and 21.426.

Description of Figures

FIG. 1 shows X-Ray powder diffraction data obtained for polymorph Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine as described before. Form 1 is characterised by having an XRPD pattern with signals substantially as listed in Table 1.

Figure 2:
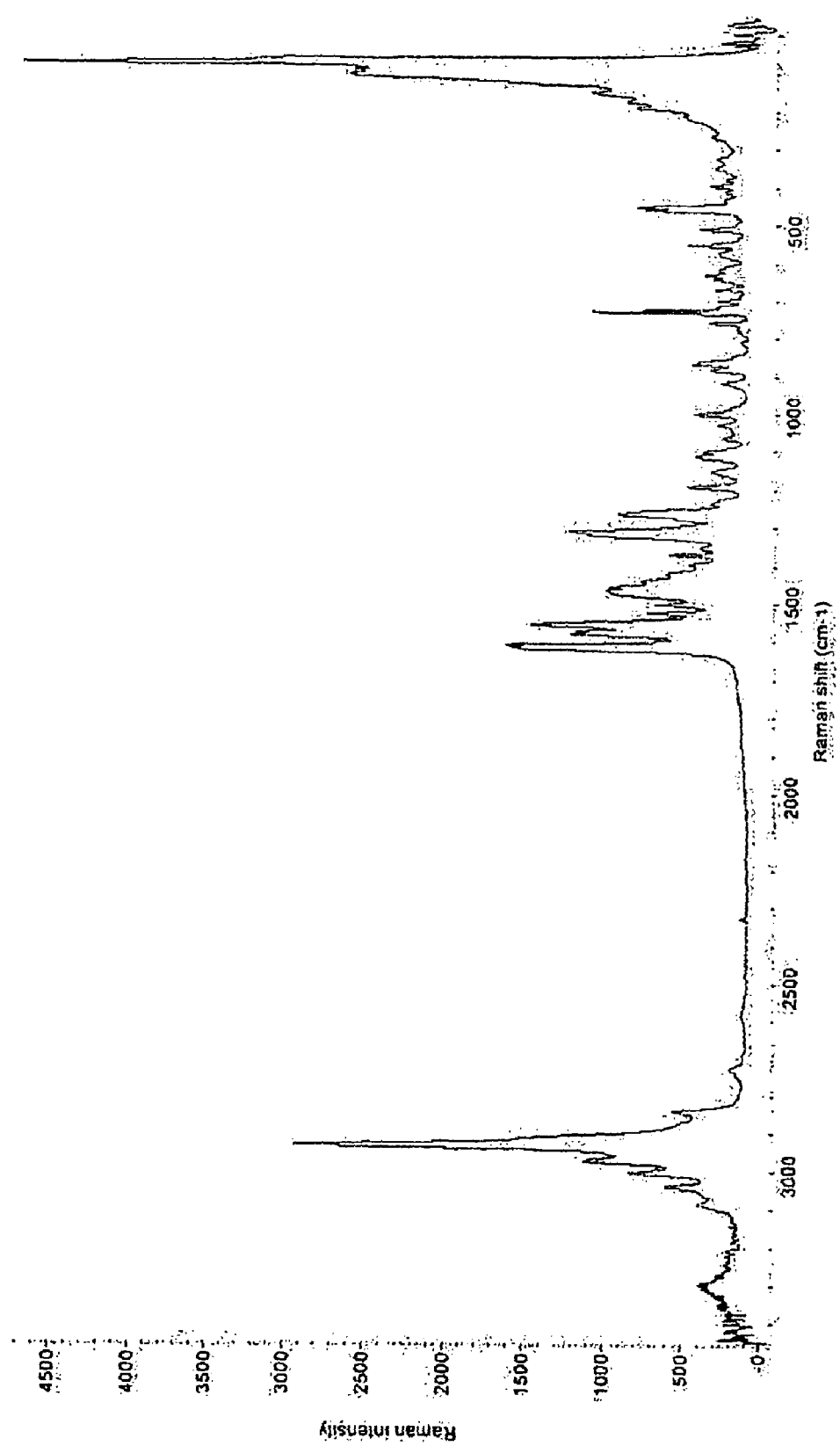
FIG. 2 shows the Raman spectrum of polymorph Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

FIG. 2 shows the Raman spectrum of polymorph Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

Figure 3:
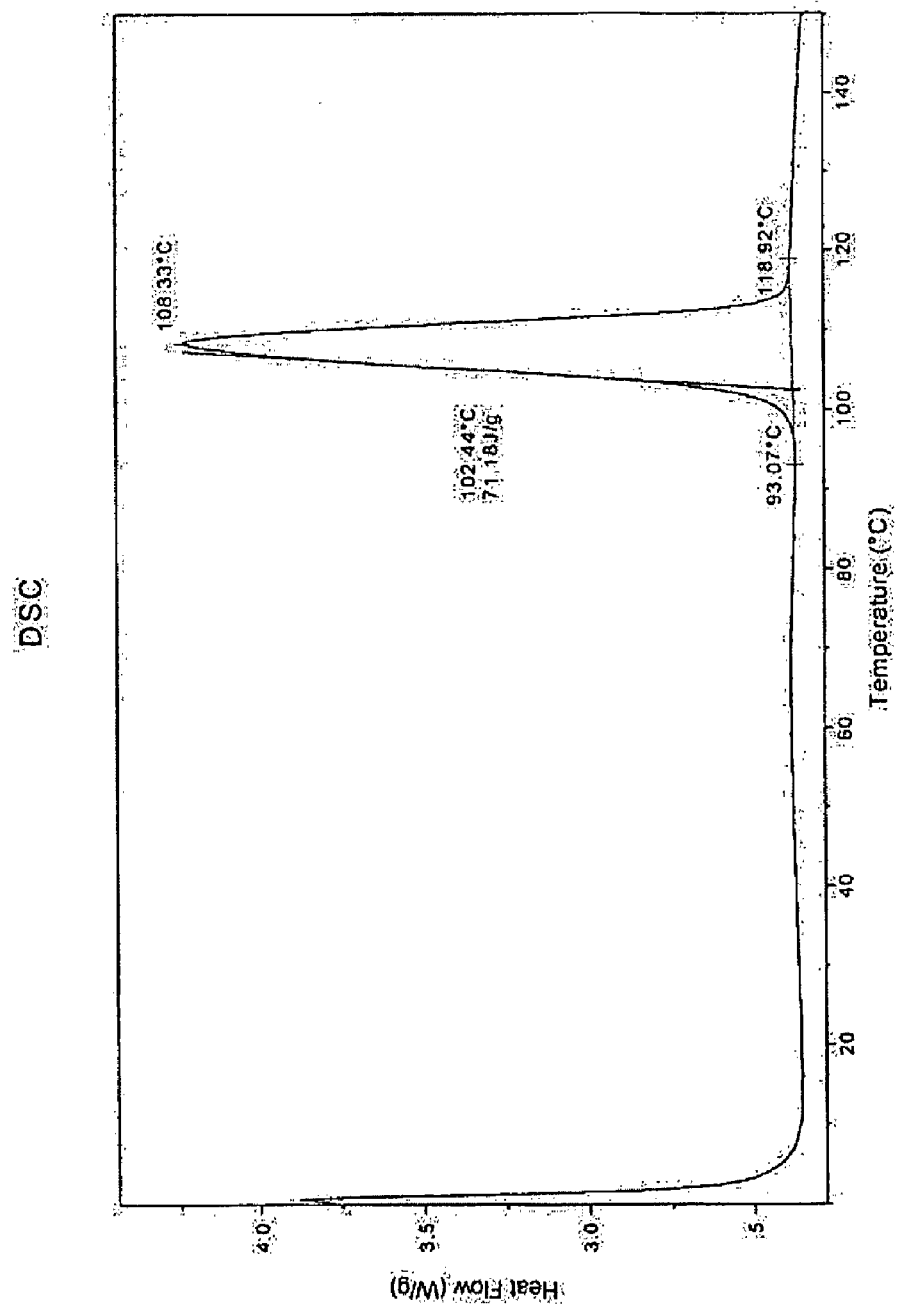
FIG. 3 shows a Differential Scanning Calorimetry (DSC) thermogram of polymorph Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

FIG. 3 shows a Differential Scanning Calorimetry (DSC) thermogram of polymorph Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

It will be recognised that spectra and diffraction data will vary slightly according to various factors such as the temperature, concentration and instrumentation used. The skilled person will recognise that XRPD peak positions are affected by differences in sample height. The peak positions quoted herein are thus subject to a variation of +/−0.15 degrees 2-theta.

As shown in FIG. 3, the polymorph Form 1 exhibits a predominant endotherm peak at about 108.3° C. It should be recognized that that the endotherm peak as measured is dependent under a number of factors including the machine employed, the rate of heating, the calibration standard, humidity and the purity of the sample used. Accordingly, the term "about 108.30° C." is intended to encompass such instrument variations.

X-Ray Powder Diffraction

X Ray Powder Diffraction (XRPD) analysis was performed on Bruker D5005, using Sol-X detector. The acquisition conditions were: radiation: Cu Kα, generator tension: 40 kV, generator current: 50 mA, start angle: 2.0° 2θ, end angle: 45.0° 2θ, step size: 0.02° 2θ, time per step: 0.5 seconds. The sample was prepared on zero background sample holder.

Raman Spectroscopy

Instrument Configuration: Kaiser RXN1 Kaiser Optical System Micro Raman. Sample on Al sample pan, laser 1=785 nm.

Differential Scanning Calorimetry (DSC)

Instrument configuration: PE DSC 7, not ermetic sample pan, run @10 K/min to 150° C., sample 1.5-5 mg.

Example 14B

Synthesis and Characterisation of Polymorph Form 2 of [3-(4-methoxy-2-methyl-phenyl)-2,5-dimethyl-pyrazolo[1,5-a]pyrimidin-7-yl]-[(S)-1-(3-methyl-[1, 2,4]oxadiazol-5-yl)-propyl]-amine Polymorph Form 2 of [3-(4-Methoxy-2-methyl-phenyl)-2, 5-dimethyl-pyrazolo[1,5-a]pyrimidin-7-yl]-[(S)-1-(3-methyl-[1,2,4]oxadiazol-5-yl)-propyl]-amine was prepared as follows:

[3-(4-Methoxy-2-methyl-phenyl)-2,5-dimethyl-pyrazolo [1,5-a]pyrimidin-7-yl]-[(S)-1-(3-methyl-[1,2,4]oxadiazol-5-yl)-propyl]-amine polymorph Form 1 (0.74 g) was slurried in 50% aqueous isopropanol (4 mL). The temperature was cycled between 0 and 40° C. for 24 hours, then the mixture stirred at ambient temperature for 3 days, then the temperature was cycled between 0 and 40° C. for 24 hours. The residual solid was filtered off and dried at ambient temperature to give 0.70 g of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine polymorph Form 2.

Preparation of polymorph Form 0.2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine was repeated on large scale as follows.

Free Base 14-1 was prepared in an analogous way as described before in EXAMPLE 14, except for the lack of the chromatographic purification present in Step 14C. The formation and successive liberation of the mesylate salt afforded a desired compound with a high purity without the necessity of a chromatography.

Free Base 14-1 (2.48 kg, 6.10 mol, chemical purity 90%) was stirred with n-Butyl acetate (12.5 L) for 30 to 45 minutes then Methane sulphonic acid (1.2 eq, 7.32 Mol, 703 g) was added. After stirring for 2-3 hrs at 25-30° C. the mixture was filtered. The solid was slurry washed with n-Butyl acetate (5 L) followed by Heptane (7.5 L) then dried for 4-6 hrs at 50±5° C. under vacuum to give Mesylate salt (2.48 kg, chemical purity 97.37%).

The mesylate salt was stirred with DM water (12.5 L) for 15 to 30 minutes. Aq. ammonia was added to a pH of 9.0-10. The suspension was extracted with ethyl acetate (3×7.5 L) then the combined extracts were washed with DM water (5 L) and 20% Brine solution (5 L). The organic solution was concentrated under vacuum at below 50±5° C., removing 85 to 90% of the solvent, then the residue cooled to 30±5° C. Heptane (15 L) was added and the mixture stirred for 2 to 3 hrs at 25-30° C. then 60 to 70% of the solvent was distilled off under vacuum at below 50±5° C. The mixture was cooled to 30±5° C., stirred for 1 to 2 hours, then filtered. The solid was slurry washed with Heptane (5 L) then dried under vacuum at below 50±5° C. to give polymorph Form 1 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine (1.70 kg, chemical purity 99.34%).

A mixture of polymorph Form 1 (1.37 kg, 3.37 Mol, purity by HPLC 99.34%) of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine and ethyl acetate (2.05 L) were heated to 40 to 45° C. (a clear solution was observed). The solution was then cooled to 30±5° C. and Heptane (6.85 L) added before heating to 60±2.5° C. Polymorph Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine seed material prepared as described above (0.5% w/w) was added at 60±2.5° C. then the mixture was cooled to 40±2.5° C., then heated back to 50±2.5° C. when further seed material (0.5% w/w) was added. The resulting slurry was cooled to 30±5° C. and stirred for 12 hrs at 30±5° C. Heptane (2.74 L) was added and the mixture stirred for a further 12 hrs at 30±5° C. The slurry was filtered and the solid slurry washed with Heptane (2.74 L). The solid was dried under vacuum at 50±5° C. for 8 hrs to give 0.97 kg of polymorph Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine (HPLC purity 99.58%).

| HPLC method | |
|---|---|
| Column: | Zorbax SB-C18 (150 × 4.6 mm), 3.5 micron |
| Mobile Phase-A: | 0.05% TFA (Aqueous) |
| Mobile Phase-B: | 0.025% TFA (Acetonitrile) |
| Column temperature: | 40° C. |
| Flow rate: | 1.0 ml/min |
| Wavelength of detection: | 225 nm |
| Injection volume: | 5 μl |
| Run time: | 30 mins |
| Concentration: | 0.3 mg/ml |
| Gradient program: | Linear gradient |

| Time in min | Mobile phase-A (%) | Mobile phase-B (%) |
|---|---|---|
| 0 | 75 | 25 |
| 25 | 5 | 95 |
| 29 | 5 | 95 |
| 30 | 75 | 25 |

| | |
|---|---|
| Post run time: | 5 min |
| Retention time: | Form 2 about 9 min |
| Diluent: | Mobile Phase-A:Mobile Phase-B (1:1) |

Polymorph Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine shows the XPRD pattern (FIG. 4).

Table 2 shows the XRPD angles and d spacings for polymorph Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

TABLE 2

X-Ray Powder Diffraction Spectral Lines of Polymorph Form 1

| degree 2-θ | d value Angstrom |
|---|---|
| 10.415 | 8.48651 |
| 12.125 | 7.29347 |
| 12.36 | 7.15526 |
| 13.177 | 6.7136 |
| 13.527 | 6.5406 |
| 15.121 | 5.85426 |
| 16.045 | 5.51918 |
| 16.331 | 5.42339 |
| 19.457 | 4.55852 |
| 20.133 | 4.40682 |
| 20.2941 | 4.2386 |
| 21.28 | 4.1718 |
| 22.239 | 3.99412 |
| 22.823 | 3.89318 |
| 23.51 | 3.78098 |
| 24.714 | 3.59933 |
| 25.488 | 3.49186 |
| 26.261 | 3.39074 |
| 27.858 | 3.19988 |
| 29.537 | 3.02169 |

DESCRIPTION OF FIGURES

FIG. 4 shows X-Ray powder diffraction data obtained for polymorph Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine as described before. Form 2 is characterised by having an XRPD pattern with signals substantially as listed in Table 1.

Figure 5:
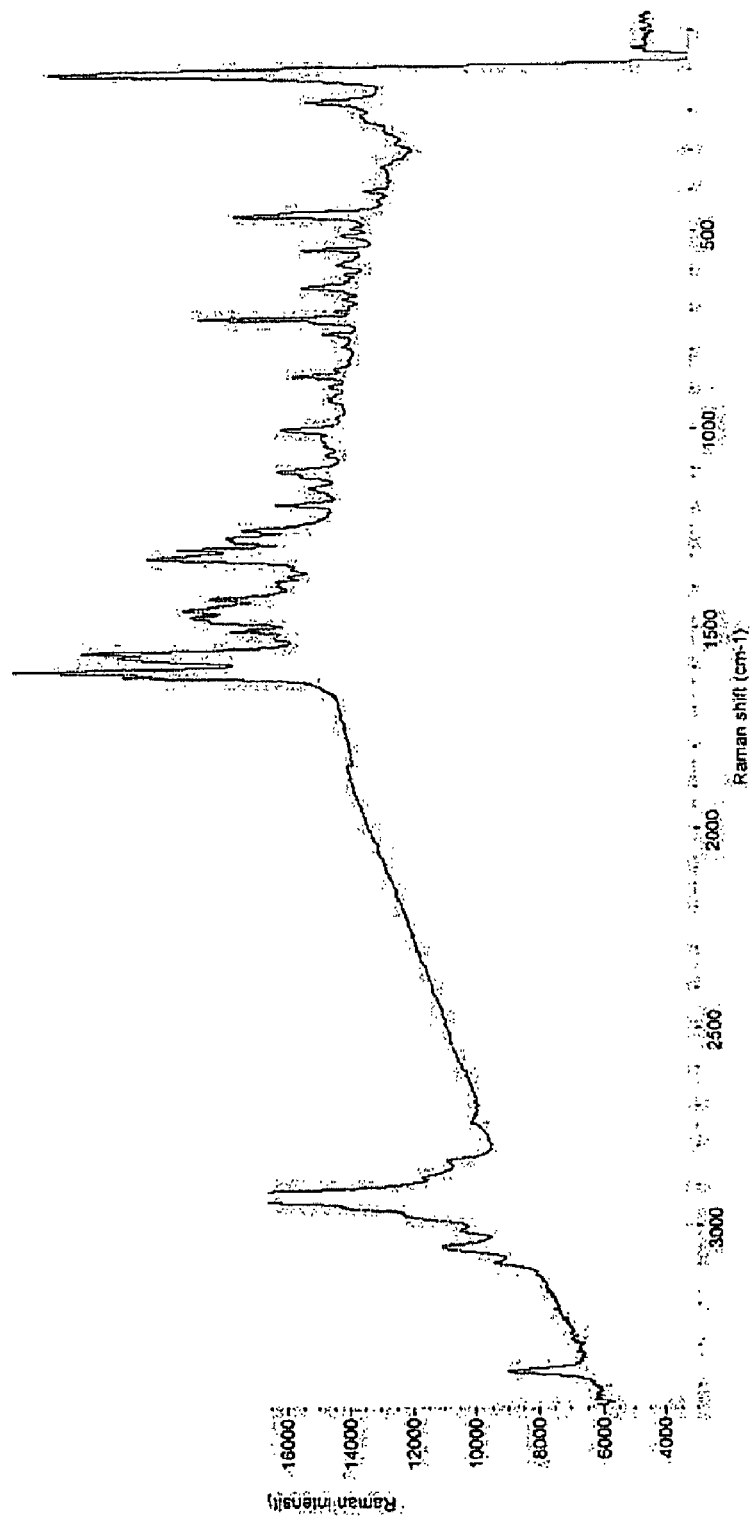
FIG. 5 shows the Raman spectrum of polymorph Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

FIG. 5 shows the Raman spectrum of polymorph Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

FIG. 6 shows a Differential Scanning Calorimetry (DSC) thermogram of polymorph Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

It will be recognised that spectra and diffraction data will vary slightly according to various factors such as the temperature, concentration and instrumentation used. The skilled person will recognise that XRPD peak positions are affected by differences in sample height. The peak positions quoted herein are thus subject to a variation of +/−0.15 degrees 2-theta.

As shown in FIG. 6, the polymorph Form 2 exhibits a predominant endotherm peak at about 115.1° C. It should be recognized that that the endotherm peak as measured is dependent under a number of factors including the machine employed, the rate of heating, the calibration standard, humidity and the purity of the sample used. Accordingly, the term "about 115.1° C." is intended to encompass such instrument variations.

X-Ray Powder Diffraction

X Ray Powder Diffraction (XRPD) analysis was performed on Bruker D5005, using Sol-X detector. The acquisition conditions were: radiation: Cu Kα, generator tension: 40 kV, generator current: 50 mA, start angle: 2.0° 2θ, end angle:

89

45.0° 2θ, step size: 0.04° 2θ, time per step: 1 second. The sample was prepared on zero background sample holder.

Raman Spectroscopy

Instrument Configuration: Kaiser RXN1 Kaiser Optical System Micro Raman. Sample on Al sample pan, laser 1=785 nm.

Differential Scanning Calorimetry (DSC)

Instrument configuration: Q 1000 TA, not ermetic sample pan, run @10K/min to 150° C., N2 Flow=50 mL/min, sample 1.5-5 mg.

Example 15

Synthesis of [3-(2,4-dimethoxy-phenyl)-2,5-dimethyl-pyrazolo[1,5-a]pyrimidin-7-yl]-(2-methoxyethyl)-(3-methyl-[1,2,4]oxadiazol-5-ylmethyl)-amine

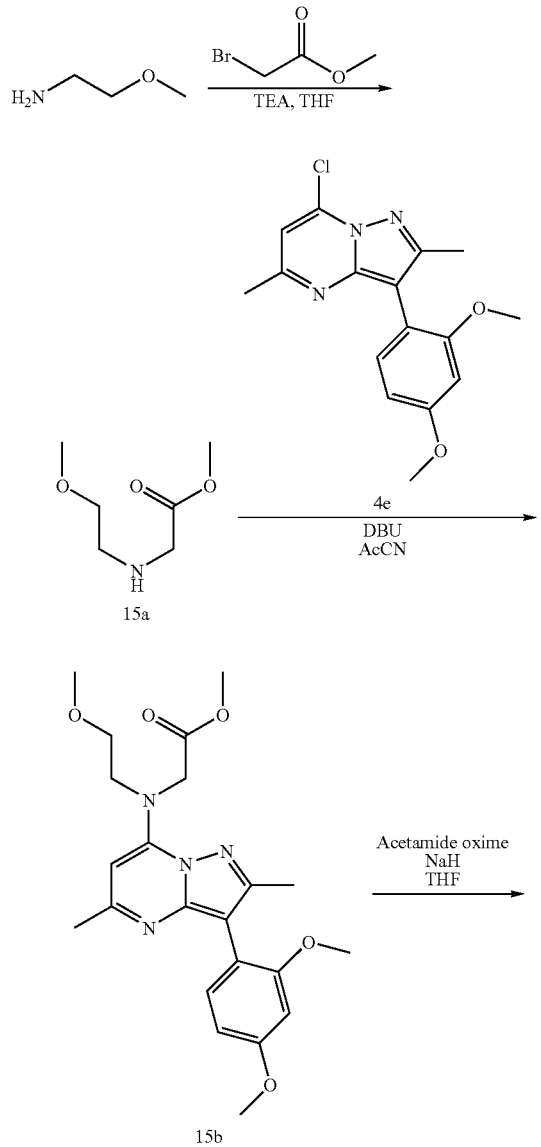

90

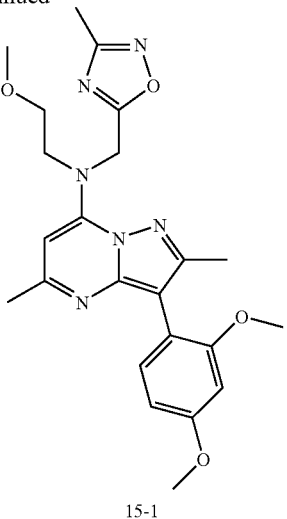

15-1

Step 15A:

To a solution of 2-methoxyethylamine (2.9 mL) in THF (40 mL) was added triethylamine (9.3 mL) followed by methyl bromoacetate (2.8 mL). The mixture was stirred at RT for 16 hr, then the solvent was evaporated. The residue was dissolved in ethyl acetate (100 mL), washed with water (2×50 mL), brine (50 mL), then the organic layer was dried over magnesium sulfate and concentrated. The residue was purified by silica gel chromatography using 95:5 dichloromethane/methanol as eluant to give 15a (1.8 g, 37% yield) as a colorless liquid. $^1$H NMR (CDCl$_3$, 300 MHz): 2.78 (t, 2H, J=3 Hz), 3.33 (s, 3H), 3.43 (s, 2H), 3.48 (t, 2H, J=3 Hz), 3.70 (s, 3H).

Step 15B:

DBU (0.22 mL) and Cmpd 15a (220 mg) were added to a solution of Cmpd 4e (400 mg) in acetonitrile (4 mL). The solution was stirred and heated at 80° C. for 16 hr. The cooled mixture was concentrated, then ethyl acetate (20 mL) was added. The mixture was washed with water (2×10 mL), then brine (10 mL), and the resulting organic layer was dried over magnesium sulfate, filtered, and concentrated. The residue was purified by silica gel column chromatography using 95:5 dichloromethane/methanol as eluant to provide Cmpd 15b as an oil. Mass: 428.8 (MH$^+$); HPLC: Analytical Method 2, retention time 1.46 min.

Step 15C:

A suspension of acetamide oxime (60 mg in anhydrous THF (5 mL) was stirred at RT as NaH (32 mg of 60% dispersion in oil) was added. The mixture was stirred for 45 min at RT, then a solution of Cmpd 15b (173 mg) in anhydrous THF (5 mL) was added. The mixture was refluxed for 2 hr. The cooled mixture was concentrated, then taken up in ethyl acetate (10 mL) and washed with water (2×10 mL) and brine (10 mL). The resulting organic layer was dried over magnesium sulfate, filtered, and evaporated. The residue was purified by preparative LC/MS to provide Cmpd 15-1. Mass: 452.8 (MH$^+$); HPLC: Analytical Method 2, retention time 1.406 min.

Depending on the pyrazolo-[1,5a]-pyrimidine, amino acid ester and oxime reagent, the compounds in the following table were prepared:

TABLE 5

| Cmpd | | | MW | MS | $t_R$ |
|---|---|---|---|---|---|
| 15-1 | | | 452.51 | 452.8 | 1.408 |
| 15-2 | | | 432.53 | 433.2 | 3.192 |
| 15-3 | | | 450.54 | 450.2 | 3.22 |
| 15-4 | | | 436.51 | 436.8 | 1.17 |

Example 16

Synthesis of [3-(2,4-dimethoxy-phenyl)-2,5-dimethyl-pyrazolo[1,5-a]pyrimidin-7-yl]-(2-methoxy-ethyl)-[3-(3-methyl-[1,2,4]oxadiazol-5-yl)-propyl]-amine

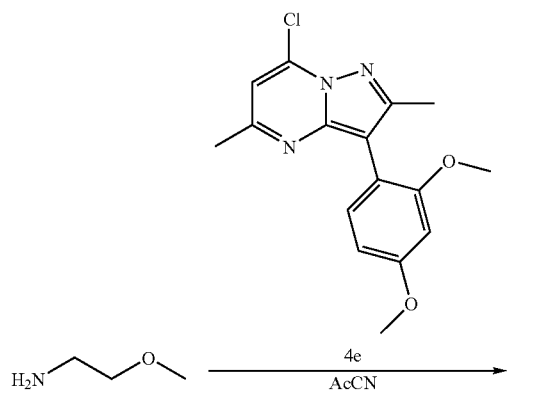

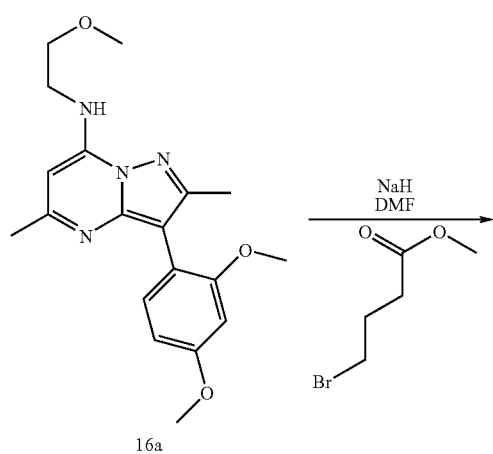

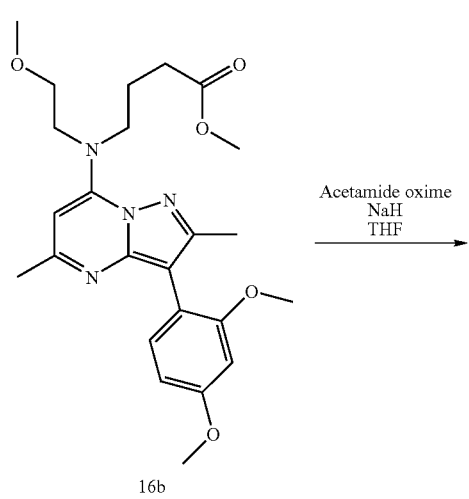

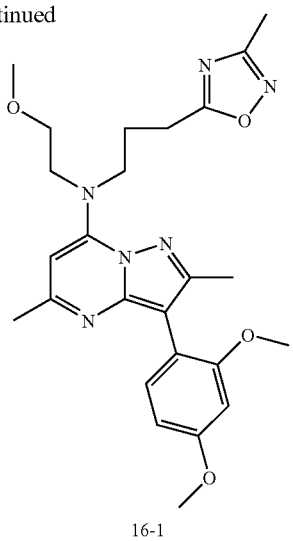

Step 16A:

To Cmpd 4e (200 mg) in acetonitrile (5 mL) was added 2-methoxyethylamine (2 mL). The solution was stirred and heated at 80° C. for 16 hr. The mixture was concentrated under vacuum. The residue was dissolved in ethyl acetate (5 mL), and the resulting solution was washed with water (2×5 mL) and brine (5 mL). Drying over magnesium sulfate, filtration, and concentration provided a yellow oil, Cmpd 16a, which was used in the following step without purification.

Step 16B:

Sodium hydride (76 mg of a 60% dispersion in oil) was added to a solution of 16a prepared in Step 16A in DMF (5 mL). After 5 minutes at RT, methyl 4-bromobutyrate (0.21 mL) was added. The mixture was heated for 48 hr at 60° C. in a sealed vial. The cooled mixture was concentrated, taken up in ethyl acetate (25 mL) and washed successively with water (2×10 mL) and brine. The organic layer was dried over magnesium sulfate, filtered, and concentrated. The crude residue 16b was used without further purification.

Step 16C:

Crude Cmpd 16b, prepared above in Step 16B, was subjected to the procedure of Step 15C. The crude reaction mixture was diluted with methanol, then purified directly by preparative LC/MS to afford Cmpd 16-1. Mass: 480.8 (MH$^+$); HPLC: Analytical Method 2, retention time 1.353 min.

Example 17

Synthesis of [3-(4-methoxy-2-methyl-phenyl)-2,5-dimethyl-pyrazolo[1,5-a]pyrimidin-7-yl]-[(R)-1-methyl-2-(5-methyl-[1,2,4]oxadiazol-3-yl)-ethyl]-amine

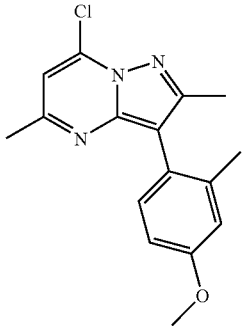

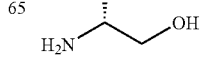

-continued

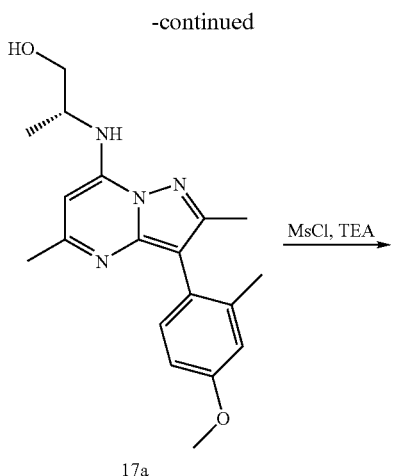

17a

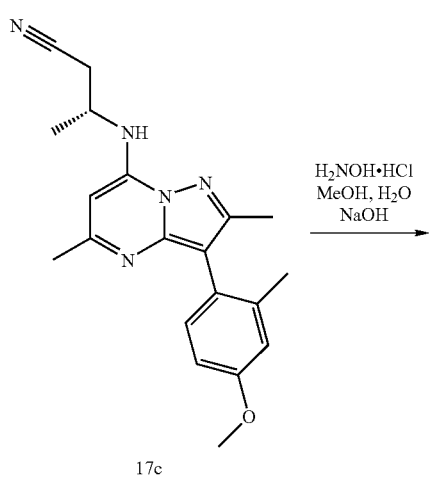

17b

17c

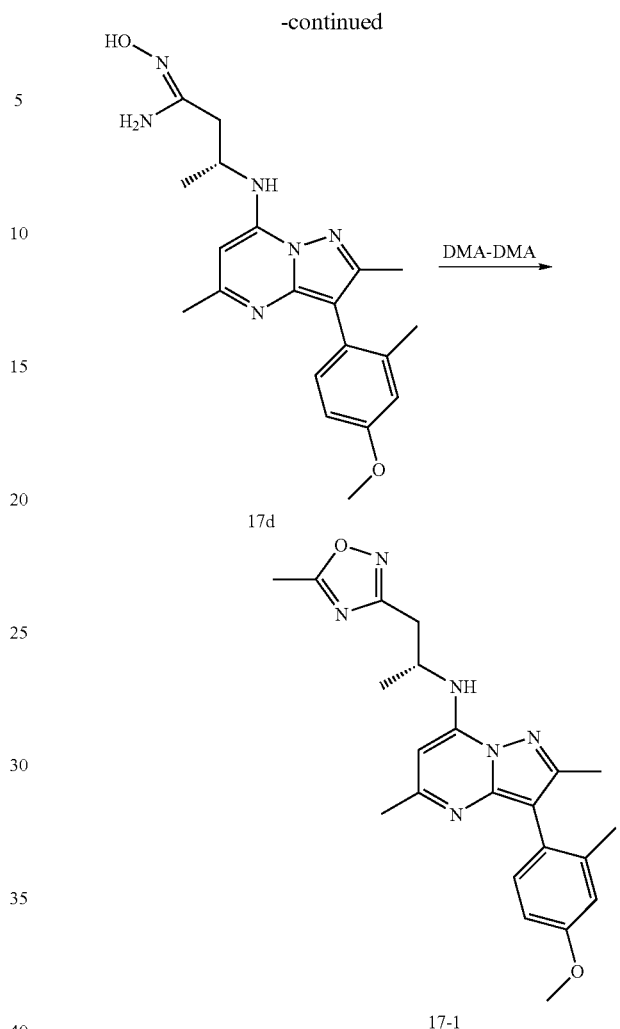

17d 17-1

Step 17A:

A mixture of Cmpd 4d (1.0 g), (R)-2-amino-1-propanol (0.5 g), triethylamine (0.91 mL), and acetonitrile (5 mL) was heated with stirring at 90° C. for 4 hr. The reaction mixture was partitioned between saturated aq. sodium bicarbonate and ethyl acetate. The aqueous layer was extracted with one additional portion of ethyl acetate, then the combined organic layers were dried over sodium sulfate and concentrated to provide Cmpd 17a as a yellow oil, which was used without further purification.

Step 17B:

A solution of methanesulfonyl chloride (0.68 g) in DCM (1.0 mL) was added dropwise to a stirred mixture of crude Cmpd 17a (prepared above), triethylamine (0.91 mL), and DCM. A clear brown solution resulted, and the mixture was stirred at RT for 30 min. Saturated aq. sodium bicarbonate solution was added, and the mixture was extracted with ethyl acetate (2×25 mL). The combined organic layers were washed once with potassium carbonate solution and were then dried over sodium sulfate, filtered, and concentrated to provide Cmpd 17b as a white foam. This material was used without further purification.

Step 17C:

Powdered sodium cyanide (0.33 g) and potassium carbonate (0.92 g) were added to a solution of Cmpd 17b (prepared above) in DMF (10 mL). The mixture was heated in a sealed tube at 100° C. for 4 hr, forming a thick gel. Saturated aq. sodium bicarbonate solution (25 mL) was added and the mixture was extracted with ethyl acetate (2×25 mL). The combined organic layers were dried over sodium sulfate, filtered, and concentrated. The residue was purified by silica gel chromatography using 30% ethyl acetate in hexane as eluant, providing Cmpd 17c (0.72 g, 62% yield) as a slightly yellow oil.

Step 17D:

A solution of Cmpd 17c (200 mg) in ethanol (4 mL) was treated with hydroxylamine hydrochloride (50 mg) and potassium hydroxide (40 mg). The mixture was stirred and heated at 100° C. in a sealed tube for 4 hr. The cooled mixture was filtered, and the filter cake was washed twice with 5 mL cold ethanol. The combined filtrates were concentrated providing Cmpd 17d as a white solid which was used without further purification.

Step 17E:

Cmpd 17d (prepared above) was dissolved in N,N-dimethylacetamide dimethylacetal (4 mL). The mixture was heated at 100° C. for 2 hr. The mixture was concentrated and the residue was purified by silica gel chromatography, eluting with 30% ethyl acetate in hexane. The product was converted into the HCl salt following the procedure of Step 14C: 72 mg (28% yield).

Depending on the pyrazolo-[1,5a]-pyrimidine, amino acid ester and oxime reagent, the compounds in the following table were prepared:

TABLE 6

| Cmpd | | MW | MS | $t_R$* |
|---|---|---|---|---|
| 17-1 | | 406.49 | 407 | 4.37 |
| 17-2 | | 420.51 | 421 | 4.63 |
| 17-3 | | 420.51 | 421 | 4.84 |
| 17-4 | | 406.49 | 407 | 4.70 |

*All HPLC employed Analytical Method 1.

Example 18

Synthesis of [(R)-2-(5-cyclopropyl-[1,2,4]oxadiazol-3-yl)-1-methyl-ethyl]-[3-(4-methoxy-2-methyl-phenyl)-2,5-dimethyl-pyrazolo[1,5-a]pyrimidin-7-yl]-amine

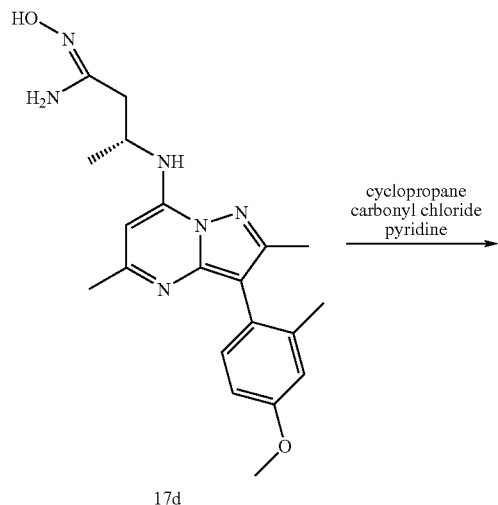

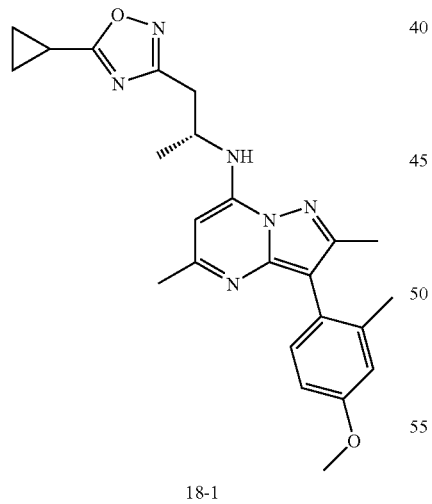

Step 18A:

Crude Cmpd 17d (100 mg) was dissolved in 2 mL pyridine and treated with cyclopropanecarbonyl chloride (0.024 mL). The mixture was heated in a sealed tube at 80° C. for 2 hr, then the solvent was evaporated and the residue was purified by preparative LC/MS.

Depending on the pyrazolo-[1,5a]-pyrimidine and carbonyl chloride reagent, the compounds in the following table were prepared:

TABLE 7

| Cmpd | $R_5$ | MW | MS | $t_R$* |
|---|---|---|---|---|
| 18-1 | ⟨cyclopropyl⟩ | 432.52 | 433 | 5.36 |
| 18-2 | —CF$_3$ | 460.46 | 461 | 5.14 |

*All HPLC employed Analytical Method 1.

Example 19

Synthesis of [3-(4-methoxy-2-methyl-phenyl)-2,5-dimethyl-pyrazolo[1,5-a]pyrimidin-7-yl]-[(S)-2,2,2-trifluoro-1-(5-methyl-[1,2,4]oxadiazol-3-ylmethyl)-ethyl]-amine

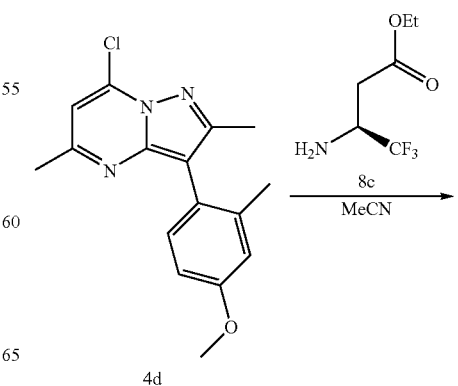

-continued

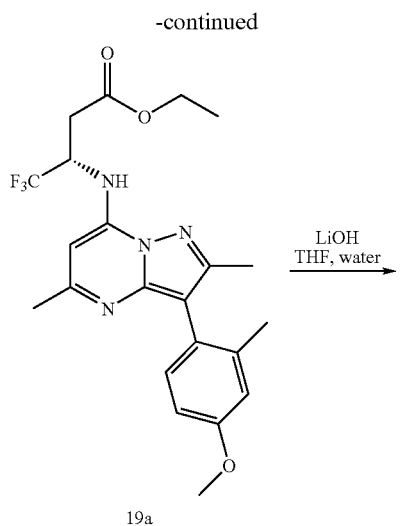

19a

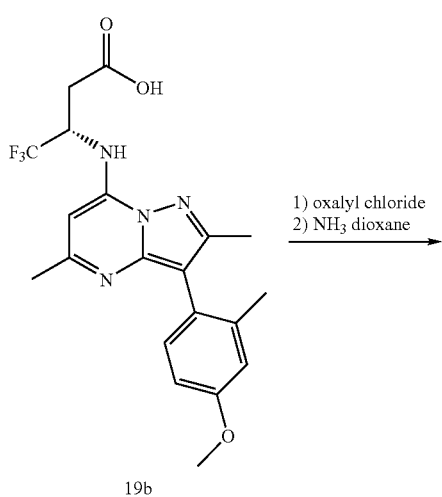

19b

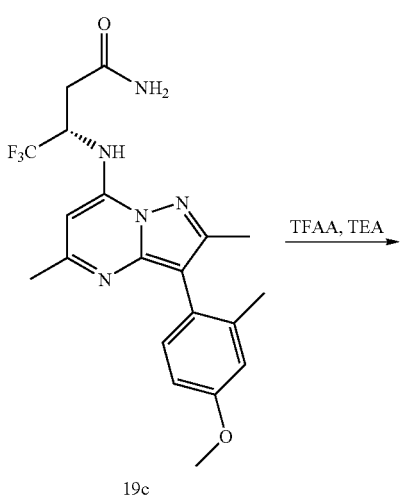

19c

-continued

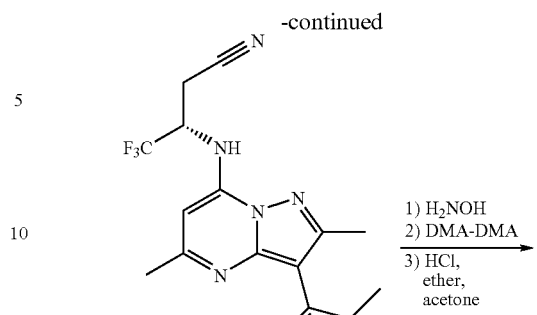

19d

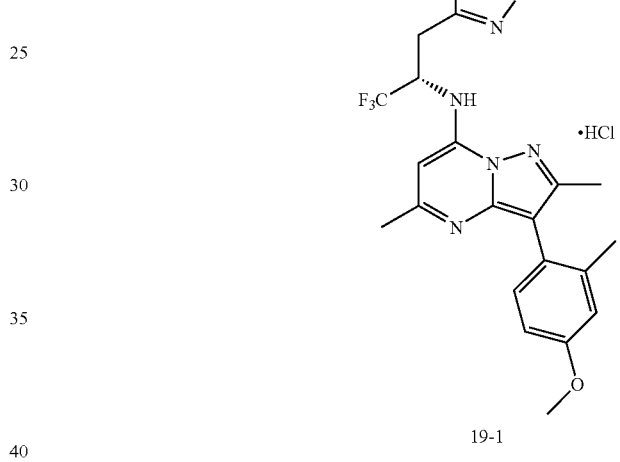

19-1

Step 19A:

A mixture of 4d (565 mg) and 8c (400 mg) in acetonitrile (3.5 mL) was heated in a sealed tube in a microwave reactor at 150° C. for 30 min. Aqueous sodium bicarbonate solution was added, and the mixture was extracted once with 3:1 hexanes/ethyl acetate then once with ethyl acetate. The combined organic layers were dried over sodium sulfate, filtered, and concentrated. The residue was purified by silica gel chromatography using 3:1 hexanes/ethyl acetate as eluant to provide 19a (410 mg, 53%) as a slightly yellow oil.

Step 19B:

A mixture of 19a (1.1 g), lithium hydroxide (300 mg), THF (10 mL), and water (2 mL) was heated at 90° C. for 2 hr. The cooled reaction mixture was treated with 4M hydrochloric acid (5 mL) and water (25 mL), and the resulting mixture was extracted twice with ethyl acetate. The combined organic layers were dried over sodium sulfate, filtered, and evaporated to provide crude 19b (1.1 g) as a yellow oil, which was used without further purification.

Step 19C:

A solution of crude 19b (1.1 g) in THF (10 mL) at RT was treated with oxalyl chloride (0.34 g), followed by two drops of DMF. Vigorous gas evolution was observed, and the mixture was stirred at RT for 1 hr. The reaction mixture was concentrated, then ammonia (20 mL of a 2.0 M solution in dioxane) was added, and the resulting suspension was stirred at RT for 16 hr. Aqueous sodium bicarbonate solution was added, and the mixture was extracted twice with ethyl acetate. The organic layers were combined, dried over sodium sulfate, filtered, and concentrated to provide 19c (700 mg) as a pale green oil, which was used without further purification.

Step 19D:

A solution of 19c (700 mg) and TEA (750 mg) in dioxane (10 mL) was treated at RT with trifluoroacetic anhydride (1.5 g). The reaction mixture was stirred at RT for 2 hr, then aq. sodium bicarbonate solution was added and the mixture was extracted twice with dichloromethane. The combined organic layers were dried over sodium sulfate, filtered, and concentrated. The residue was purified by silica gel chromatography, using 30% ethyl acetate in hexanes as eluant, providing 19d (400 mg) as a yellow oil.

Step 19E:

To a solution of 19d (400 mg) in ethanol (10 mL) was added hydroxylamine hydrochloride (85 mg) and potassium hydroxide (70 mg). The mixture was heated at 100° C. for 4 hr. The reaction mixture was cooled to RT and filtered, and the filter cake was washed with ethanol. The combined filtrates were concentrated, then the residue was dissolved in DMA-DMA (10 mL) and heated at 90° C. for 2 hr. The reaction mixture was concentrated, and the residue was purified by silica gel chromatography, eluting with 3:1 hexanes/ethyl acetate to provide 19e free base (70 mg) as a yellow oil. The free base was dissolved in acetone (5 mL) and treated with hydrogen chloride (2 mL of 2.0 M solution in ether). The mixture was concentrated in vacuo to provide 19-1HCl salt (75 mg) as a yellow solid. Mass: 461.0 (MH$^+$); HPLC: Analytical Method 1, retention time 5.28 min.

Example 20

Synthesis Of Ethyl-[3-(4-methoxy-2-methyl-phenyl)-2,5-dimethyl-pyrazolo[1,5-a]pyrimidin-7-yl]-(3-methyl-[1,2,4]oxadiazol-5-ylmethyl)-amine

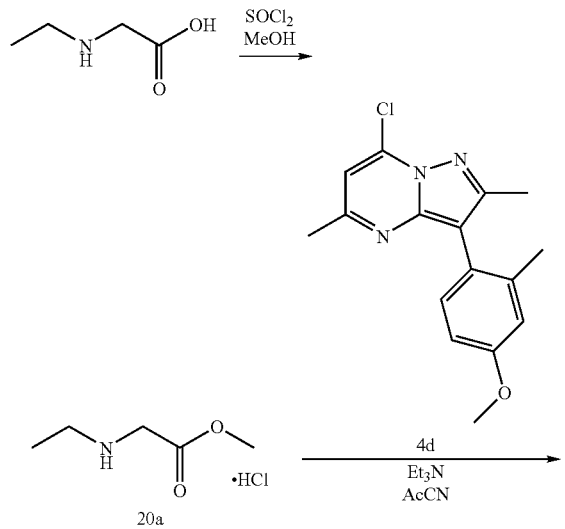

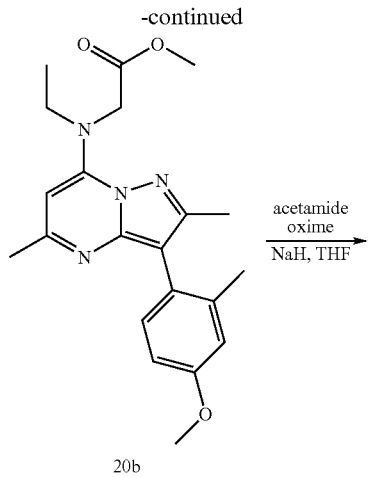

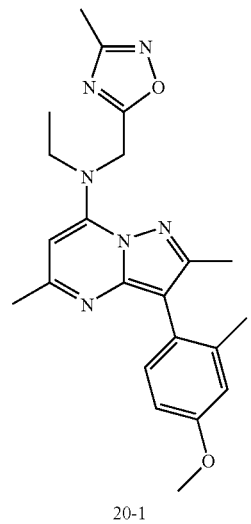

Step 20A:

Thionyl chloride (0.71 mL) was added carefully to a cold solution of N-ethyl glycine (0.50 g) dissolved in anhydrous methanol (8 mL). The mixture was heated at 60° C. for 14 hr in a sealed tube. The mixture was concentrated then subjected to co-evaporation with toluene (2×) and acetonitrile (3×). Drying under vacuum gave the amino ester hydrochloride salt 20a as a white gummy solid, which was carried on directly without further purification.

Step 20B:

The condensation of Cmpds 20a and 4d by the procedure of Step 11A provided Cmpd 20b (164 mg) as a yellow oil after silica gel chromatography.

Step 20C:

Compound 20b (164 mg) was subjected to the procedure of Step 11B to afford Cmpd 20-1 (105 mg) as a slightly yellow oil after silica gel chromatography employing hexanes/ethyl acetate eluant.

Depending on the pyrazolo-[1,5a]-pyrimidine, amino acid ester and oxime reagent, the compounds in the following table were prepared:
TABLE 8
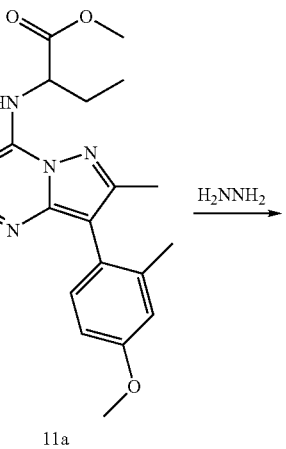
| Cmpd | | MW | MS | $t_R$* |
|---|---|---|---|---|
| 20-1 | | 406.49 | 407.0 | 5.135 |
| 20-2 | | 446.55 | 447.1 | 5.660 |
*All HPLC employed Analytical Method 1.
Example 21
Synthesis Of [3-(4-methoxy-2-methyl-phenyl)-2,5-dimethyl-pyrazolo[1,5-a]pyrimidin-7-yl]-(1-[1,3,4]oxadiazol-2-yl-propyl)-amine
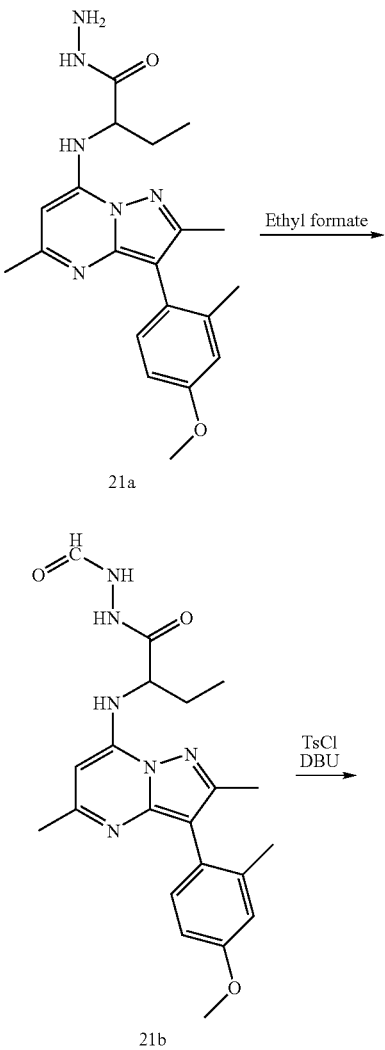

-continued

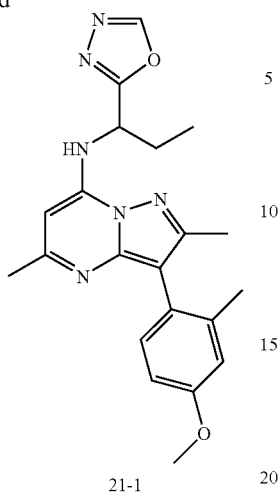

21-1

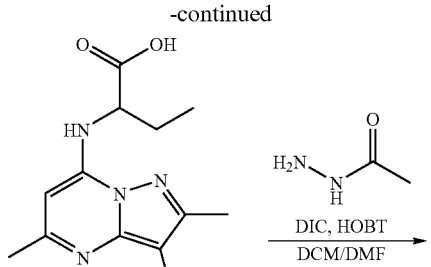

22a

Step 21A:
Hydrazine hydrate (0.50 mL) was added to a suspension of Cmpd 11a (230 mg) in ethanol (1.5 mL) at RT. The reaction vessel was sealed and heated with stirring at 75° C. for 17 hr. The clear solution was cooled and concentrated to provide the hydrazide Cmpd 21a as an oil (230 mg).

Step 21B:
Crude 21a from the preceeding step (70 mg) was dissolved in ethyl formate (2 mL) and heated at 65° C. for 72 hr. The cooled solution was concentrated to provide the crude diacyl hydrazine Cmpd 21b (70 mg) as an oil.

Step 21C:
A mixture of Cmpd 21b from the preceeding step (29 mg), p-toluenesulfonyl chloride (27 mg), DBU (0.053 mL), and THF (0.5 mL) was heated in a microwave reactor at 150° C. for 10 min. Aqueous sodium bicarbonate solution was added, and the mixture was extracted with ethyl acetate. The combined organic extracts were dried over sodium sulfate, filtered, and evaporated. The residue was purified by preparative thin-layer silica gel chromatography, eluting with 1:2 hexanes/ethyl acetate to afford Cmpd 21-1 as an oil (12 mg). Mass: 393.0 (MH+); HPLC: Analytical Method 4, retention time 2.40 min.

Example 22

Synthesis Of [3-(4-methoxy-2-methyl-phenyl)-2,5-dimethyl-pyrazolo[1,5-a]pyrimidin-7-yl]-[1-(5-methyl-[1,3,4]oxadiazol-2-yl)-propyl]-amine

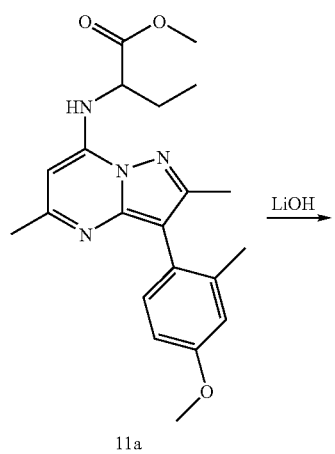

11a

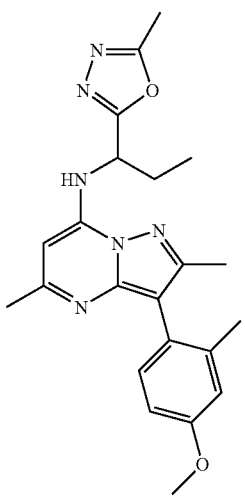

22b 22-1

Step 22A:
Compound 11a was subjected to lithium hydroxide hydrolysis according to the procedure of Step 13C giving Cmpd 22a as a white waxy solid.

Step 22B:

Compound 22a (100 mg) and N-acetylhydrazide were subjected to the procedure of Step 14B. The crude ethyl acetate extract was dried over magnesium sulfate; filtered, and concentrated to provide Cmpd 22b (110 mg, 96%) as a white solid.

Step 22C:

Compound 22b (50 mg) was subjected to the procedure of Step 21C with heating in a microwave reactor at 150° C. for 15 min. The resultant was purified by preparative thin-layer silica gel chromatography, eluting with 48:48:4 hexanes/ethyl acetate/methanol to yield Cmpd 22-1 (8 mg, 71%) as a solid. Mass: 407.0 (MH$^+$); HPLC: Analytical Method 1, retention time 4.543 min.

Example 23

Synthesis Of [3-(4-methoxy-2-methyl-phenyl)-2,5-dimethyl-pyrazolo[1,5-a]pyrimidin-7-yl]-[1-methyl-2-(5-methyl-[1,3,4]oxadiazol-2-yl)-ethyl]-amine

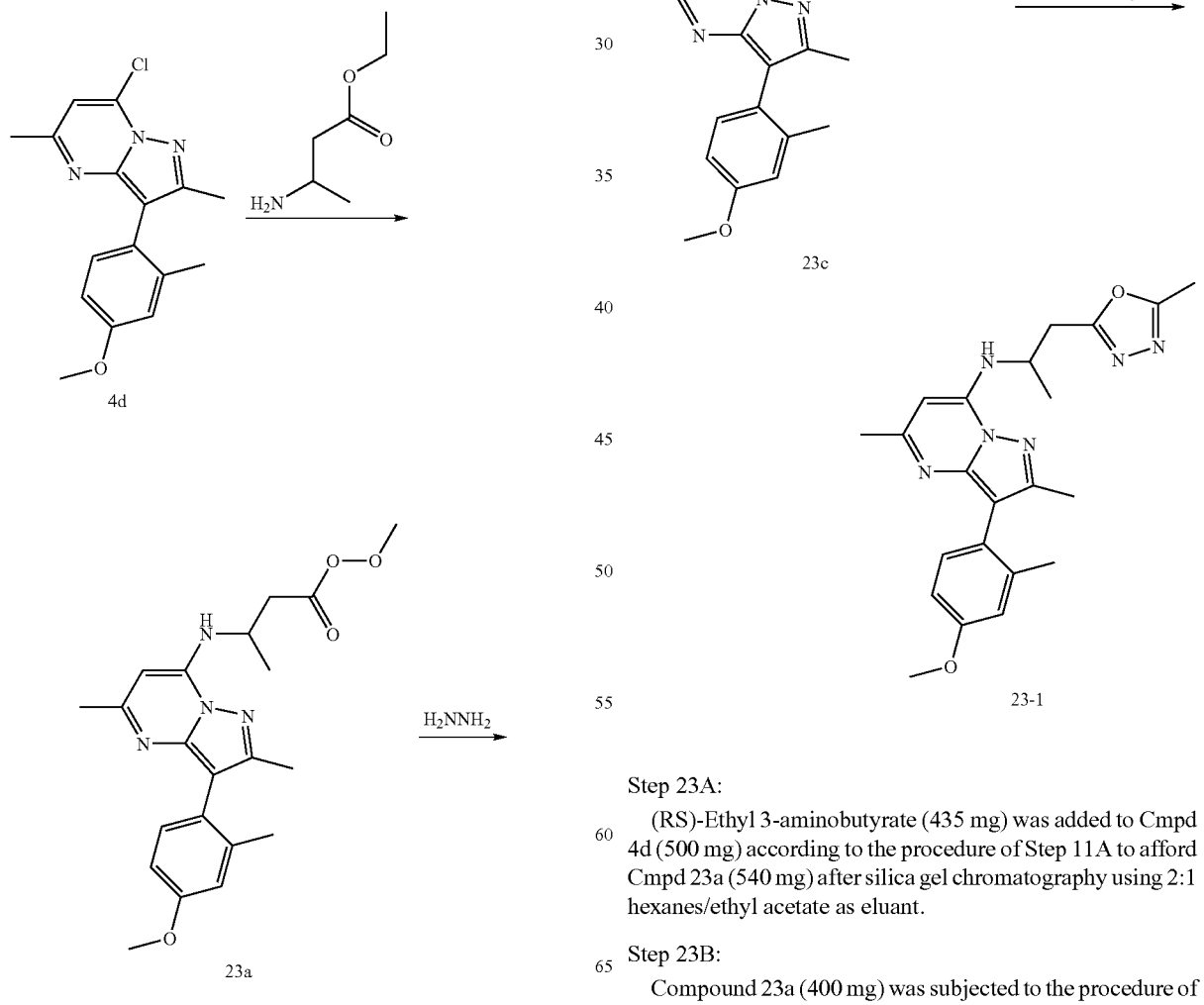

Step 23A:

(RS)-Ethyl 3-aminobutyrate (435 mg) was added to Cmpd 4d (500 mg) according to the procedure of Step 11A to afford Cmpd 23a (540 mg) after silica gel chromatography using 2:1 hexanes/ethyl acetate as eluant.

Step 23B:

Compound 23a (400 mg) was subjected to the procedure of Step 21A to afford Cmpd 23b (367 mg).

111

Step 23C:

A solution of Cmpd 23b (180 mg) and triethylamine (0.100 mL) in DCM (4 mL) was treated with acetic anhydride (0.53 mL) at RT. After 17 hr, additional triethylamine (0.100 mL) and acetic anhydride (0.53 mL) were added. The solvent was evaporated, then aq. sodium bicarbonate solution was added and the mixture was extracted with DCM (4×10 mL). The combined organic extracts were washed with brine, dried over sodium sulfate, filtered, and evaporated. The residue was chromatographed on silica gel eluting with 5% methanol in DCM to afford Cmpd 23c (165 mg).

Step 23D:

Compound 23c (50 mg) was subjected to the procedure of Step 21C substituting 1,3,4,6,7,8-hexahydro-1-methyl-2H-pyrimido[1,2-A]pyrimidine in place of DBU. Purification by preparative thin-layer silica gel chromatography (1:1 hexanes/acetone as eluant) provided Cmpd 23-1 (12 mg).

Depending on the pyrazolo-[1,5a]-pyrimidine, amino acid ester and oxime reagent, the compounds in the following table were prepared:

TABLE 9

| Cmpd | R$_5$ | MW | MS | t$_R$* |
|---|---|---|---|---|
| 23-1 | —CH$_3$ | 406.49 | 407.0 | 4.391 |
| 23-2 | —CF$_3$ | 460.46 | 461.0 | 5.644 |

*All HPLC employed Analytical Method 1.

112

Example 24

Synthesis Of [3-(2-chloro-4-methoxy-phenyl)-2,5-dimethyl-pyrazolo[1,5-a]pyrimidin-7-yl]-[1-(3-methyl-[1,2,4] oxadiazol-5-yl)-propyl]-amine

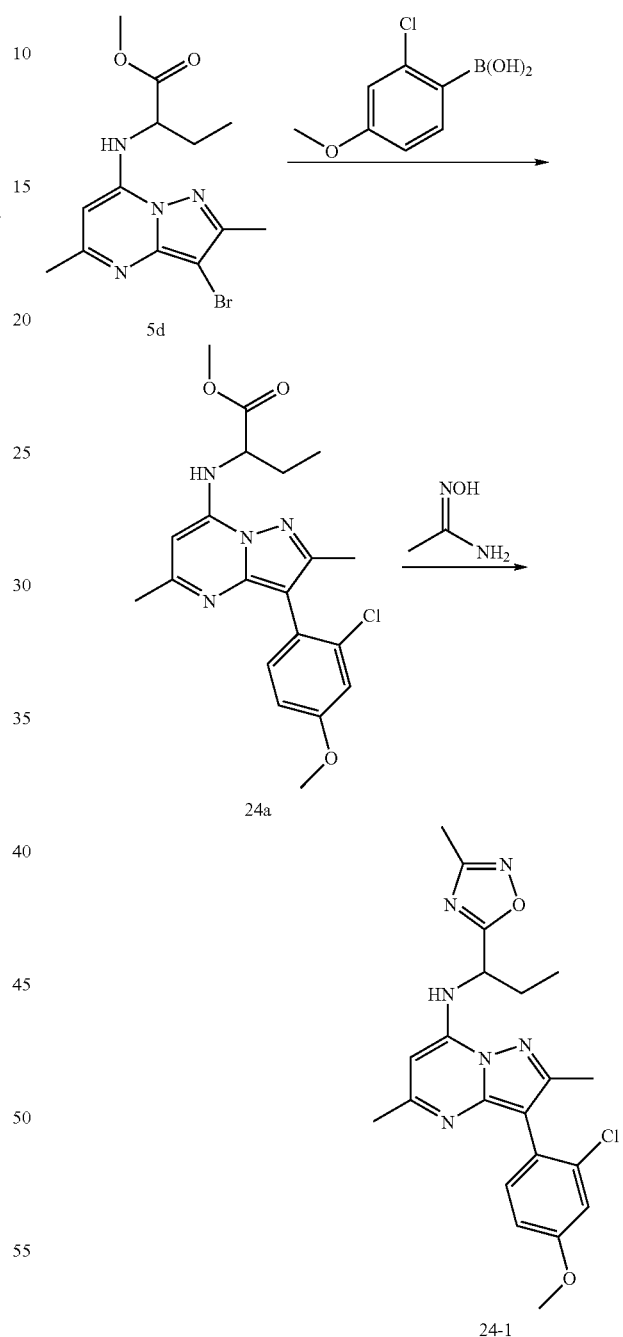

Step 24A:

To Cmpd 5d (100 mgl) was added 2-chloro-4-methoxyphenylboronic acid (70 mg) followed by potassium carbonate (80 mg) and a solution of dioxane/water (0.9 mL/0.2 mL). The reaction mixture was sparged with nitrogen for 5 min, then tetrakis(triphenylphosphine)palladium(0) (80 mg) was added, and the reaction vessel was sealed and heated at 85° C.

for 16 hr. The solvent was evaporated, and the residue was purified directly by preparative thin-layer silica gel chromatography using 30% ethyl acetate in hexanes as eluant, providing Cmpd 24a as a solid (31 mg, 26%). LC/MS: 403.0 (MH$^+$)

Step 24B:

Compound 24a (31 mg) and acetamidoxime were subjected to the procedure of S1Bb to afford Cmpd 24-1 (5.17 mg) after preparative thin-layer silica gel chromatography (1:1 hexanes/ethyl acetate eluant).

Depending on the pyrazolo-[1,5a]-pyrimidine, amino acid ester and oxime reagent, the compounds in the following table were prepared:

TABLE 10

| Cmpd | (structure) | MW | MS | $t_R$* |
|---|---|---|---|---|
| 24-1 | 2-Cl, 4-OMe phenyl | 426.91 | 427.0 | 4.76 |
| 24-2 | 2-OMe, 5-Cl phenyl | 426.91 | 427.0 | 4.887 |

TABLE 10-continued

| Cmpd | (structure) | MW | MS | $t_R$* |
|---|---|---|---|---|
| 24-3 | 3-Cl, 4-F phenyl | 414.87 | 415.0 | 5.209 |
| 24-4 | 2-Me, 4-Cl phenyl | 410.91 | 411.0 | 4.91 |
| 24-5 | 2-Cl, 4-CF$_3$ phenyl | 464.88 | 464.9 | 5.888 |
| 24-6 | 2-Cl, 4-Me phenyl | 410.91 | 411.0 | 5.102 |

*All HPLC employed Analytical Method 1.

Example 25

CRF Receptor Binding Activity

The compounds of this invention may be evaluated for binding activity to the CRF receptor by a standard radioligand binding assay as generally described by Grigoriadis et al. (*Mol. Pharmacol* vol 50, pp 679-686, 1996) and Hoare et al. (*Mol. Pharmacol* vol 63 pp 751-765, 2003). By utilizing radiolabeled CRF ligands, the assay may be used to evaluate the binding activity of the compounds of the present invention with any CRF receptor subtype.

Briefly, the binding assay involves the displacement of a radiolabeled CRF ligand from the CRF receptor. More specifically, the binding assay is performed in 96-well assay plates using 1-10 μg cell membranes from cells stably transfected with human CRF receptors. Each well receives about 0.05 mL assay buffer (e.g., Dulbecco's phosphate buffered saline, 10 mM magnesium chloride, 2 mM EGTA) containing compound of interest or a reference ligand (for example, sauvagine, urocortin I or CRF), 0.05 mL of [$^{125}$I] tyrosine-sauvagine (final concentration ~150 pM or approximately the $K_D$ as determined by Scatchard analysis) and 0.1 mL of a cell membrane suspension containing the CRF receptor. The mixture is incubated for 2 hours at 22° C. followed by separation of the bound and free radioligand by rapid filtration over glass fiber filters. Following three washes, the filters are dried and radioactivity (Auger electrons from $^{125}$I) is counted using a scintillation counter. All radioligand binding data may be analyzed using the non-linear least-squares curve-fitting programs Prism (GraphPad Software Inc) or XLfit (ID Business Solutions Ltd).

Example 26

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987) with modifications to adapt the assay to whole cell preparations.

More specifically, the standard assay mixture may contain the following in a final volume of 0.1 mL: 2 mM L-glutamine, 20 mM HEPES, and 1 mM IMBX in DMEM buffer. In stimulation studies, whole cells with the transfected CRF receptors are plated in 96-well plates and incubated for 30 min at 37° C. with various concentrations of CRF-related and unrelated peptides in order to establish the pharmacological rank-order profile of the particular receptor subtype. Following the incubation, cAMP in the samples is measured using standard commercially available kits, such as cAMP-Screen™ from Applied Biosystems. For the functional assessment of the compounds, cells and a single concentration of CRF or related peptides causing 50% stimulation of cAMP production are incubated along with various concentrations of competing compounds for 30 min at 37° C., and cAMP determined as described above.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound of the following formula:

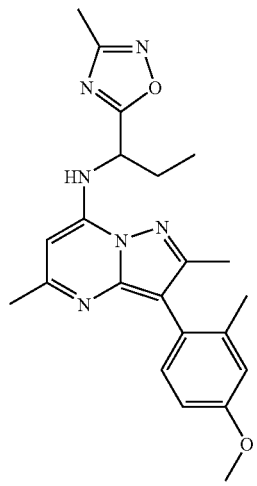

or a pharmaceutically acceptable salt thereof.

2. A pharmaceutical composition comprising a compound according to claim 1, or a pharmaceutically acceptable salt thereof, and a pharmaceutically acceptable carrier or diluent.

3. The pharmaceutical composition according to claim 2 formulated for systemic administration.

4. The pharmaceutical composition according to claim 3 formulated for oral administration.

5. The pharmaceutical composition according to claim 4 formulated as a tablet or capsule.

6. A compound of the following formula:

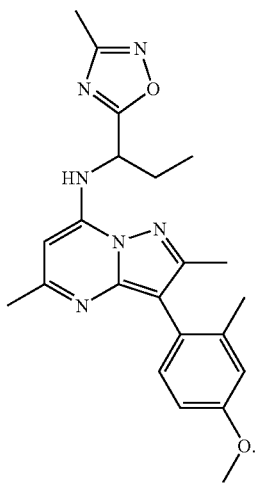

7. A pharmaceutical composition comprising a compound according to claim 6 and a pharmaceutically acceptable carrier or diluent.

8. The pharmaceutical composition according to claim 7 formulated for systemic administration.

9. The pharmaceutical composition according to claim 8 formulated for oral administration.

10. The pharmaceutical composition according to claim 9 formulated as a tablet or capsule.

11. A compound of the following formula:

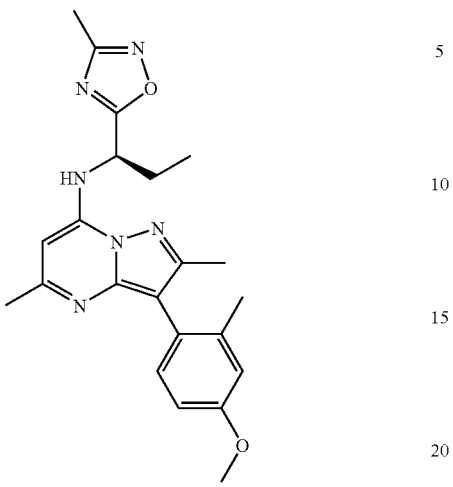

or a pharmaceutically acceptable salt thereof.

12. A pharmaceutical composition comprising a compound according to claim 11, or a pharmaceutically acceptable salt thereof, and a pharmaceutically acceptable carrier or diluent.

13. The pharmaceutical composition according to claim 12 formulated for systemic administration.

14. The pharmaceutical composition according to claim 13 formulated for oral administration.

15. The pharmaceutical composition according to claim 14 formulated as a tablet or capsule.

16. A compound of the following formula:

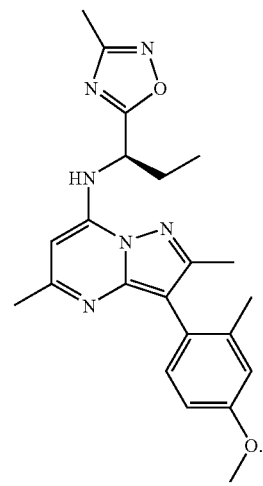

17. A pharmaceutical composition comprising a compound according to claim 16 and a pharmaceutically acceptable carrier or diluent.

18. The pharmaceutical composition according to claim 17 formulated for systemic administration.

19. The pharmaceutical composition according to claim 18 formulated for oral administration.

20. The pharmaceutical composition according to claim 19 formulated as a tablet or capsule.

\* \* \* \* \*